US008617818B2

(12) United States Patent
Tsichlis et al.

(10) Patent No.: US 8,617,818 B2
(45) Date of Patent: Dec. 31, 2013

(54) COMPOSITIONS AND METHODS FOR DIAGNOSIS AND PROGNOSIS OF CANCER AND PROGRESSION, AND FOR SCREENING ANTI-CANCER AGENTS

(75) Inventors: Philip N. Tsichlis, Winchester, MA (US); Christos Polytarchou, Boston, MA (US); Dimitrios Iliopoulos, Brighton, MA (US)

(73) Assignees: Tufts Medical Center, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/249,477

(22) Filed: Sep. 30, 2011

(65) Prior Publication Data
US 2012/0021983 A1    Jan. 26, 2012

Related U.S. Application Data

(63) Continuation of application No. PCT/US2010/029804, filed on Apr. 2, 2010.

(60) Provisional application No. 61/212,717, filed on Apr. 14, 2009, provisional application No. 61/211,726, filed on Apr. 2, 2009.

(51) Int. Cl.
C12Q 1/68    (2006.01)

(52) U.S. Cl.
USPC ........................................ 435/6.14; 435/6.12

(58) Field of Classification Search
None
See application file for complete search history.

(56) References Cited

PUBLICATIONS

Strausberg et al, In Microarrays and Cancer Research, 2002, Warrington et al (eds.), Eaton Publishing, Westborough, MA, pp. xi-xvi.*
Notterman et al, In Microarrays and Cancer Research, 2002, Warrington et al (eds.), Eaton Publishing, Westborough, MA, pp. 81-111.*
Wright et al. "VEGF stimulation of mitochondrial biogenesis: requirement of AKT3 kinase" FASEB J 2008, vol. 22, pp. 3264-3275.
Wu et al. "Expression profile of mammalian microRNAs in endometrioid adenocarcinoma" Eur J Cancer Preven, 2009, vol. 18, pp. 50-55.
Xie et al. "Reactive Oxygen Species-induced Phosphorylation of p53 on Serine 20 Is Mediated in Part by Polo-like Kinase-3*" J Biol Chem, 2001, vol. 276, pp. 36194-36199.
Yoeli-Lerner et al. "Akt Blocks Breast Cancer Cell Motility and Invasion through the Transcription Factor NFAT" Mol Cell, 2005, vol. 20, pp. 539-550.
Zanette et al. "miRNA expression profiles in chronic lymphocytic and acute lymphocytic leukemia" Braz J Med Biol Res, 2007, vol. 40, pp. 1435-1440.
Zeng et al. "The Emerging Role of the Hippo Pathway in Cell Contact Inhibition, Organ Size Control, and Cancer Development in Mammals" Cancer Cell, 2008, vol. 13, pp. 188-192.
Zhu et al. "MicroRNA-21 Targets the Tumor Suppressor Gene Tropomyosin 1 (TPM1)*" J Biol Chem, 2007, vol. 282, pp. 14328-14336.
Altomare et al. "Perturbations of the AKT signaling pathway in human cancer" Oncogene 2005, vol. 24, pp. 7455-7464.
Bellacosa et al. "A Retroviral Oncogene, akt, Encoding a Serine-Threonine Kinase Containing an SH2-Like Region" Science, 1991, vol. 254, pp. 254-257.
Calin et al. "MicroRNA profiling reveals distinct signatures in B cell chronic lymphocytic leukemias" Proc Natl Acad Sci, 2004, vol. 101, pp. 11755-11760.
Cheng et al. "AKT2, a putative oncogene encoding a member of a subfamily of protein-serine/threonine kinases, is amplified in human ovarian carcinomas" Proc Natl Acad Sci, 1992, vol. 89, pp. 9267-9271.
Cheng et al. "Advances of AKT Pathway in Human Oncogenesis and as a Target for Anti-Cancer Drug Discovery" Curr Canc Drug Targ, 2008, vol. 8, pp. 2-6.
Chiang et al. "Molecular Origins of Cancer: Molecular Basis of Metastasis" N Eng J Med, 2008, vol. 359, pp. 2814-2823.
Cimmino et al. "miR-15 and miR-16 induce apoptosis by targeting BCL2" Proc Natl Acad Sci, 2005, vol. 102, pp. 13944-13949.
Cloonan et al. "The miR-17-5p microRNA is a key regulator of the G1/S phase cell cycle transition" Genome Biol, 2008, vol. 9, R127.
Croce "Causes and consequences of microRNA dysregulation in cancer" Nature, 2009, vol. 10, pp. 704-714.
Davis et al. "Biological Methods for Cell-Cycle Synchronization of Mammalian Cells" BioTechniques, 2001, vol. 30, pp. 1322-1331.
Dontu et al. "In vitro propagation and transcriptional profiling of human mammary stem/progenitor cells" Gene Develop, 2003, vol. 17, pp. 1253-1270.
Euskirchen et al. "Mapping of transcription factor binding regions in mammalian cells by ChIP: Comparison of array- and sequencing-based technologies" Genome Res, 2007, vol. 17, pp. 898-909.

(Continued)

Primary Examiner — James Martinell
(74) Attorney, Agent, or Firm — Sonia K. Guterman; Teofilo Javier, Jr.; Anna E. Stanford

(57) ABSTRACT

MicroRNA (miRNA) profiling of cells showed unique miRNA signatures for each of three Akt isoforms. Among differentially regulated miRNA species, the miR-200 family was downregulated in Akt2-expressing cells. Akt1 knockdown inhibited expression of miR-200 and promoted TGFβ-induced epithelial-mesenchymal-transition (EMT) and a stem cell like phenotype. Carcinomas developing in MMTV-cErb2/Akt1$^{-/-}$ mice exhibited increased invasiveness because of EMT induced by miR-200 downregulation. EMT was found to be controlled by miRNA species that are regulated by the balance between Akt1 and Akt2, rather than overall Akt levels.

13 Claims, 52 Drawing Sheets

(56) References Cited

PUBLICATIONS

Franke et al. "The protein kinase encoded by the Akt proto-oncogene is a target of the PDGF-activated phophatidylinositol 3-kinase" Cell, 1995, vol. 81, pp. 727-736.

Frankel et al. "Programmed Cell Death 4 (PDCD4) Is an Important Functional Target of the MicroRNA miR-21 in Breast Cancer Cells" J Biol Chem, vol. 238, pp. 1026-1033.

Gregory et al. "The miR-200 family and miR-205 regulate epithelial to mesenchymal transition by targeting ZEB1 and SIP1" Nat Cell Biol, 2008, vol. 10, pp. 593-601.

Guo et al. "Surface Elastic Properties of Human Retinal Pigment Epithelium Melanosomes" Photochem Photobiol, 2008, vol. 84, pp. 671-678.

He et al. "A microRNA component of the p53 tumour suppressor network" Nature, 2007, vol. 447, pp. 1130-1135.

Heatwole "Tunnel Assay for Apoptotic Cells" Methods in Molecular Biology, pp. 141-148 in vol. 115: Immunocyclochemical Methods and Protocols, 1999, ed. by L.C. Javois.

Hurteau et al. "Overexpression of the MicroRNA hsa-miR-200c Leads to Reduced Expression of Transcription Factor 8 and Increased Expression of E-Cadherin" Cancer Res, 2007, vol. 67, pp. 7972-7976.

Iliopoulos et al. "MicroRNAs differentially regulated by Akt isoforms control EMT and stem cell renewal in cancer cells" Sci Signal, 2009, vol. 2,ra62.

Irie et al. "Distinct roles of Akt1 and Akt2 in regulating cell migration and epithelial-mesenchymal transition" J Cell Biol, 2005, vol. 171, pp. 1023-1034.

Ito et al. "Magnetic granules: a novel system for specific drug delivery to esophageal mucosa in oral administration" Intl J Pharm, 1990, vol. 61, pp. 109-117.

Ju et al. "Akt1 governs breast cancer progression in vivo" Proc Natl Acad Sci, 2007, vol. 104, pp. 7438-7443.

Kron et al. "Discovery of Novel Hypermethylated Genes in Prostate Cancer Using Genomic CpG Island Microarrays" PLoS One, 2008, vol. 4, e4830.

Lennon et al. "Hybridization analyses of arrayed cDNA libraries" Trend Genet,1991, vol. 7, pp. 314-317.

Levy et al. "AKT inhibitor, GSK690693, induces growth inhibition and apoptosis in acute lymphoblastic leukemia cell lines" Blood, 2009, vol. 113, pp. 1723-1729.

Liu et al. "Mechanism of Akt1 inhibition of breast cancer cell invasion reveals a protumorigenic role for TSC2" Proc Natl Acad Sci, 2006, vol. 103, pp. 4134-4139.

Lu et al. "MicroRNA expression profiles classify human cancers" Nature, 2005, vol. 435, pp. 834-838.

Ma et al. "Tumour invasion and metastasis initiated by microRNA-10b in breast cancer" Nature, 2007, vol. 449, pp. 682-688.

Mani et al. "The Epithelial-Mesenchymal Transition Generates Cells with Properties of Stem Cells" Cell, 2008, vol. 133, pp. 704-715.

Manning et al. "AKT/PKB Signaling: Navigating Downstream" Cell, 2007, vol. 129, pp. 1261-1274.

Mao et al. "Unequal Contribution of Akt Isoforms in the Double-Negative to Double-Positive Thymocyte Transition" J Immunol, 2007, vol. 178, pp. 5443-5453.

Maroulakou et al. "Akt1 Ablation Inhibits, whereas Akt2 Ablation Accelerates, the Development of Mammary Adenocarcinomas in Mouse Mammary Tumor Virus (MMTV)-ErbB2/Neu and MMTV-Polyoma Middle T Transgenic Mice" Cancer Res, 2007, vol. 67, pp. 167-177.

Meek et al. "Establishment of mouse embryo cells in vitro: Relationship of DNA sythesis, senescence and malignant transformation" Exp Cell Res, 1977, vol. 107, pp. 277-284.

Meng et al. "Role of PI3K and AKT specific isoforms in ovarian cancer cell migration, invasion and proliferation through the p70S6K1 pathway" Cell Signal, 2006, vol. 18, pp. 2262-2271.

Mertens-Talcott et al. "The Oncogenic microRNA-27a Targets Genes That Regulate Specificity Protein Transcription Factors and the G2-M Checkpoint in MDA-MB-231 Breast Cancer Cells" Cancer Res, 2007, vol. 67, pp. 11001-11011.

Mizushima "Autophagy:process and function" Gene Develop, 2007, vol. 21, pp. 2861-2873.

Obernosterer et al. "Locked nucleic acid-based in situ detection of microRNAs in mouse tissue sections" Nature Protoc, 2007, vol. 2, pp. 1508-1514.

Ong et al. "Mass spectrometry-based proteomics turns quantitative" Nat Chem Biol, 2005, vol. 1, pp. 252-262.

Ouaamari et al. "miR-375 Targets 3'-Phosphoinositide-Dependent Protein Kinase-1 and Regulates Glucose-Induced Biological Responses in Pancreatic β-Cells" Diabetes, 2008, vol. 57, pp. 2708-2717.

Padmanabhan et al. "A PP2A Regulatory Subunit Regulates C. elegans Insulin/IGF-1 Signaling by Modulating AKT-1 Phosphorylation" Cell, 2009, vol. 136, pp. 939-951.

Park et al. "The miR-200 family determines the epithelial phenotype of cancer cells by targeting the E-cadherin repressors ZEB1 and ZEB2" Gene Develop, 2008, vol. 22, pp. 894-907.

Pickering et al. "miR-17 and miR-20a temper an E2F1-induced G1 checkpoint to regulate cell cycle progression" Oncogene, 2009, vol. 28, pp. 140-145.

Seton-Rogers et al. "Cooperation of the ErbB2 receptor and transforming growth factor β in induction of migration and invasion in mammary epithelial cells" Proc Natl Acad Sci, 2004, vol. 101, pp. 1257-1262.

Shi et al. "Micro RNA 145 Targets the Insulin Receptor Substrate-1 and Inhibits the Growth of Colon Cancer Cells*" J Biol Chem, 2007, vol. 282, pp. 32582-32590.

Shin et al. "A single lentiviral vector platform for microRNA-based conditional RNA interference and coordinated transgene expression" Proc Natl Acad Sci, 2006, vol. 103, pp. 13759-13764.

Song et al. Transcriptional mechanism for the paired miR-433 and miR-127 genes by nuclear receptors SHP and ERRγ Nucl Acid Res, 2008, vol. 36, pp. 5727-5735.

Stahl et al. "Deregulated Akt3 Activity Promotes Development of Malignant Melanoma" Cancer Res, 2004, vol. 64, 7002-7010.

Walden et al. "Distinct Expression of Muscle-Specific MicroRNAs (myomirs) in Brown Adipocytes" J Cell Physiol, 2008, vol. 218, pp. 444-449.

Wong et al. "Mature miR-184 as Potential Oncogenic microRNA of Squamous Cell Carcinoma of Tongue" Clin Cancer Res, 2008, vol. 14, pp. 2588-2592.

\* cited by examiner

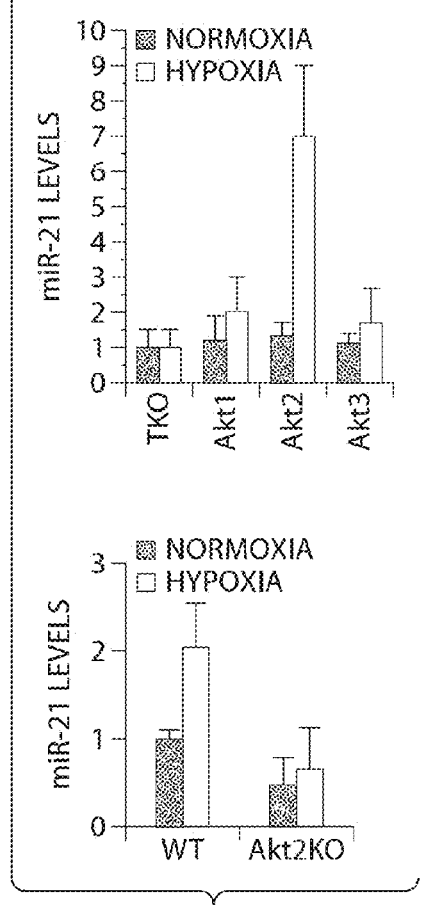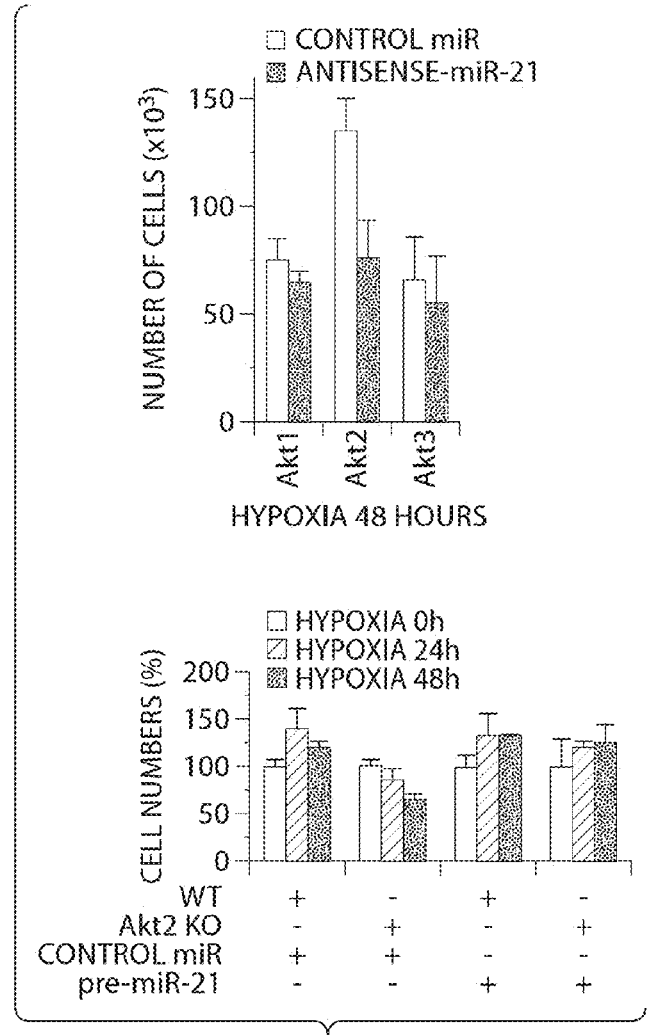
Figure 27A                    Figure 27B

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:

-continued

```
<223> OTHER INFORMATION: The nucleic acid was designed and synthesized

<400> SEQUENCE: 1
ttcaaaccca tagtggttgc t                                              21

<210> SEQ ID NO 2
<211> LENGTH: 21
<212> TYPE: DNA
<213> ORGANISM: Artificial Sequence
<220> FEATURE:
<223> OTHER INFORMATION: The nucleic acid was designed and synthesized

<400> SEQUENCE: 2
tgggagatac caaaccaact g                                              21

<210> SEQ ID NO 3
<211> LENGTH: 18
<212> TYPE: DNA
<213> ORGANISM: Artificial Sequence
<220> FEATURE:
<223> OTHER INFORMATION: The nucleic acid was designed and synthesized

<400> SEQUENCE: 3
caagaggcgc aaacaagc                                                  18

<210> SEQ ID NO 4
<211> LENGTH: 20
<212> TYPE: DNA
<213> ORGANISM: Artificial Sequence
<220> FEATURE:
<223> OTHER INFORMATION: The nucleic acid was designed and synthesized

<400> SEQUENCE: 4
ggttggcaat accgtcatcc                                                20

<210> SEQ ID NO 5
<211> LENGTH: 20
<212> TYPE: DNA
<213> ORGANISM: Artificial Sequence
<220> FEATURE:
<223> OTHER INFORMATION: The nucleic acid was designed and synthesized

<400> SEQUENCE: 5
tgcccagaaa atgaaaaagg                                                20

<210> SEQ ID NO 6
<211> LENGTH: 19
<212> TYPE: DNA
<213> ORGANISM: Artificial Sequence
<220> FEATURE:
<223> OTHER INFORMATION: The nucleic acid was designed and synthesized

<400> SEQUENCE: 6
ctggggtatt gggggcatc                                                 19

<210> SEQ ID NO 7
<211> LENGTH: 20
<212> TYPE: DNA
<213> ORGANISM: Artificial Sequence
<220> FEATURE:
<223> OTHER INFORMATION: The nucleic acid was designed and synthesized

<400> SEQUENCE: 7
gagaactttg ccgttgaagc                                                20

<210> SEQ ID NO 8
```

```
<211> LENGTH: 20
<212> TYPE: DNA
<213> ORGANISM: Artificial Sequence
<220> FEATURE:
<223> OTHER INFORMATION: The nucleic acid was designed and synthesized

<400> SEQUENCE: 8
ctaacggtgg atgtccttcg                                               20

<210> SEQ ID NO 9
<211> LENGTH: 20
<212> TYPE: DNA
<213> ORGANISM: Artificial Sequence
<220> FEATURE:
<223> OTHER INFORMATION: The nucleic acid was designed and synthesized

<400> SEQUENCE: 9
cttcgagctc atcctcatgg                                               20

<210> SEQ ID NO 10
<211> LENGTH: 20
<212> TYPE: DNA
<213> ORGANISM: Artificial Sequence
<220> FEATURE:
<223> OTHER INFORMATION: The nucleic acid was designed and synthesized

<400> SEQUENCE: 10
tctgcttggg gtccttctta                                               20

<210> SEQ ID NO 11
<211> LENGTH: 8
<212> TYPE: DNA
<213> ORGANISM: Artificial Sequence
<220> FEATURE:
<223> OTHER INFORMATION: The nucleic acid was designed and synthesized

<400> SEQUENCE: 11 tgacgcac                                                             8

<210> SEQ ID NO 12
<211> LENGTH: 10
<212> TYPE: DNA
<213> ORGANISM: Artificial Sequence
<220> FEATURE:
<223> OTHER INFORMATION: The nucleic acid was designed and synthesized

<400> SEQUENCE: 12
gaaaattccc                                                          10

<210> SEQ ID NO 13
<211> LENGTH: 8
<212> TYPE: DNA
<213> ORGANISM: Artificial Sequence
<220> FEATURE:
<223> OTHER INFORMATION: The nucleic acid was designed and synthesized

<400> SEQUENCE: 13 tgacatct                                                             8

<210> SEQ ID NO 14
<211> LENGTH: 36
<212> TYPE: DNA
<213> ORGANISM: Artificial Sequence
```

-continued

```
<220> FEATURE:
<223> OTHER INFORMATION: The nucleic acid was designed and synthesized

<400> SEQUENCE: 14
actgatgttg actgttgaat ctcatggcaa caccag                                    36
```

COMPOSITIONS AND METHODS FOR DIAGNOSIS AND PROGNOSIS OF CANCER AND PROGRESSION, AND FOR SCREENING ANTI-CANCER AGENTS

RELATED APPLICATIONS

This application claims the benefit of PCT application PCT/US2010/029804 filed Apr. 2, 2010, which claims of benefit of U.S. provisional application Ser. No. 61/211,726 filed Apr. 2, 2009 and U.S. provisional application Ser. No. 61/212,717 filed Apr. 14, 2009, which are hereby incorporated by reference herein in their entireties.

GOVERNMENT SUPPORT

This invention was made with government support under grants CA057436 and CA107486 awarded by the National Institutes of Health. The government has certain rights in the invention.

TECHNICAL FIELD

Compositions and methods for diagnosing and prognosing cancer appearance and development related to miRNA species, particularly Akt-1, -2 and -3 imbalances, and methods for screening potential agents that alter these imbalances are provided.

BACKGROUND

Akt proteins are serine-threonine protein kinases characterized by activation of phosphorylation at two sites ($Thr^{308}$ and $Ser^{473}$) through a phosphatidylinositol 3-kinase (PI3K)-dependent process. Specifically, Akt proteins refer to growth factor signals and other stimuli that activate PI3K and promote accumulation of D3-phosphorylated phosphoinositides at the plasma membrane. The interaction of these phosphoinositides with the pleckstrin homology (PH) domain of Akt promotes the translocation of the kinase to the plasma membrane, for phosphorylation by PI3K-dependent kinase-1 (PDK1) at $Thr^{308}$ and by mTOR (mammalian target of rapamycin) complex-2 (TORC2) at $Ser^{473}$ (Bellacosa et al., 1991 Science 254: 274-277; Franke et al., 1995 Cell 81: 727-736; Manning et al., 2007 Cell 129: 1261-1274).

Akt is linked with the induction and progression of human cancer (Altomare et al., 2005 Oncogene 24: 7455-7464). However, there are three Akt isoforms and information regarding their specific oncogenic activities is limited. The Akt1 and Akt2 isoforms appear to play different roles in mammary adenocarcinomas induced in mice by transgenes encoding the oncoproteins polyoma middle T and ErbB2 (also known as Neu), both of which activate the PI3K-Akt pathway. Ablation of Akt1 inhibits—whereas ablation of Akt2 accelerates—tumor induction and growth by both polyoma middle T and ErbB2 (Maroulakou et al., 2007 Cancer Res. 67: 167-177; Ju et al., 2007 Proc. Natl. Acad. Sci. U.S.A. 104: 7438-7443). However, the tumors developing in the Akt1 knockout mice are more invasive than the tumors developing in Akt2 knockout and wild-type mice (Maroulakou et al., 2007 Cancer Res. 67: 167-177). Ablation of Akt1 may also enhance tumor invasiveness, a process separate from and independent of tumor induction and growth (Chiang et al., 2008 N. Engl. J. Med. 359: 2814-2823). These findings were consistent with observations showing that Akt1 knockdown promotes migration and invasiveness of human mammary epithelial cells in culture (Irie et al., 2005 J. Cell Biol. 171:1023-1034; Yoeli-Lerner et al., 2005 Mol. Cell 20: 539-550; Liu et al., 2006 Proc. Natl. Acad. Sci. U.S.A. 103: 4134-4139), perhaps by promoting epithelial-mesenchymal transition (EMT), a process that plays important roles in both development and oncogenesis. During EMT, epithelial cells acquire a mesenchymal phenotype characterized by the loss of intercellular junctions and increased cell migration. On the molecular level, cells undergoing EMT decrease the abundance of epithelial cell-specific proteins, such as E-cadherin, and increase the abundance of mesenchymal cell-specific proteins, such as vimentin. The developmental switch characteristic of EMT renders tumor cells undergoing this process more invasive and metastatic. Thus, inhibition of individual Akt isoforms may have both desirable and undesirable effects during oncogenesis.

MicroRNAs are a class of molecules that regulate gene expression by various mechanisms and play important roles in oncogenesis (Calin et al., 2005 Proc. Natl. Acad. Sci. U.S.A. 101: 11755-11760; Lu et al., 2005 Nature 435: 834-838). Like conventional oncogenes and tumor suppressor genes, microRNAs may either promote or inhibit oncogenesis. Also, like conventional cancer genes, their expression is selectively increased or decreased in various human and animal tumors. The selective deregulation of microRNA gene expression may be due to deletions, amplifications, or mutations targeting the microRNAs themselves or their regulatory sequences, as well as to dysregulation of transcription factors and epigenetic regulators targeting the genes encoding them (Croce, 2009 Nat. Rev. Genet. 10: 704-714). Understanding the regulation and functional activities of individual microRNA families in cancer and other human diseases could thus lead to new opportunities for therapeutic intervention.

Cancer remains a major public health problem among adults, and is the leading disease-related cause of death in children. Therapeutic agents in use are limited by substantial side effects, including chemotherapeutic agents that cause fatigue and nausea, and radiation with other iatrogenic effects. There remains a need for novel methods of detecting and novel compositions and methods for treating cancers, and for early stage prognosis of cancer.

SUMMARY

An aspect of the invention herein provides a method for prognosing or diagnosing a potential cancer and progression of an existing cancer in a patient by analyzing Akt isoform imbalance including:

measuring an expression profile of a plurality of microRNA (miRNA) species related to Akt isoform expression in a sample from the patient, and comparing the profile from the patient with that of a normal subject, such that measuring the expression profile includes at least one of analyzing amount of miRNA species using: an array format having a plurality of miRNA sequences, each species at a known location on a substrate; and real-time PCR; thereby obtaining a microRNA tumor profile;

such that a difference in the Akt isoform expression profile of the sample from the patient and from the normal subject is a prognosis or diagnosis of the potential cancer or an indication of progression of the existing cancer.

In related embodiments, the miRNA is an miR-200 miRNA, for example, the miR-200 miRNA is at least one selected from the group of: miR-200a, miR-200b, and miR-200c. In alternative embodiments, the miRNA is an miR-34 or an miR-21. For example, the miR-34 is at least one selected from the group of: miR-34a, miR34b, and miR-34c.

In an embodiment of the method, the sample includes a cell from a biopsy of the patient. In a related embodiment the method further includes culturing cells ex vivo and screening compounds in a library contacted with aliquots of resulting cultured cells and control normal subject cells, to obtain a potential inhibitor that restores Akt expression balance and thereby inhibits the cancer. For example, the cells are epithelial. In related embodiments, the sample includes at least one selected from the group of: blood, cerebrospinal fluid, mammary glands, prostate gland, lung, bladder, cervix, and colorectal.

The method in a related embodiment further includes measuring decreased expression of at least one miRNA associated with at least one transcription factor, and prognosing cancer or cancer progression. For example, the transcriptional factor is selected from at least one IGF1 and TGFβ.

An embodiment of the method further includes measuring upregulation of expression of at least one miRNA associated with hypoxic cells or a hypoxic tumor. For example, the miRNA is miR-21. A related embodiment further includes measuring miR-21 induction in Akt-2 expressing cells. A related embodiment further includes measuring selective activation and binding of CREB/CBP and NF-κB to an miR-21 enhancer. A related embodiment further includes measuring decreased expression of the miR-21, for example, measuring decreased expression of miR-21 and increased expression of H1F1 in tumors. A related embodiment further includes measuring levels of H1F1 and correlating the H1F1 levels with oxygen status of tumors, such that measuring increased expression of H1F1 correlates with hypoxic tumors and decreased expression of H1F1 correlates with normoxic tumors.

A related embodiment further includes measuring decreased expression of at least one miRNA associated with at least one of: Zeb1, Zeb2, PTEN, PDCD4, SHIP2, Spry1, and a protein that phosphorylates a site in an Akt-targeted motif, and prognosing cancer or cancer progression in the patient. A related embodiment further includes measuring decreased expression of at least one miRNA associated with E-cadherin, and prognosing cancer or cancer progression in the patient. A related embodiment further includes measuring a decreased expression of at least one miRNA associated with cells for an epithelial-mesenchymal-transition (EMT) phenotype, and prognosing cancer or cancer progression in the patient. A related embodiment further includes measuring decreased expression of at least one miRNA selected from the group of miR-200a, miR-200b, and miR-200c, and prognosing cancer or cancer progression in the patient. A related embodiment further includes measuring increased expression of at least one miRNA selected from the group of miR-34a, miR-34b, miR-34c and miR-21, and prognosing cancer or cancer progression in the patient. A related embodiment further includes including measuring decreased expression of at least one miRNA associated with an imbalance of Akt isoforms, prognosing cancer or cancer progression in the patient. A related embodiment further includes measuring decreased expression of miRNA species associated with an imbalance of expression of at least one of Akt1 and Akt2, and prognosing cancer or cancer progression in the patient. A related embodiment further includes including measuring miRNA species associated with reduced expression of Akt1, and prognosing cancer or cancer progression in the patient. A related embodiment further includes measuring increased expression of miRNA species associated with imbalance of at least one of Akt1, Akt2 and Akt3, and the prognosing cancer or cancer progression in the patient. A related embodiment further includes further including measuring no difference in patient Akt amounts and normal subject Akt amounts, and correlating with at least one selected from: cancer, progression of cancer, metastasis, invasiveness, enlargement of tumor size, regression of tumor size, disappearance of tumor, no evidence of disease, and remission.

A related embodiment further includes determining cell motility of the sample, and prognosing increased motility with at least one of invasiveness and metastasis in the patient.

An aspect of the invention herein provides a method of screening a library of compounds for an anti-cancer agent that downregulates a pathway associated with cancer, the method including:

obtaining cells from a cancer patient having an alteration in amount of expression of an microRNA (miRNA) species that downregulates a cancer;

contacting the cells from the patient with at least one compound; and analyzing amount of miRNA having a nucleotide sequence associated with regulation of an Akt isoform protein or an Akt isoform protein inhibitor, and measuring upregulating by the compound of the amount of at least one of the miRNA species, thereby identifying the at least one compound in the library as the anti-cancer agent.

For example, the miRNA is selected from at least one of miRNA-200, miRNA-34 and miRNA-21. For example, the Akt isoform is selected from at least one of Akt1, Akt2 and Akt3. For example, the Akt isoform inhibitor inhibits at least one selected from the group of Akt1, Akt2 and Akt3.

A related embodiment further includes further includes measuring a substantially unchanged amount of Akt isoform compared with a control not so contacted and otherwise identical.

A related embodiment further includes measuring downregulation of the Akt isoform. A related embodiment further includes further includes measuring upregulation of the Akt isoform. For example, the miR-200 miRNA includes at least one selected from the group of: miR-200a, miR-200b, and miR-200c. For example, the miRNA-34 includes at least one selected from the group of: miR-34a, miR-34b, and miR-34c A related embodiment further includes cells that were taken from a biopsy sample of the subject or patient. The term "subject" herein means a vertebrate animal, generally a warm-blooded vertebrate animal, for example a mammal including a human. A patient is a human or other mammal in need of prognosis or diagnosis, for example, of a tumor or cancer.

A related embodiment further includes method prior to contacting, culturing the cells ex vivo. For example, the cells are epithelial. In alternative embodiments, the sample includes at least one selected from blood, cerebrospinal fluid, mammary glands, prostate gland, and biopsy of lung, bladder, cervix, and colorectal tissues.

An aspect of the invention provides a kit for prognosing or diagnosing a cancer or potential cancer in a patient including: a container; a plurality of miRNA species such that each miRNA is located at a discrete identifiable address on an array, the miRNA species including at least one nucleotide sequence that downregulates expression of at least one gene; and instructions for use. For example, the Akt in includes at least one of Akt1, Akt2 and Akt3. A related embodiment further includes the kit having at least one siRNA. For example, the siRNA includes a nucleotide sequence encoding at least one Akt isoform. A related embodiment of the kit further includes at least one siRNA that is a control having a nucleotide sequence not associated with regulation of Akt isoforms. For example, the Akt isoform includes at least one of Akt1, Akt2 and Akt3. A related embodiment further includes a positive control. For example, the miR-200 includes at least one of: miR-200a, miR-200b, and miR-200c. For example, the miR-34 includes at least one of: miR-34a, miR-34b, and miR-34c.

An aspect of the invention herein provides a method for formulating a composition for treating a cancer patient, the method including identifying an agent or an inhibitor having an activity of regulating miRNA species associated with expression of Akt isoform proteins in the patient, providing the agent or the inhibitor in an effective dosage to formulate the composition for reducing or preventing growth of cancer cells, contacting the patient with the composition and measuring at least one miRNA expression profile; and regression of tumor size or disappearance of tumor.

For example, the composition effectively downregulates at least one Akt isoform selected from the group of Akt1, Akt2 and Akt3. For example, the composition effectively regulates miRNAs associated with at least one of Zeb1, Zeb2, PTEN, PDCD4, SHIP2, Spry1, and a protein that phosphorylates a site of an Akt-targeted motif. For example, the inhibitor is selected from at least one of the group including: inhibitors of the PI3K/Akt and dual PI3K and mTOR inhibitors BEZ235, BGT226, XL765, SF1126, GSK1059615; PI3K inhibitors XL147, PX866, GDC0941, BKM120, CAL101 targets p110d; Akt inhibitors Perifosane, GSK690693, VQD002, MK2206; inhibitors of mTOR catalytic site OSI027, and AZD8055, and miRNA-200, miRNA-34 and miRNA-21. These molecules serve as therapeutic molecules, or alternatively, as positive controls for identifying novel agents. For example, the method further includes, prior to contacting, measuring mirNA expression profile and phosphorylation of the Akt isoform proteins in the patient. For example, the method further includes, after contacting, measuring miRNA expression profile and phosphorylation of Akt isoform proteins in the patient. For example, the method includes rationally designing a protocol for selecting the composition for treating the cancer in the patient.

Accordingly, an aspect of the invention herein provides a method for treating a cancer patient, the method including:
identifying an agent or an inhibitor regulating miRNA species associated with expression of Akt isoform proteins in the patient,
formulating the agent or the inhibitor in an effective dose thereby preparing a composition for reducing or preventing growth of cancer cells,
contacting the patient with the composition and measuring regression of tumor size or disappearance of tumor.

For example, the composition effectively downregulates at least one Akt isoform selected from the group of Akt1, Akt2 and Akt3. For example, the composition effectively regulates miRNAs associated with at least one of Zeb1, Zeb2, PTEN, PDCD4, SHIP2, Spry1, and a protein that phosphorylates a site of an Akt-targeted motif.

An aspect of the invention herein provides a cell line expressing at least first Akt isoform protein and suppressing at least second Akt isoform protein, the cell line including a vector containing a nucleic acid sequence encoding an siRNA abolishing or suppressing expression of the second Akt isoform protein. For example, the first Akt isoform protein is selected from Akt1, Akt2, Akt3, and combinations thereof. For example, the second Akt isoform protein is selected from Akt1, Akt2, Akt3, and combinations thereof.

BRIEF DESCRIPTION OF DRAWINGS

FIG. 1A shows a method to obtain cells that express different Akt isoforms.

FIG. 1B shows photographs of Western blots of cell lysates probed with antibody specific for a myc tag or with antibodies specific for Akt1, Akt2, or Akt3. Tubulin was used as a loading control.

FIG. 1C shows results obtained with RNA from cell lysates harvested before and after IGF1 treatment screened with a 365 microRNA array.

FIG. 3A is a set of immunoblots showing that IGF1 treatment induces the phosphorylation of all Akt isoforms at $Ser^{473}$ and $Thr^{308}$ (in Akt1 or the equivalent sites in Akt2 and Akt3) in murine lung fibroblasts engineered to express Akt1, Akt2, or Akt3. After overnight serum starvation, cells were treated with IGF1 (50 ng/ml) for 10 minutes, and cell lysates were analyzed by Western blot. Tubulin was used as a loading control.

FIG. 3B is a set of heatmaps showing differentially expressed microRNAs in untreated and IGF1-treated (1, 4, and 16 hours) fibroblasts carrying individual Akt isoforms. Lighter shade of gray indicates upregulation, and darker shade of gray indicates downregulation.

FIG. 3C is a diagram showing overlap between the microRNA signatures of IGF1-treated (16 hours) Akt1, Akt2, Akt3, and TKO fibroblasts.

FIG. 3D is a set of bar graphs showing the abundance of family members measured by real-time RT-PCR 1, 4, and 16 hours after IGF1 treatment. MicroRNA abundance before the IGF1 treatment was set to 0. MiR-200 family members were down-regulated after IGF1 treatment only in Akt2-expressing fibroblasts.

FIG. 3E is a set of bar graphs showing downregulation of miR-200a and miR-200c in Akt2-expressing MEFs. The expression of miR-200 family members was measured at 16 hours after IGF1 treatment by real-time RT-PCR. The examples were performed in triplicate and data are presented as mean±SD.

FIG. 5A shows quantitative differences in downregulation of miR-149 by IGF1, in TKO and Akt1, Akt2 or Akt3-expressing immortalized lung fibroblasts.

FIG. 5B shows quantitative and qualitative differences in the regulation of miR-27a, miR-20a, miR-16, miR-34a, miR-433 and miR-10b by IGF1, in immortalized lung fibroblasts engineered to express Akt1, Akt2 and Akt3. The data in A and B validated the microRNA microarray data and confirmed the dynamics of microRNA expression during IGF1 treatment in cells expressing different Akt isoforms

FIG. 9A shows Akt phosphorylation in MCF10A mammary epithelial cells.

FIG. 9B shows that murine lung fibroblasts expressed each of the three Akt isoforms.

FIG. 11A shows knockdown of Akt1 and Akt2 in MCF10A cells. Western blots of cell lysates after transfection of Akt1, Akt2, or Akt1 and Akt2 siRNAs probed with the indicated antibodies.

FIG. 11B is a set of bar graphs showing that TGFβ synergizes with Akt1 knockdown to increase Zeb1 abundance. Zeb1 abundance was measured by real-time PCR in cells transfected with the indicated siRNAs and treated with TGFβ.

FIG. 11C shows that Akt1 knockdown promotes EMT. The upper panel shows that the knockdown synergizes with TGFβ to decrease E-cadherin abundance. The photographs of Western blots of lower panel show lysates of cells transfected with the indicated siRNAs, treated with TGFβ and probed with antibodies against E-cadherin and β-actin. The knockdown synergized with TGFβ to stimulate cell migration. The lower panel is a bar graph showing that cell migration of TGFβ stimulated cells transfected with the indicated siRNAs.

FIG. 11D upper panel shows chromosomal map of the miR-200 microRNA family. The lower panel is a set of bar graphs showing that the knockdown was synergized with TGFβ to decrease abundance of miR-200a and miR-200c. MicroRNA abundance was measured by real-time PCR.

FIG. 11E shows that the abundance of miR-200c and the mRNA encoding E-cadherin in cells transfected with Akt1 siRNA returned to pre transfection values as the effect of the siRNA on Akt1 abundance waned. Time course analysis by real-time RT-PCR in cells transfected with Akt1 siRNA and treated with TGFβ.

FIG. 12A shows that Zeb2, similar to Zeb1 (FIG. 3B), was increased in response to Akt1 knockdown and TGFβ treatment. Knockdown of Akt2 did not induce Zeb2 and abolished the effects of the Akt1 knockdown. Real-time RT-PCR analysis was used to measure abundance of mRNA encoding Zeb2 in untreated and TGFβ-treated (20 ng/ml) MCF10A cells transfected with a control siRNA, or siRNAs targeting Akt1, Akt2, or Akt1 plus Akt2 (50 nM). The induction of Zeb2 was more robust in cells in which Akt1 was knocked down.

FIG. 12B shows that knockdown of Akt1 decreased the abundance of the mRNA encoding E-cadherin, and the knockdown of Akt2 did not. Moreover, the knockdown of Akt2 abolished the effects of the Akt1 knockdown. Expression of E-cadherin in untreated and TGFβ-treated MCF10A cells transfected with control, Akt1, Akt2, or Akt1 plus Akt2 siRNAs was examined by real-time RT-PCR. The examples were performed in triplicate and data are presented as mean±SD.

FIG. 13A shows cell motility measured using transwell migration assays on BT474 cells.

FIG. 13B shows cell motility measured using transwell migration assay on MCF-7 cells 24 h after transfection with control, Akt1, Akt2, or Akt1 and Akt2 siRNAs. The examples were performed in triplicate and data are presented as mean±SD.

FIG. 16A and FIG. 16B show that overexpression of miR200a or miR-200c inhibited upregulation of Zeb1 and Zeb2 in MCF10A cells transfected with Akt1 siRNA and treated with TGFβ.

FIG. 16C shows that overexpression of miR-200a or miR-200c inhibited downregulation of E-cadherin in MCF10A cells transfected with Akt1 siRNA and treated with TGFβ. Abundance of the miRNAs encoding Zeb1, Zeb2, and E-cadherin was measured by real-time PCR in lysates of TGFβ-treated MCF10A cells transfected with the indicated siRNAs and compared with the miRNAs of the control cells.

FIG. 16D shows that overexpression of miR-200a or miR-200c inhibited cell migration in MCF10A cells transfected with Akt1 siRNA and treated with TGFβ. Cell migration was measured in TGFβ-stimulated MCF10A cells 24 hours after transfection with the indicated siRNAs. Assays were performed in triplicate and data are presented as mean±SD.

FIG. 17A shows MCF10A cells transfected with control siRNA or siRNAs for Akt1, Akt2, or Akt1 and Akt2 that were cultured for 6 days in suspension in the presence or absence of recombinant TGFβ (20 ng/ml). The bar graph shows the number of mammospheres per 1000 plated cells in each culture (mean±SD) at the end of the procedure.

FIG. 17B shows phase-contrast images (low and high magnification) of mammospheres described in FIG. 17A. Scale bar, 100 mm.

FIG. 17C shows replating efficiency of mammospheres derived from MCF10A cultures transfected with siRNA control, and siRNAs for Akt1, Akt2, and Akt1 plus Akt2.

FIG. 17D is a set of bar graphs showing that primary mammospheres of MCF10A cells transfected with Akt1 siRNA have less miR-200a, miR-200c, and E-cadherin than MCF10A cells transfected with control, Akt2, or Akt1 plus Akt2 siRNAs. MicroRNA and E-cadherin expression (lower graph) were measured in 6-day mammospheres by realtime RT-PCR. Assays were performed in triplicate, and data are presented as mean±SD.

FIG. 20A is a table with data showing that mammary adenocarcinomas developing in MMTV-cErbB2/Akt1$^{-/-}$ mice were more invasive than mammary adenocarcinomas arising in MMTV-cErbB2/WT and MMTV-cErbB2/Akt2$^{-/-}$ mice.

FIG. 20B shows that MMTV-cErbB2/Akt1$^{-/-}$ mammary adenocarcinomas had lower abundance of miR-200 microRNAs than did mammary adenocarcinomas developing in MMTV-cErbB2/Akt1$^{+/+}$ and MMTV-cErbB2/Akt2$^{-/-}$ mice. MicroRNA abundance was measured by real-time RT-PCR.

FIG. 20C shows that MMTVcErbB2/Akt1$^{-/-}$ mammary adenocarcinomas had more abundant Zeb1 and vimentin and less abundant E-cadherin than did mammary adenocarcinomas developing in MMTV-cErbB2/Akt1$^{+/+}$ and MMTV-cErbB2/Akt2$^{-/-}$ mice. Western blots of primary tumor cell lysates were probed with the indicated antibodies.

FIG. 20D is a set of photographs showing in situ hybridization (for microRNA) and immunofluorescence (for E-cadherin) which confirmed that MMTV-cErbB2/Akt1$^{-/-}$ mammary adenocarcinomas had low abundance of miR-200 family members and E-cadherin (microphotographs at 40× magnification). Scale bar, 10 μm.

FIG. 21A shows microphotographs at 10× magnification, of Hematoxylin and Eosin (H and E) stained sections of a primary tumor on the upper panel; in situ hybridization of a section from the same tumor, probed with scrambled miR on the left middle panel, or miR-200c on the right middle panel; DAPI (4',6-diamidino-2phenylindole) and E-cadherin-stained tumor sections on the left and right lower panels, respectively. Comparison of the in situ hybridization of scrambled miR and miR200c showed that miR-200c hybridizes specifically with MMTV-cErbB2-induced adenocarcinomas.

FIG. 21B shows microphotographs at 40× magnification of the H and E stained on the upper panel, of miR-200c-hybridized and DAPI-stained on the middle panel, and of E-cadherin-stained section on the lower panel, of an MMTV-cErbB2-induced mammary adenocarcinoma.

FIG. 21C shows microphotographs at 100× magnification of overlapping images of a section of a primary MMTVcErbB2-induced mammary adenocarcinoma, hybridized with miR-200c and stained with DAPI and E-cadherin. E-cadherin staining was localized at the plasma membrane, and miR-200c was localized in the cytoplasm.

FIG. 23A shows abundance of Akt1, Akt2, and E-cadherin mRNAs and microRNAs measured by real-time RT-PCR in primary and metastatic tumors. The data represent triplicate measurements from each RNA sample normalized to GAPDH. Gray lines connect each primary tumor with the corresponding metastatic tumor. Asterisks are used to mark two cases in which the ratio of Akt1 to Akt2 remained high in the metastatic tumor sample despite the fact that miR-200 and E-cadherin abundances were lower than in the primary tumor samples from the same patients. The indicated P value (P=0.013) was calculated with all tumors included. P values were calculated with a paired two-population Student's t test. The mean value for each set is shown as a horizontal black line.

FIG. 23B shows that plotting the Akt1/Akt2 ratio and the expression of miR-200a, miR-200c, and E-cadherin in the six metastatic tumor samples characterized by low Akt1/Akt2 ratios (FIG. 23A) showed an excellent correlation between these parameters. Spearman rank correlation coefficients and the P values (in parentheses) are shown on the lower panel.

FIG. 25A is a set of growth curves of triple Akt knockout lung fibroblasts and their derivatives expressing Akt1, Akt2 or Akt3, growing under normal culture conditions.

FIG. 25B is a Western blot photograph showing expression of p53 in triple Akt knockout lung fibroblasts, engineered to express Akt1, Akt2 or Akt3, before and after stimulation with IGF1.

FIG. 25C is a bar graph showing expression of miR-34a in triple Akt knockout cells and their derivatives expressing Akt1, Akt2 or Akt3, before and after stimulation with IGF1. (miR-34b and miR-34c exhibit a similar expression pattern).

FIG. 26A is a bar graph showing that numbers of Akt1, Akt2, or Akt3-expressing cells surviving under hypoxia. Cell number was quantified after 24 and 48 hours of growth under normoxic (normal level of oxygen) and hypoxic conditions. Data are expressed as mean±SD.

FIG. 26B is a bar graph showing numbers of Akt2$^{-/-}$ and Akt2$^{+/+}$ MEFs surviving under hypoxia. Cell number was quantified after 24 and 48 hours of growth under normoxic and hypoxic conditions. Data are expressed as mean±SD.

FIG. 26C is a bar graph showing ratios of live cancer cells in cultures exposed to hypoxia and cultures maintained in normoxia. Cells transduced with Akt2 or Akt1 shRNA were quantified at the indicated time points. Data are expressed as mean of the numbers of live cells under hypoxic divided by the ones under normoxia±SD.

FIG. 26D is a set of flow cytometry histograms and a bar graph showing numbers of apoptotic cells after exposure of the lung fibroblasts to hypoxia. TUNEL assay was performed on Akt1, Akt2, or Akt3-expressing cells cultured under hypoxic and normoxic conditions. Left panel shows representative data and right panel shows cumulative data from three procedures. Data are expressed as mean±SD.

FIG. 26E is a set of flow cytometry histograms and a bar graph showing cell cycle analysis of the same cells exposed to hypoxia. Flow cytometry was performed on ethidium bromide-stained cell nuclei, 24 hours after exposure to hypoxia. Left panel shows representative data and right panel shows cumulative data of cells in the S phase from four procedures. Data are expressed as mean±SD.

FIGS. 27A-27D is a set of bar graphs and flow cytometry histograms showing the upregulation of miR-21 in Akt2-expressing cells upon oxygen deprivation controls their resistance to hypoxia FIG. 27A is a set of bar graphs showing upregulation of miR-21 was validated by qRT-PCR in immortalized triple Akt knockout lung fibroblasts and their derivatives expressing Akt1, Akt2, or Akt3, and Akt2$^{-/-}$ and Akt2$^{+/+}$ MEFs 24 hours after exposure to hypoxia. Values are expressed as mean relative miR-21 expression levels±SD.

FIG. 27B is a set of bar graphs showing effect of miR-21 expression on cell sensitivity to hypoxia. Cell number was quantified after 48 hr of culture under hypoxia. Cells were transiently transfected with negative control miR, antisense miR-21 (anti-miR-21) or miR-21 precursor (pre-miR-21). Data are expressed as mean±SD.

FIG. 27C is a set of flow cytometry histograms and a bar graph showing numbers of apoptotic cells after exposure of the lung fibroblasts to hypoxia. TUNEL assay was performed on Akt1, Akt2, or Akt3-expressing cells transfected with anti-miR-21 and cultured under hypoxic conditions for 24 hours. Histogram on the left panel shows representative data and a bar graph on the right panel show cumulative data from three procedures. Data are expressed as mean±SD.

FIG. 27D is set of flow cytometry histograms showing cell cycle analysis of the same cells exposed to hypoxia. Nuclear ethidium bromide-staining and flow cytometry was performed on cells, transfected with anti-miR-21 and cultured under hypoxic conditions for 24 hours.

FIG. 28A is a photograph of immunoblots showing PTEN protein levels and Akt activity in immortalized triple Akt knockout lung fibroblasts and their derivatives expressing Akt1, Akt2, or Akt3 upon oxygen deprivation. Cell lysates were blotted with antibodies specific to PTEN, phospho-Akt (Ser473 and Thr308), phospho-Akt substrate, and antibody specific to a-tubulin was used as a loading control.

FIG. 28B is a set of photographs of immunoblots showing PTEN protein levels and Akt activity in Akt2$^{-/-}$ and Akt2$^{+/+}$ MEFs upon oxygen deprivation. Cell lysates were blotted with antibodies specific to PTEN, phospho-Akt (Ser473 and Thr308), Akt phosphosubstrate, phospho-Gsk3, phospho-mTOR, phospho-4EBP1, and antibody specific to a-tubulin was used as a loading control.

FIG. 28C is a set of photographs of immunoblots showing effect of miR-21 alterations on PTEN protein levels and Akt activation in Akt1-, and Akt2-expressing cells, and in Akt2$^{-/-}$ and Akt2$^{+/+}$ MEFs growing under hypoxia. Upper panel shows that Akt1-, and Akt2-expressing cells transfected with control-miR or anti-miR-21 and lower panel shows that Akt2$^{-/-}$ and Akt2$^{+/+}$ MEFs and transfected with control-miR or pre-miR-21 were cultured under hypoxic conditions for 24 hours. Cell lysates were blotted with antibodies specific to PTEN and phospho-Akt (Ser473) antibodies, and antibody specific to a-tubulin was used as a loading control.

FIG. 28D is a photograph of immunoblots and a set of bar graphs showing effect of Akt2 expression on PTEN protein levels and Akt activation in Akt1-expressing cells growing under hypoxia. Immortalized triple Akt knockout lung fibroblasts and their derivatives expressing myc.Akt1, HA.Akt2 or both, were cultured under hypoxia for 24 hours. Cell lysates were immunoprecipitated using anti-myc antibody (for Akt1) or anti-HA beads (for Akt2) and blotted with anti-phospho-Akt (Ser473 and Thr308) antibodies. Anti-myc and anti-HA antibodies were used as loading controls.

FIG. 29A shows PTEN, PDCD4 and Spry1 protein levels in immortalized triple Akt knockout lung fibroblasts and their derivatives expressing Akt1, Akt2, or Akt3 upon oxygen deprivation. Cell lysates were blotted with antibodies specific to PTEN, PDCD4, Spry1, and antibody specific to a-tubulin was used as a loading control.

FIG. 29B shows PTEN, PDCD4 and Spry1 protein levels in Akt2$^{-/-}$ and Akt2$^{+/+}$ MEFs upon oxygen deprivation. Cell lysates were blotted with antibodies specific to PTEN, PDCD4, Spry1, and antibody specific to a-tubulin was used as a loading control.

FIG. 29C shows effect of miR-21 alterations on PDCD4 and Spry1 protein levels and ERK1/2 phosphorylation in Akt1-, and Akt2-expressing cells growing under hypoxia. Akt1-, and Akt2-expressing cells transfected with control-miR or anti-miR-21 were cultured under hypoxic conditions for 24 hours. Cell lysates were blotted with antibodies specific to PDCD4, Spry1 and phospho-ERK1/2 (Thr202/Tyr204), and antibody specific to a-tubulin was used as a loading control.

FIG. 29D shows effect of miR-21 alterations on PDCD4 and Spry1 protein levels and ERK1/2 phosphorylation in Akt2$^{-/-}$ and Akt2$^{+/+}$ MEFs upon oxygen deprivation. MEFs transfected with control-miR or pre-miR-21 were cultured under hypoxic conditions for 24 hours. Cell lysates were blotted with antibodies specific to PDCD4, Spry1 and phospho-ERK1/2 (Thr202/Tyr204), and antibody specific to a-tubulin was used as a loading control.

FIGS. 30A and 3B are a photograph of immunoblots and a bar graph showing that combined downregulation of PTEN, PDCD4 and Sprouty1 in Akt1-expressing cells is sufficient to induce resistance to hypoxia FIG. 30A is a photograph of immunoblots showing controlled knockdown of PTEN, PDCD4 and Spry1 protein levels in Akt1-expressing cells upon oxygen deprivation. Akt1-expressing cells transfected with Control, PTEN, PDCD4 and Spry1 siRNAs alone or in combination and Akt2-expressing cells transfected with Control siRNA were cultured under hypoxic conditions for 24 hours. Cell lysates were blotted with antibodies specific to PTEN, PDCD4, Spry1, and antibody specific to a-tubulin was used as a loading control.

FIG. 31A is a schematic diagram of the promoter of miR-21. Cross-hatched boxes represent binding sites for CREB and NF-κB; stippled box represents miR-21 gene. The leftmost nucleotide sequence is a binding site for CREB indicated "CREB/" at residue −3536 (SEQ ID NO: 11). The next nucleotide sequence is a binding site for NF-κB at residue −1278 (SEQ ID NO: 12). The next nucleotide sequence is a binding site for CREB indicated "CREB//" at residue −43 (SEQ ID NO: 13). The nucleotide sequence of the transcribed portion of the miR-21 gene beginning at residue +1 is shown on the right (SEQ ID NO: 14).

FIG. 31B is a set of schematic diagrams and a bar graph showing miR-21 promoter activity in Akt1-, and Akt2-expressing cells cultured under hypoxic conditions for 24 hours. Left panel shows schematic diagrams of the reporter gene vectors carrying the full length promoter of miR-21 and right panel shows the point mutants and luciferase activity assay. Relative luciferase activity was calculated as the ratio of firefly/renilla activity and was set as 1 in Akt1-expressing cells under normoxia. Data are expressed as mean±SD.

FIG. 31E is a set of bar graphs showing chromatin immunoprecipitation for CBP and H3K9 acetylation in Akt1-, and Akt2-expressing cells growing under normoxic or hypoxic conditions. Left panel shows the fold enrichment of CBP and right panel the fold enrichment of H3K9Ac to the promoter of miR-21, before and after exposure to hypoxia as studied by real time PCR. Data are expressed as mean±SD.

FIG. 32A is a set of bar graphs showing expression of miR-21 and its targets in mammary adenocarcinomas in HIF-1a-expressing MMTV-PyMT/Akt$^{+/+}$, MMTV-PyMT/Akt1$^{-/-}$ and MMTV-Pymt/Akt2$^{-/-}$ mice. Relative miR-21 levels were measured by real time RT-PCR, U6 levels were used as control. Data are expressed as mean±SD (n=4-5 animals per group). Relative PTEN, PDCD4 and Spry1 protein levels were analyzed by western blot, intensity of the corresponding bands was quantified. a-Tubulin was used as a loading control. Data are expressed as mean±SD (n=4-5 animals per group).

FIG. 32B is a set of photomicrographs showing immunohistochemistry data for HIF-1a and in situ hybridization for miR-21 in tumors arising in MMTV-PyMT/Akt$^{+/+}$ and MMTV-Pymt/Akt2$^{-/-}$ mice.

FIG. 32C is a set of distribution plots showing expression of Akt2, miR-21 and PTEN in human ovarian carcinomas. Samples were classified into two groups expressing high and low HIF-1a and further analyzed for miR-21 and PTEN levels.

DETAILED DESCRIPTION

Figure 1A:
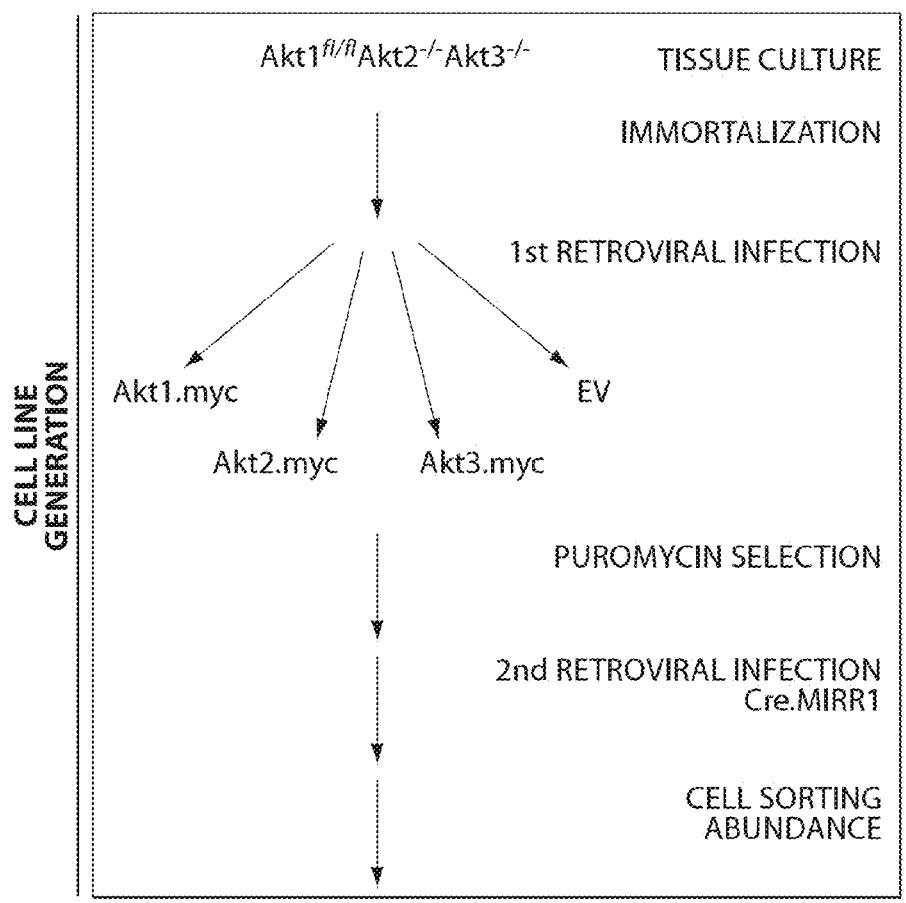
FIGS. 1A-1C are a drawing, a set of photographs of immunoblots and a photograph of a microarray showing strategy for generating lung fibroblasts according to abundance of different Akt isoforms and for the identification of IGF1-induced microRNAs.

Akt is known to play a role in human cancer, however, the relative contribution of its three isoforms to oncogenesis remains to be determined. Examples herein identify and characterize the downstream targets of Akt isoforms, which are shown herein to discriminate the beneficial from the detrimental effects of isoform-specific Akt inhibition. Each isoform was expressed individually in an Akt1$^{-/-}$/Akt2$^{-/-}$/Akt3$^{-/-}$ cell line. MicroRNA profiling of growth factor-stimulated cells showed unique microRNA signatures for cells with each isoform. Among the differentially regulated microRNAs, the abundance of the miR-200 family was decreased in cells bearing Akt2. Knockdown of Akt1 in transforming growth factor-β (TGFβ)-treated MCF10A cells also decreased the abundance of miR-200; however, knockdown of Akt2, or of both Akt1 and Akt2, did not. Furthermore, Akt1 knockdown in MCF10A cells promoted TGFβ-induced epithelial-mesenchymal transition (EMT) and a stem cell-like phenotype. Carcinomas developing in MMTV-cErbB2/Akt1$^{-/-}$ mice showed increased invasiveness because of miR-200 downregulation. Without being limited by any particular theory or mechanism, the ratio of Akt1 to Akt2 and the abundance of miR-200 and of the messenger RNA encoding E-cadherin in a set of primary and metastatic human breast cancers showed that in many cases, breast cancer metastasis may be under the control of the Akt-miR-200-E-cadherin axis. It is shown herein that induction of EMT is controlled by microRNAs the abundance of which depends on the balance between Akt1 and Akt2 rather than on the overall activity of Akt.

A set of microRNAs was shown to be differentially regulated by the three Akt isoforms in cells stimulated with insulin-like growth factor 1 (IGF1), a treatment that activates Akt. In addition, it was shown herein that a decrease in the abundance of the miR-200 microRNA family in cells in which the ratio of Akt1 to Akt2 was decreased promotes EMT and the acquisition of a stem cell-like phenotype in cultured cells, as well as in mouse and human tumors. Downregulation of the miR-200 microRNA family in these cells depends on the balance between Akt1 and Akt2 and does not depend on Akt activity per se.

The examples herein focus on the role of different Akt isoforms in regulation of microRNA gene expression in IGF1 and TGFβ-treated cells. A number of different microRNAs were shown to be differentially regulated by the different Akt isoforms, including members of the miR-200 microRNA family. Examples show that Akt1 and Akt2 had opposing activities on the expression of the miR-200 family, Akt1 as an activator and Akt2 as a repressor, and that the expression of miR-200 microRNAs depended upon the balance between Akt1 and Akt2, not overall Akt levels. Data show that selective inhibition of Akt1 leads to an invasive cancer stem cell-like phenotype, which was promoted by the downregulation of miR-200 microRNAs. Without being limited by any particular theory or mechanism of action an imbalance in the expression or activity of Akt1 and Akt2, not necessarily overall Akt levels influences the invasiveness and oncogenic potential of human carcinomas.

Akt is considered a high-priority therapeutic target (Dennis, in American Association for Cancer Research Annual Meeting Education Book (AACR, San Diego, Calif., 2008), pp. 24-35). Pharmacological inhibitors for Akt, some of which are being evaluated in clinical trials (Cheng et al., 2008 Curr. Cancer Drug Targets 8: 2-6; Levy et al, 2009 Blood 113: 1723-1729), differ with regard to their relative activities against Akt isoforms. Indeed, selective inhibition of Akt isoforms is associated with lower toxicity (Mao et al., 2007 J. Immunol. 178: 5443-53). However, this report indicates that preferential activity of a given compound against Akt1 or Akt2 may also have disadvantages. Given that tumors developing in the Akt1$^{-/-}$ genetic background grow slower than tumors developing in the wild-type and Akt2$^{-/-}$ genetic backgrounds, it is possible that an inhibitor that targets primarily Akt1 may cause cancer remission. However, if the tumor relapses, the tumor cells emerging after relapse may be significantly more aggressive, invasive, and metastatic. On the other hand, an inhibitor that targets primarily Akt2 may be ineffective. It is therefore important to test existing and future Akt inhibitors preclinically for potential differences in their ability to target Akt1, Akt2, and Akt3. The sensitivity of the three Akt isoforms to a given inhibitor was used herein to design therapeutic strategies that maximize tumor responsiveness and prevent the unwanted selection of invasive and metastatic tumor cells.

Pharmacological inhibitors of PI3K/Akt pathway are being developed by different companies and some of them, like the GSK compound GSK690692 and the Merck compound MK-2206 are being evaluated in clinical trials. Inhibitors of the PI3K/Akt pathway under development include but are not limited to dual PI3K and mTOR inhibitors: BEZ235 (Novartis), BGT226 (Novartis), XL765 (Exilixis), SF1126 (Semafore), GSK1059615 (GSK); PI3K inhibitors: XL147 (Exilixis), PX866 (Oncothyreon), GDC0941 (Genentech/Piramed/Roche), BKM120 (Novartis), CAL101 (targets p110d; Calistoga Pharmaceuticals); Akt inhibitors: Perifosane (Keryx), GSK690693 (GSK), VQD002 (Vioquest), MK2206 (Merck); and mTOR inhibitors (catalytic site): OSI027 (OSI Pharmaceuticals), and AZD8055 (AstraZeneca).

These compounds differ with respect to off target effects, and with respect to their relative activities against the three Akt isoforms. It is therefore important to employ additional independent tests for preclinical evaluation of the compounds. Here the expression of conventional genes and non-coding RNAs, and protein modifications associated with the activity of individual Akt isoforms are examined, in a panel of immortalized or transformed breast carcinoma cell lines before and after treatment with these compounds. In examples herein special attention is paid to markers that are differentially regulated by different Akt isoforms in cells growing under conditions of normoxia or hypoxia. The data obtained better define properties of available inhibitors and provide information for their proper use. For example, based on examples herein one predicts that an inhibitor that targets primarily Akt1 cause cancer remission, and the tumor cells following relapse are significantly more invasive and metastatic, unless measures are taken to alter the microRNA profile of the tumors during treatment. On the other hand, an inhibitor that targets primarily Akt2 may be ineffective to treat cancer.

Examples herein introduce a platform for the preclinical testing of the specificity of Akt inhibitors toward the three Akt isoforms. This platform includes Phase Ia-Validation, Phase Ib-Validation and Phase II Preclinical and Clinical evaluation of RTK and Akt inhibitors. Phase Ia-Validation determines whether changing the balance between Akt1 and Akt2 in tumor cell lines affects their tumor initial properties, metastatic potential. Phase Ib-Validation compares the biochemical and biological parameters defining the metastatic potential, the response to treatment and the rate of ovarian tumors with high and low levels of Akt2 and the effects of imbalance between Akt1 and Akt2. Phase II, Preclinical and Clinical evaluation, determines the effects of receptor tyrosine kinase (RTK) and Akt inhibitors on the expression of microRNAs differentially regulated by Akt isoforms examined in a set of humor tumor cell lines as part of a preclinical evaluation of specificity of inhibitors. The results provide the information needed to design protocols of the use of inhibitors and monitor the effects of the inhibitors during the treatment.

A portion of this work was published in a paper entitled "MicroRNAs differentially regulated by Akt isoforms, control EMT and stem cell renewal in cancer cells" by Dimitrios Iliopoulos, Christos Polytarchou, Maria Hatziapostolou, Filippos Kottakis, Joanna G. Maroulakou, Kevin Struhl, and P. N. Tsichlis that appeared Oct. 13, 2009 in Sci. Signal vol. 2 p. ra62, which is hereby incorporated herein by reference in its entirety.

An aspect of the invention here provides a method for prognosing or diagnosing a potential cancer and progression of an existing cancer in a patient involving measuring an expression profile of a plurality of microRNA (miRNA) species in a sample from the patient, and comparing the profile from the patient with that of a normal subject, such that measuring the expression profile includes a technology selected from: analyzing amount of miRNA species using an array format having a plurality of miRNA sequences, each species at a known location on a substrate, and real-time miRNA PCR; such that a difference in the expression profile in the sample from the patient and from the subject is a prognosis or diagnosis of the potential cancer or an indication of progression of the existing cancer.

In various embodiments of the method, measuring the miRNA involves measuring a member of the mir-200 miRNA family. In general, the mir-200 miRNA family is at least one selected from the group of: miR-200a, miR-200b, and miR-200c.

In general, measuring the expression profile of a plurality of miRNA species in a sample from a patient involves obtaining the sample from a biopsy of the patient including a plurality of cells. For example, obtaining the samples includes obtaining cells that are further cultured ex vivo for screening potential inhibitors to restore Akt expression balance and thereby inhibit the cancers. In an embodiment, obtaining the cells involves obtaining epithelial cells. In other embodiments, obtaining the cells involves obtaining cells from a sample at least one of blood, cerebrospinal fluid, mammary glands, prostate gland, lung biopsy, bladder biopsy, cervix biopsy, and colorectal biopsy.

An alternative embodiment of the method further involves observing decreased expression of at least one miRNA associated with at least one transcription factor and a prognosis of cancer or cancer progression. In another embodiment, method further involves observing decreased expression of at least one miRNA associated with of Zeb1 and Zeb2 and a prognosis of cancer or cancer progression. In another embodiment, the method further involves observing a decreased expression of at least one miRNA associated with E-cadherin and a prognosis of cancer or cancer progression. In another embodiment, the method further involves observing a decreased expression of at least one miRNA associated with cells for an epithelial-mesenchymal-transition (EMT) phenotype and a prognosis of cancer or cancer progression.

In general, the method further involves observing decreased expression of at least one miRNA selected from the group of miR-200a, miR-200b, and miR-200c and a prognosis of cancer or cancer progression. In another embodiment, the method further involves observing decreased expression of at least one miRNA associated with an imbalance of Akt isoforms in the patient and a prognosis of cancer or cancer progression. In another embodiment, the method further involves observing decreased expression of miRNA species associated with imbalance of expression of Akt1 and/or Akt2 and a prognosis of cancer or cancer progression. In another embodiment, the method further involves observing miRNA species associated with a reduced expression of Akt1 and a prognosis of cancer or cancer progression. In another embodiment, the method involves further observing no change of overall Akt levels and a prognosis of cancer or cancer progression. In another embodiment, the method further involves determining motility of the sample, such that increased motility is an indication of invasiveness and/or metastasis.

In general, the method involves providing a diagnosis or a prognosis for the patient, such that the diagnosis or prognosis is an indication of at least one condition selected from: metastasis, invasiveness, and progression of the cancers.

Yet another embodiment provides a method for screening an anti-cancer agent among a library of compounds such that the agent downregulates a pathway associated with cancer, the method involving: identifying an alteration in amount of expression of microRNA (miRNA) species expressed in a patient with cancer that downregulates a cancer; contacting cells from the patient with at least one of the compounds; and analyzing amounts of miRNA associated with each of Akt protein and Akt protein inhibitors, such that the anti-cancer agent is observed to upregulate miRNA associated with the Akt isoforms and the Akt isoform inhibitor. In general, the method further involves observing miRNA selected from the group of miRNA-200. For example The miRNA is a member of the miR-200 miRNA family, for example miR-200a, miR-200b, and miR-200c.

In an alternative embodiment, the method involves observing Akt isoforms selected from the group of Akt1 and Akt2. In another embodiment, the method involves observing Akt isoform inhibitors that inhibit Akt isoforms selected from the group of Akt1 and Akt2.

In yet another embodiment, the method involves observing an anti-cancer agent that does not change overall Akt isoform levels. In another embodiment, the method involves observing an anti-cancer agent that downregulates Akt isoforms. In an alternative embodiment, the method further involves observing an anti-cancer agent that upregulates Akt isoforms.

In another embodiment, the method involves obtaining the sample from a biopsy of the patient comprising a plurality of cells. In another embodiment, the cells are further cultured ex vivo for testing of potential inhibitors or agents. For example, the method involves cells that are epithelial. In yet another embodiment, the method involves obtaining cells from at least one of the group of a sample of blood, cerebrospinal fluid, mammary glands, prostate gland, lung biopsy, bladder biopsy, cervix biopsy, and colorectal biopsy.

In general, the method involves observing decreased expression of at least one miRNA associated with at least one transcription factor and a prognosis of cancer or cancer progression. Alternatively, method further involves observing decreased expression of at least one miRNA associated with of Zeb1 and Zeb2 and a prognosis of cancer or cancer progression. Alternatively, the method involves observing a decreased expression of at least one miRNA associated with E-cadherin and a prognosis of cancer or cancer progression. Alternatively, the method involves observing a decreased expression of at least one miRNA associated with cells for an epithelial-mesenchymal-transition (EMT) phenotype and a prognosis of cancer or cancer progression.

A kit in another aspect of the invention is provided for prognosing or diagnosing a potential cancer and prognosis of the cancer in a patient, the kit including: a plurality of miRNA species on an array, such that each miRNA is chosen for activity that specifically down-regulates gene expression, a container, and instructions for use. In another embodiment, the kit includes TGFβ. In another embodiment, the kit includes siRNA. For example, the siRNA is directed to genes encoding Akt isoforms. In another embodiment, the siRNA is a control not encoding an Akt protein or any of Akt proteins.

In another embodiment, the kit includes Akt isoforms that are at least one selected from the group of Akt1, Akt2 and Akt3. In another embodiment, the kit includes a positive control.

In general, one plurality of miRNA species in the kit is a set of members of miR-200 miRNA family. For example, the miR-200 miRNA family is at least one selected from the group of: miR-200a, miR-200b, and miR-200c.

Methods are provided herein of using microRNA profiling of tumors to meaningfully interpret the level of activity of different Akt isoforms in vivo. Accordingly a method of screening for the expression of specific microRNAs meaningfully interprets the level of activity of different Akt isoforms in vivo. Such microRNAs include all the microRNAs that are differentially regulated by different Akt isoforms in growth factor stimulated cells and in cells exposed to hypoxia, as shown in Examples and figures herein. Also provided is a method by microRNA profiling and screening for the expression of specific microRNAs, for making predictions concerning the outcome of individual patients. These methods involve measuring expression and phosphorylation of individual Akt isoforms, for example, high activity of Akt2 and imbalance between Akt1 and Akt2 with Akt2 predominance is associated with increased invasiveness and metastasis as well as with resistance of tumors and cells to hypoxia. Also provided herein are methods by microRNA profiling of cells expressing all Akt isoforms before and after treatment with the inhibitor, of evaluating potential new anti-cancer drugs. Expression of specific microRNAs differentially regulated by Akt isoforms, before and after treatment with the inhibitor, provides a screen to evaluate novel Akt inhibitors. For example, inhibitors of Akt1 that have no effect or a small effect on Akt2, create an imbalance that inhibits the expression of the microRNAs miR-200a, miR-200a, miR-200a, miR-141 and mir-449 and increases the expression of miR-10b in IGF-stimulated cells. Similarly, expression of miR-21 in the same cells is increased upon exposure to hypoxia.

Similarly, methods herein are useful to rationally design protocols for the use of Akt inhibitors in the treatment of cancer. For example, inhibitors that target preferentially Akt1 and create an imbalance between Akt1 and Akt2, with Akt2 predominance, are used only in combination with treatments that target the ability of Akt2 to promote EMT and resistance to hypoxia. This is done by targeting the downstream effectors of Akt2.

The cell lines provided herein are useful for evaluation of the biological roles of each of the Akt isoforms alone, or in combinations of two at a time.

Pharmaceutical Compositions

In one aspect of the present invention, pharmaceutical compositions are provided, such that these compositions include a miRNA or a protein, encoding a regulatory element affecting expression, or comprising an amino acid sequence of an Akt gene isoform, an isoform of Akt-1, -2 or 3, and optionally includes a pharmaceutically acceptable carrier. In certain embodiments, these compositions optionally further include one or more additional therapeutic agents. In certain embodiments, the target of choice and/or the additional therapeutic agent or agents include one or more growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), B vitamins such as biotin, and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences* Ed. by Gennaro, Mack Publishing, Easton, Pa., 1995 describes a variety of different carriers that are used in formulating pharmaceutical compositions and known techniques for the preparation thereof. Some examples of materials that are pharmaceutically acceptable carriers include, but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Therapeutically Effective Dose

The methods of treatment provided herein include the treatment of a cell or cell population in need of balancing Akt isoforms or inhibition of immortalization as described herein. Thus, the invention provides methods for the treatment of the cell or cells with an miRNA regulating expression of an Akt isoform protein or peptide, or the protein or peptide, alone or conjugated for example PEGylated, in such amounts and for such time as is necessary to achieve the desired result. It will be appreciated that this encompasses administering an inventive pharmaceutical as a therapeutic measure to promote a balance of Akt isoforms, for example, as a means of producing a tissue for treatment of a condition in need of active cells. In certain embodiments of the present invention a "therapeutically effective amount" of the pharmaceutical composition is that amount effective for promoting Akt balance. The compositions, according to the method of the present invention, may be administered using any amount and any route of administration effective for treating the cells or tissues. Thus, the expression "amount effective for promoting the treating the condition", as used herein, refers to a sufficient amount of composition to promote immortalization or inhibit senescence. The exact dosage is chosen by the individual physician in view of the patient to be treated. Dosage and administration are adjusted to provide sufficient levels of the one or more active agent or to maintain the desired effect. Additional factors which may be taken into account include the severity of a disease state, e.g., extent of the condition, history of the condition; age, weight and gender of the patient; diet, time and frequency of administration; drug combinations; reaction sensitivities; and tolerance/response to therapy. Long acting pharmaceutical compositions might be administered several time points a day, every day, 3 to 4 days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions of the present invention are decided by an attending physician, within the scope of sound medical judgment. For any active agent, the therapeutically effective dose can be estimated initially either in cell culture assays or in animal models, usually mice, rabbits, dogs, or pigs. The animal model is also used to achieve a desirable concentration range and route of administration. While direct application to the cell is envisioned as the route of administration, in vivo or ex vivo, such information can then be used to determine useful doses and additional routes for administration in animals or humans. A therapeutically effective dose refers to that amount of active agent that ameliorates the symptoms or condition. Therapeutic efficacy and toxicity of active agents can be determined by standard pharmaceutical procedures in cell cultures or animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies are used in formulating a range of dosage for human use.

Administration of Pharmaceutical Compositions

After formulation with an appropriate pharmaceutically acceptable carrier in a desired dosage, the pharmaceutical compositions of this invention can be administered to humans and other mammals topically such as transdermally (as by powders, ointments, or drops), i.e., as applied directly to the skin or mucosa. Alternative and additional routes such as orally, rectally, parenterally, intracisternally, intravaginally, intraperitoneally, bucally, or nasally, depending on the severity of the condition being treated, are envisioned.

Liquid dosage forms for administration include buffers and solubilizing agents, preferred diluents such as water, preservatives such as thymosol, and one or more biopolymers or polymers for conditioning the solution, such as polyethylene glycol, hydroxypropylmethylcellulose, sodium hyaluronate, sodium polyacrylate or tamarind gum.

Liquid dosage forms for oral administration include, but are not limited to, pharmaceutically acceptable emulsions, microemulsions, solutions, suspensions, syrups and elixirs. In addition to the at least one active agent, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular administrations are aqueous drops, a mist, an emulsion, or a cream. Administration may be therapeutic or it may be prophylactic. Prophylactic formulations may be present or applied to the site of potential wounds, or to sources of wounds, such as contact lenses, contact lens cleaning and rinsing solutions, containers for contact lens storage or transport, devices for contact lens handling, eye drops, surgical irrigation solutions, ear drops, eye patches, and cosmetics for the eye area, including creams, lotions, mascara, eyeliner, and eyeshadow. The invention includes devices, surgical devices, audiological devices or products which contain disclosed compositions (e.g., gauze bandages or strips), and methods of making or using such devices or products. These devices may be coated with, impregnated with, bonded to or otherwise treated with a disclosed composition.

The ointments, pastes, creams, and gels may contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Powders and sprays can contain, in addition to the agents of this invention, excipients such as talc, silicic acid, aluminum hydroxide, calcium silicates, polyamide powder, or mixtures of these substances. Sprays can additionally contain customary propellants such as chlorofluorohydrocarbons.

Transdermal patches have the added advantage of providing controlled delivery of the active ingredients to the body. Such dosage forms are made by dissolving or dispensing the compound in the proper medium. Absorption enhancers can also be used to increase the flux of the compound across the skin. The rate is controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent is accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the one or more active agent of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or fillers or extenders such as starches, sucrose, glucose, mannitol, and silicic acid, binders such as, for example, carboxymethylcellulose, alginates, gelatin, polyvinylpyrrolidinone, sucrose, and acacia, humectants such as glycerol, disintegrating agents such as agar-agar, calcium carbonate, potato or tapioca starch, alginic acid, certain silicates, and sodium carbonate, solution retarding agents such as paraffin, absorption accelerators such as quaternary ammonium compounds, wetting agents such as, for example, cetyl alcohol and glycerol monostearate, absorbents such as kaolin and bentonite clay, and lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

EXAMPLES

Example 1

Cell Culture, Constructs and Retroviral Infections

Mouse lung fibroblasts from Akt1$^{fl/fl}$/Akt2$^{-/-}$/Akt3$^{-/-}$ mice were cultured in DMEM supplemented with 10% fetal bovine serum (FBS), penicillin and streptomycin, sodium pyruvate, nonessential amino acids and glutamine. Passage of these cells every three to four days led to the establishment of spontaneously immortalized cell lines (Meek et al., 1977 Exp. Cell Res. 107: 277). Established cell lines were cultured in this same medium, under standard culture conditions.

Wild-type Akt1, Akt2 and Akt3, tagged with the myc epitope at their C-terminus, were cloned in the retroviral vector pBabe-puro. Retrovirus constructs were packaged in 293T cells transiently transfected with these constructs and with an ecotropic virus construct. Immortalized lung fibroblasts were infected with the packaged viruses as follows: Cells were pre-treated with DEAE dextran (25 μg/ml). Forty five minutes later, they were washed and infected. Infected cells were selected for puromycin (Sigma) resistance (2 μg/ml). Cells generated from three independent infections for each retroviral construct, were analyzed for Akt expression by probing their lysates with antibodies specific for myc (#2276), Akt1 (#2938), Akt2 (#2964) and Akt3 (#3788, catalog numbers, Cell Signaling Technologies). To abolish the expression of the endogenous Akt1, cells were super-infected with a MigR1-GFP-based construct of the Cre recombinase and they were sorted 48 hours later. To avoid puromycin selection, Akt1$^{fl/fl}$/Akt2$^{-/-}$/Akt3$^{-/-}$ lung fibroblasts were alternatively transduced with mycAkt1, mycAkt2, or mycAkt3 in the retroviral vector MigR1-GFP, and cells transduced with the respective viruses were superinfected with a MigR1-RFP (red fluorescent protein)-based construct of the Cre recombinase.

Ablation of endogenous Akt1 by Cre, gave rise to Akt-null cells (TKO) or triple Akt knockout cells expressing a single Akt isoform at a time. MCF10A mammary epithelial cells were grown in DMEM/F 12 medium supplemented with 5% donor horse serum (HS), 20 ng/ml epidermal growth factor (EGF), 10 μg/ml insulin, 100 μg/ml hydrocortisone, 1 ng/ml cholera toxin and 50 units/ml penicillin and streptomycin.

Examples using MEFs from wild-type, Akt1$^{fl/fl}$/Akt2$^{+/+}$/Akt3$^{-/-}$, Akt1$^{+/+}$/Akt2$^{-/-}$/Akt3$^{-/-}$, and Akt1$^{fl/fl}$/Akt2$^{-/-}$/Akt3$^{-/-}$ mice were carried out to determine whether the effects of individual Akt isoforms on regulating miR-200 family also occurs in primary mouse embryo fibroblasts (MEFs). Transduction with a MigR1-GFP-Cre construct was performed herein to knock out the endogenous foxed Akt1 allele.

MCF10A mammary epithelial cells were grown in DMEM/F12 medium supplemented with 5% donor horse serum, epidermal growth factor (EGF, 20 ng/ml), insulin (10 μg/ml), hydrocortisone (100 μg/ml), cholera toxin (1 ng/ml), and penicillin and streptomycin (50 U/ml).

Example 2

Human Breast Cancer Samples

RNAs from eight primary tumors and their corresponding metastatic tumors were purchased from Biochain Inc. These samples were used for real-time RT-PCR for E-cadherin, miR-200a, miR-200b, Akt1, and Akt2. Glyceraldehyde-3-phosphate dehydrogenase (GAPDH) expression levels were used as a loading control.

Example 3

MicroRNA Expression Analysis

Expression levels of 365 microRNAs were evaluated using TLDA microRNA v1.0 arrays (Applied Biosystems). Cells were serum-starved overnight. Sixteen hours later, they were stimulated with IGF1 (50 ng/ml) and they were harvested 1, 4 and 16 hours later. Differentially expressed microRNAs were clustered using hierarchical clustering analysis. Changes in microRNA abundance were illustrated with heat maps.

Darker color gray represents downregulation and light color gray represents upregulation of a given microRNA in IGF1-treated fibroblasts.

Example 4

MicroRNA Real-Time PCR Analysis

Figure 3A:
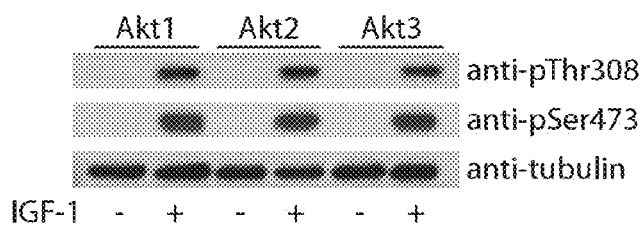
FIGS. 3A-3E are a set of photographs of immunoblots, heatmaps, an overlapping circles diagram and a set of bar graphs showing Akt isoforms have different microRNA genetic signatures.
Figure 3B:
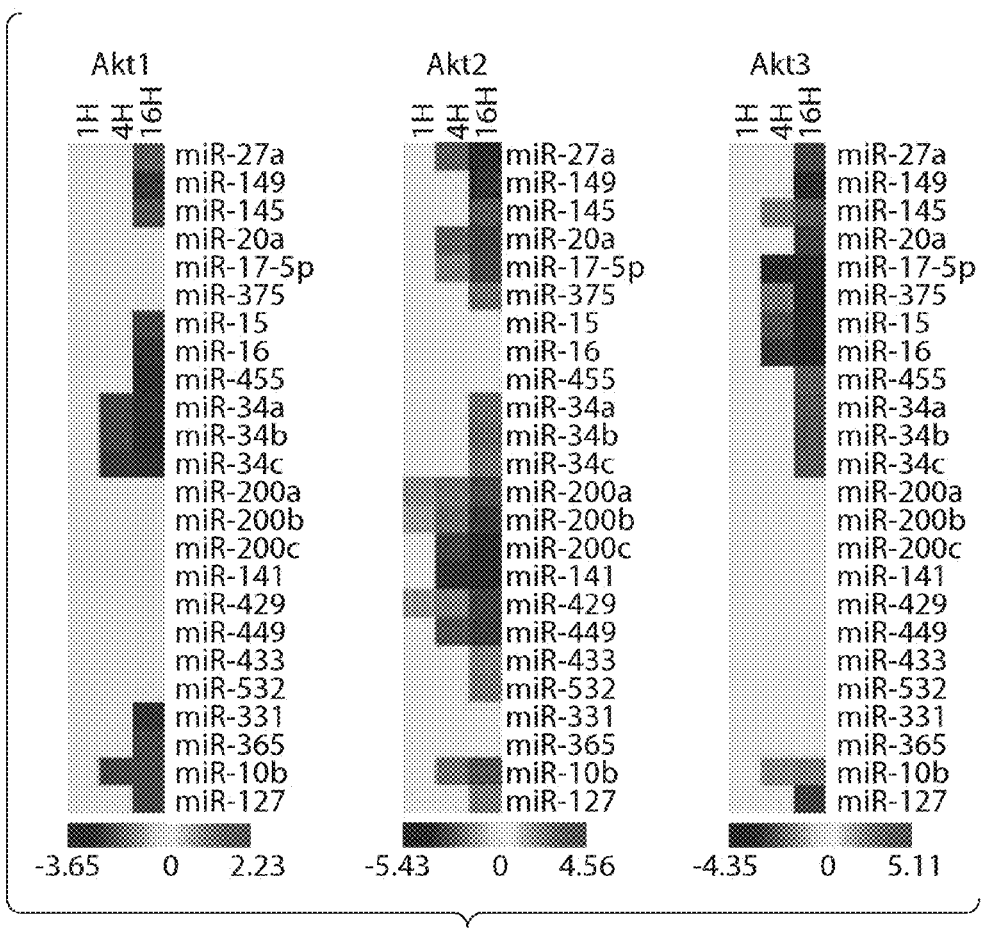
Figure 3C:
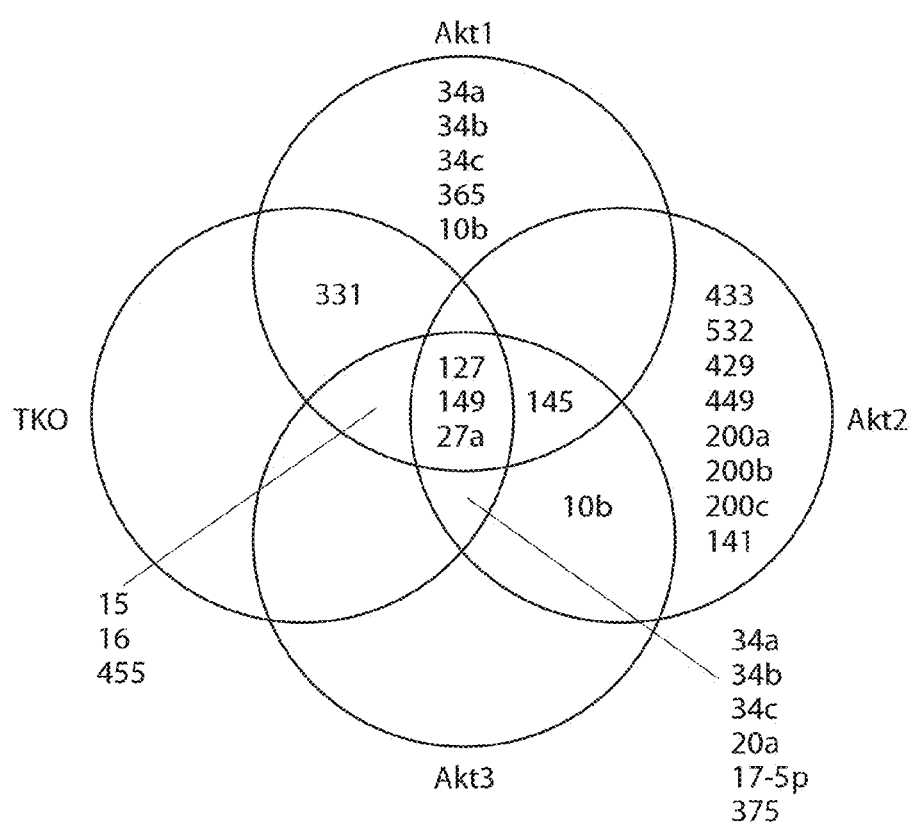
Figure 3D:
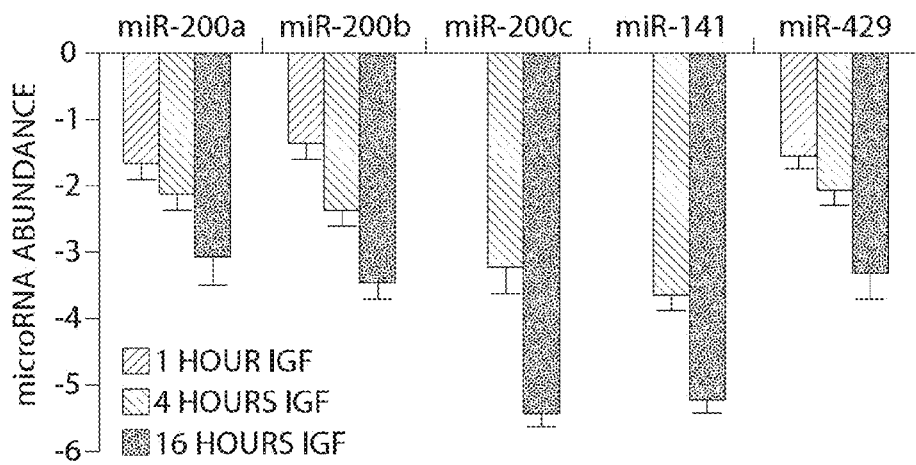
Figure 3E:
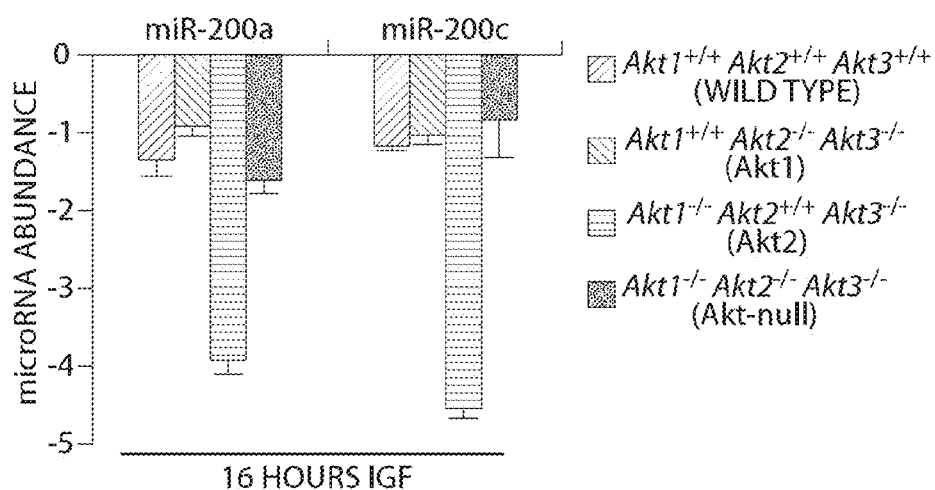
Figure 11A:
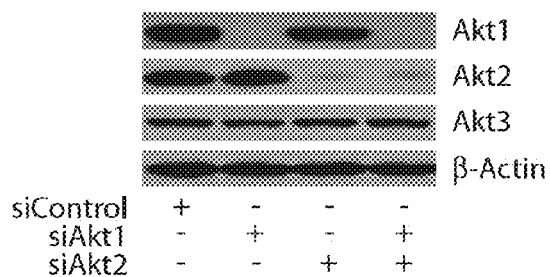
FIGS. 11A-11E are a set of photographs of immunoblots, bar graphs, chromosomal maps and line graphs showing that knockdown of Akt1 promotes EMT by decreasing abundance of the miR-200 microRNA family.
Figure 11B:
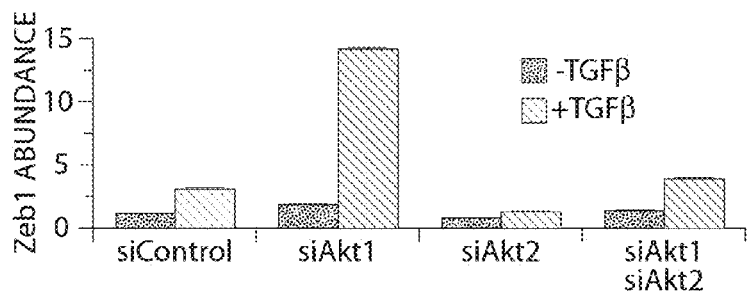
Figure 11C:
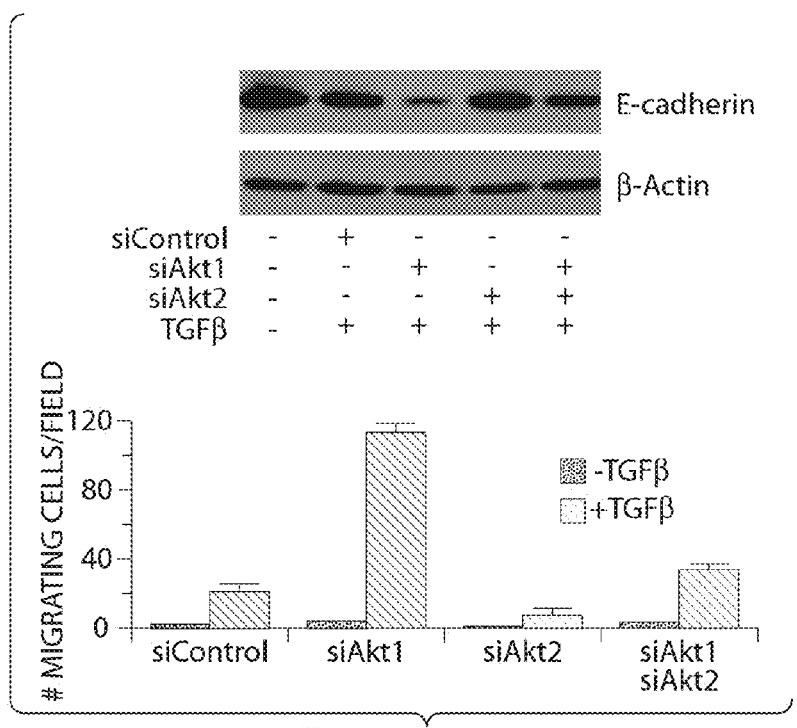
Figure 11D:
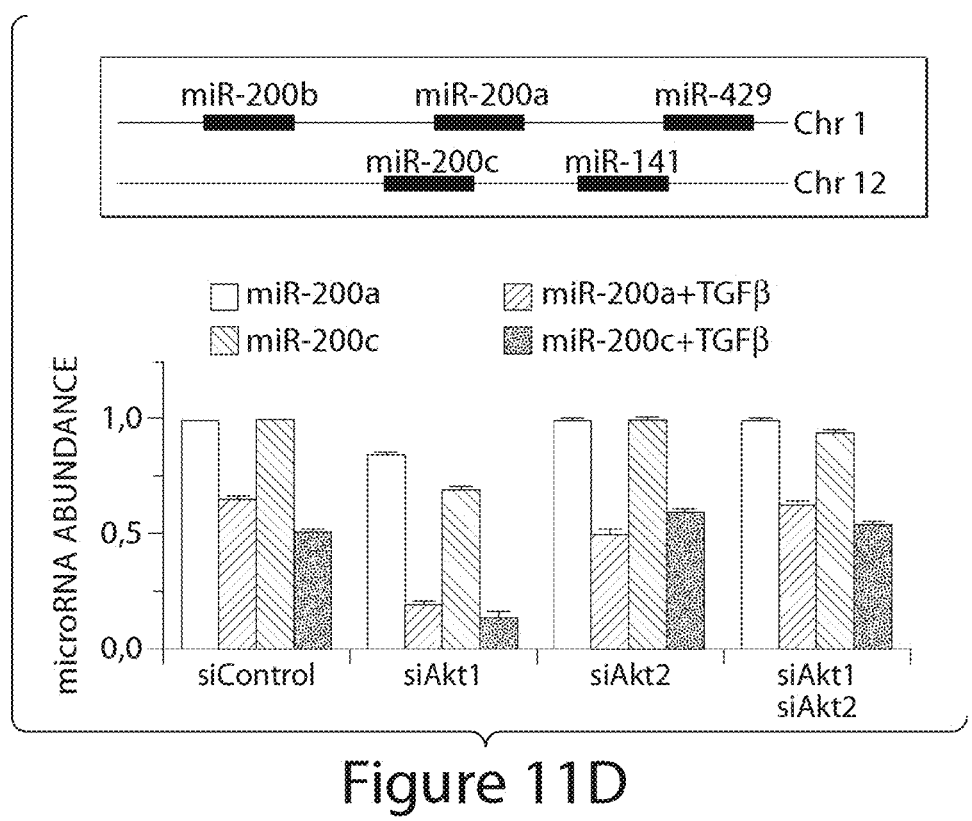

Validation of microRNA array data was performed using the mirVana qRT-PCR miRNA Detection Kit and qRT-PCR Primer Sets (Ambion Inc, TX, USA). The expression of RNU48 and RNU44 was used as internal control. Real-time RT-PCR analysis was also performed to determine the abundance of miR-200a, miR-200b, miR-200c, miR-141 and miR-429 in MCF10A cells transfected with a negative control siRNA designed to have no sequence similarity to a human transcript sequence (#AM4611), or siRNAs against Akt1 (#S660), Akt2 (#S1216, catalog numbers, Ambion Inc.), or both and treated with TGFβ (20 ng/ml) for 24 hours. The abundance of these microRNAs was also normalized to RNU48 and RNU44 expression (internal controls). Data in FIGS. 3D and 3E show the relative abundance of miR-200 family members at different time points after IGF1 treatment. The microRNA abundance before treatment was set at 0. FIG. 11D shows the relative abundance of miR-200 family members in MCF10A cells treated with siRNAs directed against Akt1 and/or Akt2, and TGFβ. The microRNA abundance in cells transfected with the control siRNA and not treated with TGFβ were set at 1.

Example 5

Real-Time PCR Analysis

Total RNA was extracted with Trizol (Invitrogen) according to the manufacturer's instructions. Complementary DNA (cDNA) was synthesized from 2.0 µg of total RNA by random priming with the Omniscript reverse transcription kit (Qiagen). Real-time PCR was performed in triplicate with the Quantitect SyBr green PCR system (Qiagen) on a Rotorgene 6000 series PCR machine (Corbett Research). mRNA quantification data were normalized to β-actin, which was used as an internal control. The following primer sets were used: (for Zeb1)

```
                              (forward; SEQ ID NO: 1)
    5'TTCAAACCCATAGTGGTTGCT3'
    and (reverse; SEQ ID NO: 2)
    5'TGGGAGATACCAAACCAACTG3';

(for Zeb2)
                              (forward; SEQ ID NO: 3)
    5'CAAGAGGCGCAAACAAGC3'
    and (reverse; SEQ ID NO: 4)
    5'GGTTGGCAATACCGTCATCC3';

(for E-cadherin)
                              (forward; SEQ ID NO: 5)
    5'TGCCCAGAAAATGAAAAAGG 3'
    and reverse; SEQ ID NO: 6)
    5'CTGGGGTATTGGGGGCATC3';

(for Vimentin)
```

```
                -continued
                              (forward; SEQ ID NO: 7)
    5'GAGAACTTTGCCGTTGAAGC3'
    and (reverse; SEQ ID NO: 8)
    5'CTAACGGTGGATGTCCTTCG3',
    and for Akt1/2
                              (forward; SEQ ID NO: 9)
    5'CTTCGAG-CTCATCCTCATGG3'
    and (reverse; SEQ ID NO: 10)
    5'TCTGCTTGGGGTCCTTCTTA3'.
```

Example 6

Western Blot Analysis

Fibroblasts were lysed on ice, using a Triton X-100 lysis buffer (50 mM Tris, pH 7.5, 150 mM NaCl, 1 mM EDTA, 1 mM EGTA, 1% Triton X-100, 2.5 mM sodium orthovanadate, 1 mM phenylmethylsulfonyl fluoride, 50 mM NaF, leupeptin (10 µg/ml), and aprotinin (5 µg/ml). Twenty micrograms of total protein from each sample were resolved in a 10% SDS-PAGE and transferred to polyvinylidene difluoride (PVDF) membranes. The blots were then probed with antibodies specific for phospho-Akt (Ser$^{473}$ and Thr$^{308}$; catalog numbers #9271 and #9275, Cell Signaling Technologies) and for tubulin (T5168, Sigma).

Transfected MCF10A cells were lysed on ice with an NP-40 lysis buffer (50 mM Tris, pH 7.5, 150 mM NaCl, and 0.5% NP-40). Fifty micrograms of total protein from each sample was resolved in a 4% to 12% bis-tris gel with MOPs running buffer and transferred to PVDF membranes. The blots were then probed with an antibody preparation specific for E-cadherin (catalog number 610404, BD Biosciences) and an antibody specific for β-actin (catalog number ab8227, Abeam Inc).

Example 7

Transwell Migration Assay

Transwell migration assays were performed according to Irie et al., 2005 J. Cell Biol. 171: 1023. MCF10A cells were transfected with a negative control siRNA designed to have no sequence similarity to a human transcript sequence (#AM4611) or siRNAs for Akt1 (#S660) or Akt2 (#S1216), or siRNAs for both Akt 1 and Akt2 (50 nM). Twenty four hours after transfection, cells were cultured overnight in assay medium (MCF10A growth medium containing 2% serum±TGFβ (20 ng/mL)). Sixteen hours later, cells were trypsinized and $10^5$ cells were added to the top chambers of 24-well transwell plates (8 µm pore size; BD Bioscience, Bedford, Mass.). The bottom chambers were filled with assay medium. After overnight incubation, the migratory cells were fixed and stained with 0.1% crystal violet. The significance of variability between a given group and its corresponding control was determined with the unpaired t test.

Example 8

Mammosphere Culture

MCF10A cells were transfected with a control siRNA, siRNAs for Akt1 or Akt2, or siRNAs for both Akt1 and Akt2

(150 nM). Twenty four hours later, cells were cultured in suspension in low-attachment plates (Corning; 1000 cells/ml), in serum-free DMEM/F12 medium supplemented with B27 (1:50, Invitrogen), 0.4% bovine serum albumin (BSA), 20 ng/ml EGF (Sigma), insulin (Sigma; 4 µg/ml), and 1% methyl cellulose to prevent cell aggregation, in the presence or absence of TGF-β (20 ng/ml). Mammospheres with a diameter of greater than 75 µm were counted six days later. To propagate mammospheres in vitro, mammospheres were collected by gentle centrifugation and dissociated to single cells according to Dontu et al., 2003 Genes Dev 17: 1253. Before replating, mammosphere-derived cells were retransfected with 150 nM of the corresponding siRNAs (control, Akt1, Akt2, or both Akt1 and Akt2). Replating potential describes the ability of single cells to form mammospheres upon culture in new vessels.

Example 9

Mouse Models and Analyses

Homozygous MMTV Neu transgenic mice were established in the wild type, Akt1$^{-/-}$ and Akt2$^{-/-}$ genetic backgrounds according to Maroulakou et al., 2007 Cancer Res 67: 167. Tissues were paraffin-embedded, sectioned, and stained with hematoxylin and eosin. Histologic sections were blindly analyzed as follows. Invasive tumors were evidenced by infiltrative tumor foci in distinction from encapsulated tumor borders. The code was broken only after the data were complete and were compiled.

Protein and RNA isolation were performed using the mirVana PARIS Kit (Ambion). Protein extracts were analyzed by Western Blot for the levels of E-cadherin (catalog number #3195, Cell Signaling Technologies), vimentin (catalog number sc-7558) and Zeb1 (catalog number se-10572, Santa Cruz Biotechnology).

Example 10

In Situ microRNA Hybridization

For in situ hybridization, MiRCURY LNA Detection probes were 3'-end labeled with digoxigenin (DIG) for mmu-miR-200c (39549-05) or scramble-miR (99004-05, Exiqon; Obernosterer et al., 2007 Nat. Protoc. 2: 1508) with the following modifications. Sections (5 µm) of formalin-fixed paraffin embedded Neu/wild-type, Neu/Akt1$^{-/-}$ and Neu/Akt2$^{-/-}$ tumors were deparaffinized in xylene, 2×40 min on a 50 rpm shaker, followed by five min each in serial dilutions of ethanol (100, 100, 75, 50 and 25%), followed by two changes of diethyl pyrocarbonate (DEPC)-double distilled water (ddH$_2$O). Slides were then submerged for 5 min in 0.2 N HCl, washed with DEPC-phosphate-buffered saline (PBS), digested with proteinase K (40 µg/ml) for 20 min at 25° C., rinsed in 0.2% glycine/DEPC-PBS, 3×DEPC-PBS, and post-fixed with 4% formaldehyde in PBS for 10 min. Slides were rinsed twice with DEPC-PBS, treated with acetylation buffer (300 µl of acetic anhydride, 670 µl of triethanolamine, 250 µl of 12 N HCl per 48 ml ddH$_2$O) and then rinsed four times in DEPC-PBS followed by two rinses in 5×SSC. Slides were pre-hybridized at 53° C. for 2 hours in hybridization buffer (50% formamide, 5×SSC, 0.1% Tween-20, adjusted to pH 6.0 with 9.2 mM citric acid, heparin (50 µg/ml), and yeast transfer RNA) in a humidified chamber (50% formamide, 5×SSC). After pre-hybridization, slides were hybridized overnight at 53° C. in a humidified chamber with 20 nM of probe in pre-warmed hybridization buffer. Sections were rinsed twice in 5×SSC, followed by three washes of 20 min at 53° C. in 50% formamide and 2×SSC. Sections were then rinsed five times in PBS-0.1% Tween-20 (PBST), and blocked for 1 hour in blocking solution (2% sheep serum, BSA (2 mg/ml) in PBST). Antibody specific for binding to DIG-AP Fab fragments antibody (11093274910, Roche) was applied on sections overnight at 4° C. Slides were washed two times, in PBST for 10 min each and washed three times for 10 min each in 0.1 M Tris-HCl (pH 7.5)/0.15 M NaCl, followed by equilibration with 1 M Tris (pH 8.2) for 10 min and the Fast Red (Roche) solution (one tablet per 2 ml of 0.1 M Tris-HCl (pH 8.2)). After incubation for 30 min in the dark, slides were washed three times in PBST for 10 min and coverslipped in Vectashield mounting medium with 6,6'-diamidino-2-phenylindole (DAPI; Vector Labs).

Sections of the tumors were deparaffinized by incubating in xylene three times for five minutes each, followed by 10 min each in concentrations of ethanol 100% twice, 95% twice, and followed by two changes of double distilled water (ddH$_2$O). Antigen unmasking was performed by boiling the slides (95-99° C.) for 10 min, in 10 mM sodium citrate buffer (pH 6.0). Sections were then rinsed three times in ddH$_2$O, one time in PBS, and blocked for one hour in blocking solution (5% goat serum, 300 µl Triton-X 100 in 100 ml PBS). E-cadherin antibody was diluted (1:200) and applied on sections overnight at 4° C. Slides were washed three times in PBS for 5 mM each, and were incubated with Cy2-conjugated antibody against goat immunoglobulin G diluted 1:500 for one hour at room temperature in the dark. Slides were washed three times in PBS for 5 min each, and were coverslipped in Vectashield mounting medium with DAPI.

Images were obtained using a Nikon Eclipse 80i microscope and a Spot charge-coupled device camera (Diagnostic Instruments). Photographs were processed using identical settings for capturing and further processing.

Example 11

Akt Isoforms have Different microRNA Gene Signatures

Figure 1B:
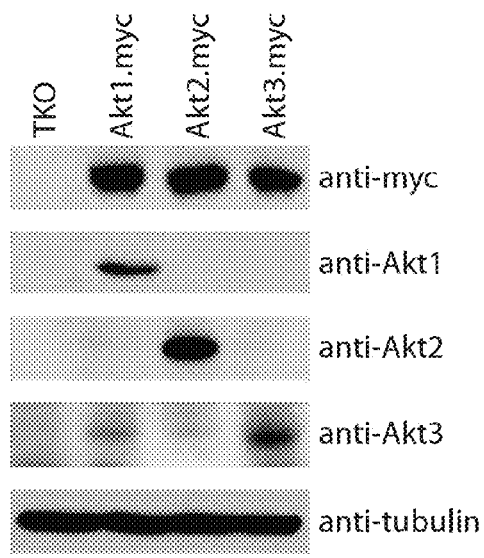
Figure 1C:
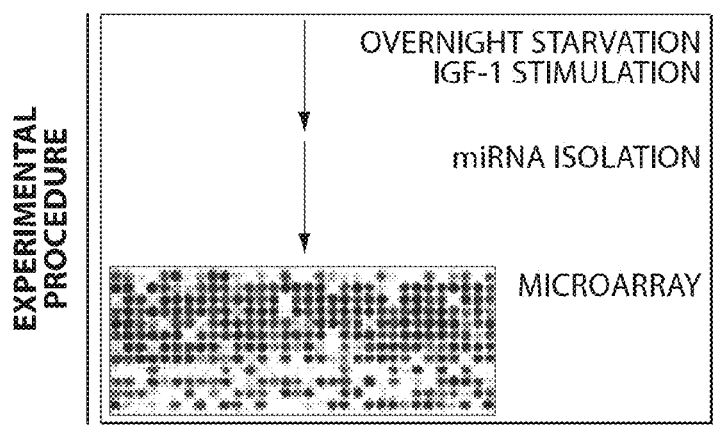
Figure 2:
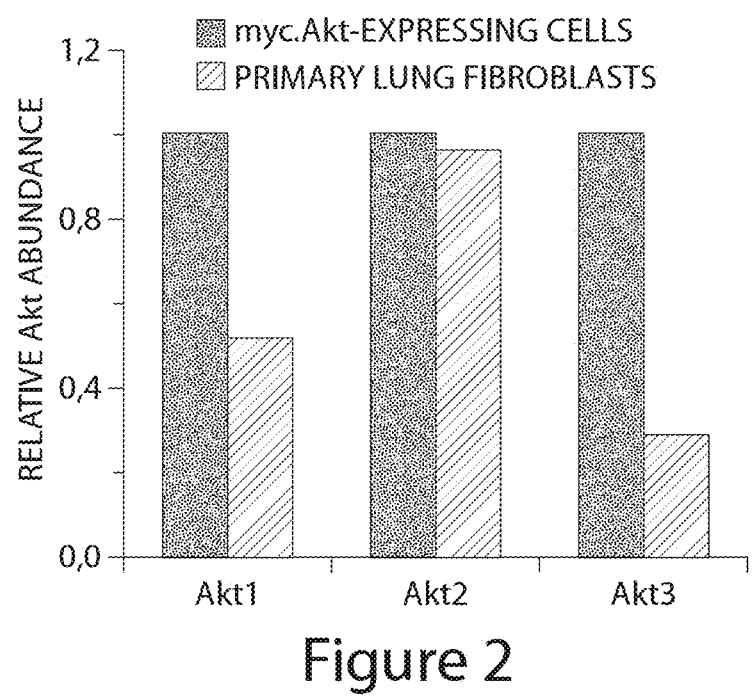
FIG. 2 is a set of bar graphs showing abundance of the three Akt isoforms in spontaneously immortalized lung fibroblasts transduced with retroviral constructs of Akt1, Akt2, or Akt3 and in primary lung fibroblasts from wild type mice. Western blots of cell lysates were probed with the indicated Akt1-, Akt2-, or Akt3-specific antibodies. Tubulin was used as loading control. Protein bands were measured by densitometry.

Lung fibroblast and kidney epithelial cells from Akt1$^{fl/fl}$/Akt2$^{-/-}$/Akt3$^{-/-}$ mice were immortalized as described herein. The immortalized lung fibroblasts were transduced with myc-tagged Akt1, Akt2, or Akt3 retroviral constructs or with the empty retroviral vector. Knocking out the floxed Akt1 allele in these cells with Cre recombinase gave rise to cell lines that expressed only one of each of the three Akt isoforms. Knocking out the foxed Akt1 in the vector-transduced cells gave rise to Akt-null cells, which survived for about a week, but failed to proliferate. The abundance of mycAkt1, mycAkt2, and mycAkt3 in cell lines engineered to express a single Akt isoform was similar (FIG. 1). Moreover, the abundance of mycAkt1 in these cell lines was about two times higher and the abundance of mycAkt3 three times higher than the abundance of endogenous Akt1 and Akt3, respectively, in primary lung fibroblasts. However, the abundance of the individual Akt isoforms in these cell lines did not exceed that of total Akt in the primary cells (FIG. 2).

To determine the role of the three Akt isoforms on the abundance of microRNAs, Akt-null cells and cells expressing a single Akt isoform were stimulated with IGF1, which activates the Akt kinase. Probing whole-cell lysates harvested before and after IGF1 stimulation with phosphospecific antibodies recognizing activated Akt phosphorylated at Thr$^{308}$ and Ser$^{473}$ confirmed that IGF1 activated three Akt isoforms (FIG. 3A).

Figure 4:
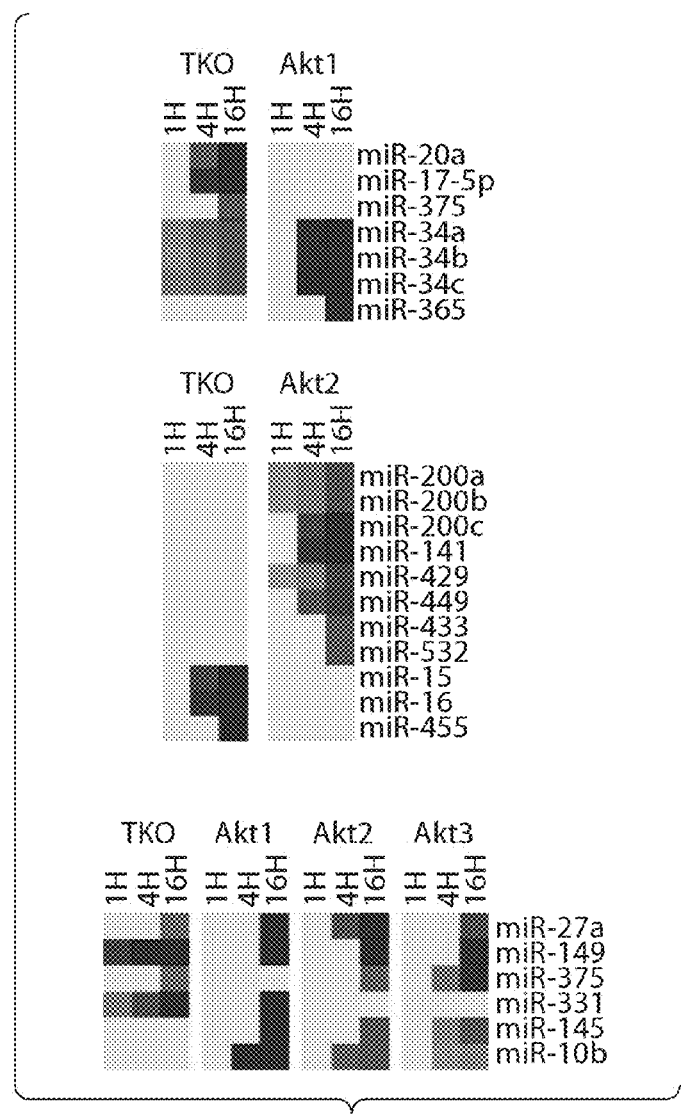
FIG. 4 is a set of heatmaps of differentially expressed microRNAs in untreated and IGF1-treated fibroblasts, expressing no Akt (TKO), or individual Akt isoforms. Light color gray indicates upregulation, and darker color gray indicates downregulation. The three panels show microRNAs that are upregulated or downregulated differentially in response to IGF1, in TKO and Akt1-expressing cells (upper panel), TKO and Akt2-expressing cells (middle panel), and TKO and Akt1-, Akt2-, and Akt3 expressing cells (lower panel; see also Table 2).

After confirmation of the activation of Akt, cell lysates harvested before and after IGF1 treatment were screened with a 365-member microRNA array. Based on this analysis, no differences were found in microRNA abundance between cells carrying different Akt isoforms under basal conditions; however, IGF1 treatment elicited marked differences in the microRNA signature of the different groups (FIG. 3B). In cells with Akt1, IGF1 increased or decreased the abundance of 1 and 12 microRNAs, respectively, whereas in cells with Akt2, it increased or decreased the abundance of 7 and 12 microRNAs, respectively; finally, in cells with Akt3, IGF1 increased the abundance of 5 and decreased the abundance of 9 microRNAs (FIG. 3B). The abundance of some microRNAs (miR-27a, miR-149, and miR-145) changed in the same direction, but differed quantitatively between IGF1-treated cells expressing different Akt isoforms, whereas the abundance of other microRNAs changed in the opposite direction in these cells (FIG. 3C, FIG. 4, and Tables 1 and 2).

TABLE 1

The microRNA signatures of immortalized lung fibroblasts expressing a single Akt isoform at a time and responding to IGF1, exhibit dramatic differences.

| microRNA | Akt1 | Akt2 | Akt3 | Function | Reference |
|---|---|---|---|---|---|
| miR-27a | −1.76 | −5.23 | −2.43 | Cell cycle | Mertens-Talcott et al., 2007 Cancer Res. 67: 11001. |
| miR-149 | −2.34 | −3.56 | −4.35 | Oncogenic | Wong et al., 2008 Clin. Cancer Res. 14: 2588 |
| miR-145 | 2.23 | 4.56 | 5.11 | IRS1[1] target | Shi et al., 2007 J. Biol. Chem. 282: 32582 |
| miR-20a | 0 | −3.24 | −2.54 | Cell cycle | Pickering et al., 2008 Oncogene |
| miR-17-5p | 0 | −3.12 | −4.18 | Cell cycle | Cloonan et al., 2008 Genome Biol. 9: R127 |
| miR-375 | 0 | −2.25 | −3.13 | PDK1[2] target | Ouaamari et al., 2008 Diabetes 57: 2708 |
| miR-15 | −2.13 | 0 | −4.23 | BCL2[3] target | Cimmino et al., 2005 Proc. Natl. Acad. Sci. U.S.A. 102: 13944 |
| miR-16 | −2.45 | 0 | −3.55 | BCL2 target | Cimmino et al., 2005 Proc. Natl. Acad. Sci. U.S.A. 102: 13944 |
| miR-455 | −3.65 | 0 | −2.12 | Adipocyte differentiation | Walden et al., 2009 J. Cell Physiol. 218: 444 |
| miR-34a | −2.54 | 2.56 | 4.86 | cell cycle-p53 | He et al., 2007 Nature 447: 1130 |
| miR-34b | −2.88 | 2.87 | 4.31 | cell cycle | He et al., 2007 Nature 447: 1130 |
| miR-34c | −2.53 | 2.52 | 3.87 | cell cycle | He et al., 2007 Nature 447: 1130 |
| miR-200a | 0 | −3.05 | 0 | EMT | Gregory et al., 2008 Nat. Cell Biol. 10: 593; Park et al., 2008 Genes Dev. 22: 894 |
| miR-200b | 0 | −3.46 | 0 | EMT | Gregory et al., 2008 Nat. Cell Biol. 10: 593; Park et al., 2008 Genes Dev. 22: 894 |
| miR-200c | 0 | −5.43 | 0 | EMT | Gregory et al., 2008 Nat. Cell Biol. 10: 593; Park et al., 2008 Genes Dev. 22: 894 |
| miR-141 | 0 | −5.23 | 0 | EMT | Gregory et al., 2008 Nat. Cell Biol. 10: 593; Park et al., 2008 Genes Dev. 22: 894 |
| miR-429 | 0 | −3.32 | 0 | EMT | Gregory et al., 2008 Nat. Cell Biol. 10: 593; Park et al., 2008 Genes Dev. 22: 894 |
| miR-449 | 0 | −3.4 | 0 | Endometrioid carcinoma | Wu et al., 2009 Eur. J. Cancer Prev. 1: 50 |
| miR-433 | 0 | 2.12 | 0 | ERR[4] gamma pathway | Song et al., 2008 Nucleic Acid Res. 18: 5727 |
| miR-532 | 0 | 2.34 | 0 | Unknown | |
| miR-331 | −2.45 | 0 | 0 | SOCS1[5] target | Zannete et al., 2007 Braz. J. Med. Biol. Res. 11: 1435 |
| miR-365 | −2.13 | 0 | 0 | UVB[6] irradiation | Guo et al., 2008 Photochem. Photobiol. |
| miR-10b | −2.13 | 4.32 | 2.37 | Metastasis | Ma et al., 2007 Nature 7163: 682 |

[1] IRS1 is an insulin receptor substrate 1.
[2] PDK1 is a phosphoinositide-dependent kinase 1
[3] BCL2 is B-cell lymphoma 2.
[4] ERR is an estrogen-related receptor.
[5] SOCS1 is a suppressor of cytokine signaling 1.
[6] UVB is ultraviolet B.

To obtain these data, cells were treated with IGF1 and were harvested 16 hours later. The numbers indicate fold differences in expression levels between unstimulated and IGF1-stimulated cells.

TABLE 2

Comparison of the microRNA signatures of triple Akt knockout (TKO) lung fibroblasts, and derivatives expressing Akt1, Akt2 or Akt3. Cells were treated with IGF1 and were harvested 16 hours later. The numbers indicate fold differences in expression levels between unstimulated and IGF1-stimulated cells. The panels show microRNAs which were upregulated or downregulated differentially in response to IGF1, in TKO and Akt1-expressing cells (upper panel), TKO and Akt2-expressing cells (middle panel) and TKO and Akt1, Akt2 and Akt3-expressing cells (lower panel; see FIG. 1).

| miR | TKO |
|---|---|
| Upper panel | |
|  | Akt1 |
| miR-20a | −3.21  0 |
| miR-17-5p | −3.69  0 |
| miR-375 | −1.85  0 |
| miR-34a | 4.56  −2.54 |
| miR-34b | 4.11  −2.88 |
| miR-34c | 3.97  −2.54 |
| miR-365 | 0  −2.13 |
| Middle panel | |
|  | Akt2 |
| miR-200a | 0  −3.05 |
| miR-200b | 0  −3.46 |
| miR-200c | 0  −5.43 |
| miR-141 | 0  −5.23 |
| miR-429 | 0  −3.32 |
| miR-449 | 0  −3.4 |
| miR-433 | 0  2.12 |
| miR-532 | 0  2.34 |
| miR-15 | −4.76  0 |
| miR-16 | −4.32  0 |
| miR-455 | −3.21  0 |

| Lower panel | | | | |
|---|---|---|---|---|
| miR | TKO | Akt1 | Akt2 | Akt 3 |
| miR-27a | −1.88 | −1.76 | −5.23 | −2.43 |
| miR-149 | −4.12 | −2.34 | −3.56 | −4.35 |
| miR-331 | −3.26 | −2.45 | 0 | 0 |
| miR-145 | 0 | 2.23 | 4.56 | 5.11 |
| miR-10b | 0 | −2.13 | 4.32 | 2.37 |

MicroRNAs subject to regulation by different Akt isoforms that was determined to be qualitatively different included the members of the miR-200 microRNA family (miR-200a, miR-200b, miR-200c, miR-141, and miR-429), abundance of which was decreased after IGF1 treatment only in Akt2-expressing cells (FIGS. 3B and 3C). These microRNAs had been previously clustered in a family because they are coordinately regulated and they share seed sequences and targets (Gregory et al., 2008 Nat. Cell Biol. 10: 593-601; Park et al., 2008. Genes Dev. 22: 894-907).

Figure 5A:
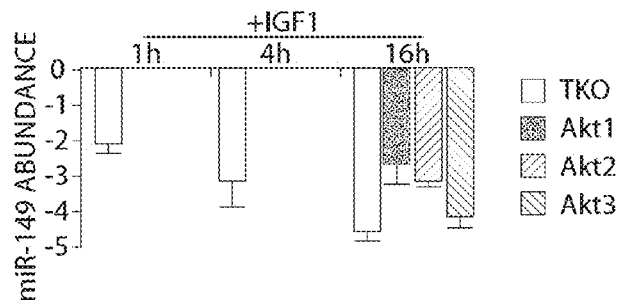
FIGS. 5A and 5B are a set of bar graphs with data showing validation of microRNA microarray data by SYBR Green Real-time RTPCR analysis in Akt1-, Akt2-, and Akt3-expressing fibroblasts. After overnight serum starvation cells were treated with IGF1 (50 ng/ml) and harvested at each of 1, 4, or 16 h after treatment. The data show that addition of IGF1-induced changes in abundance of representative examples of Akt-regulated microRNAs.
Figure 5B:
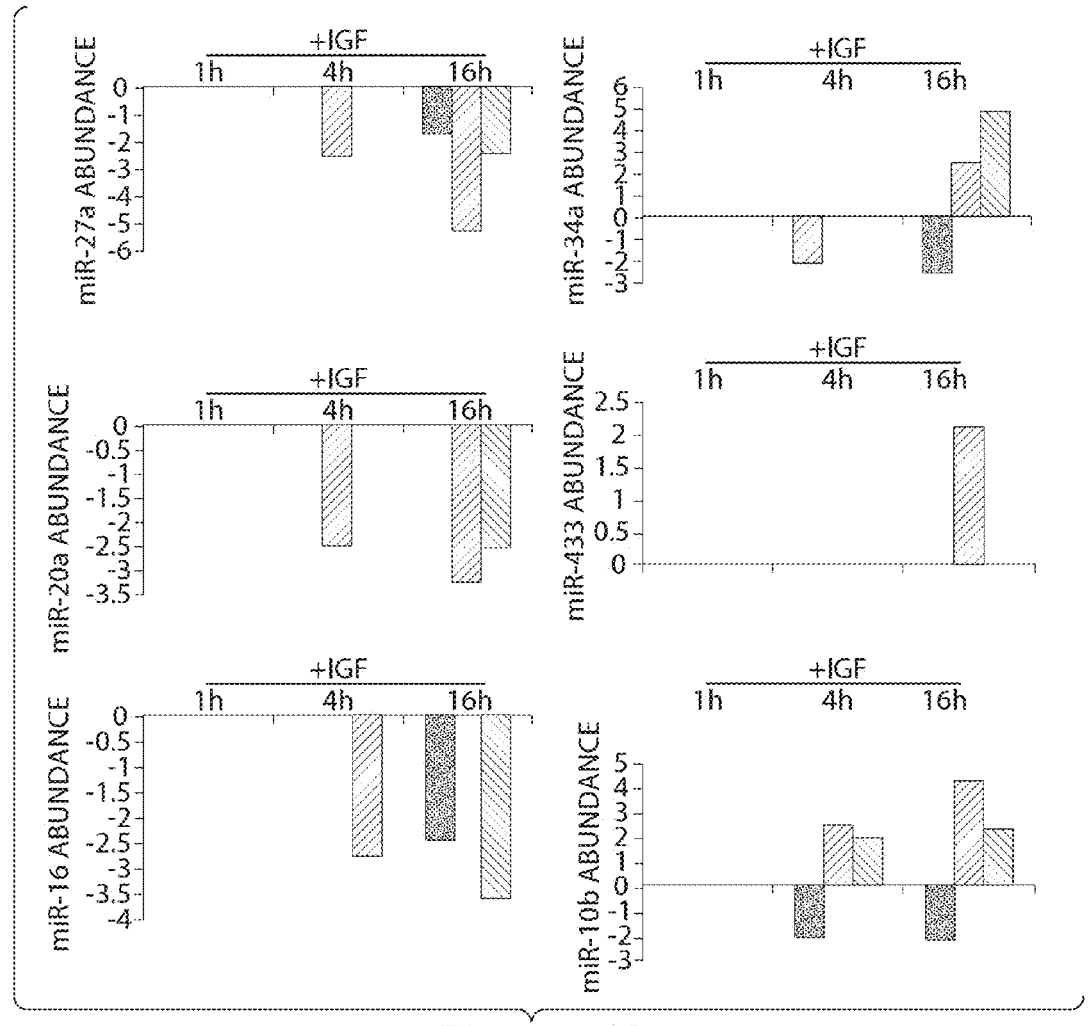
Figure 6:
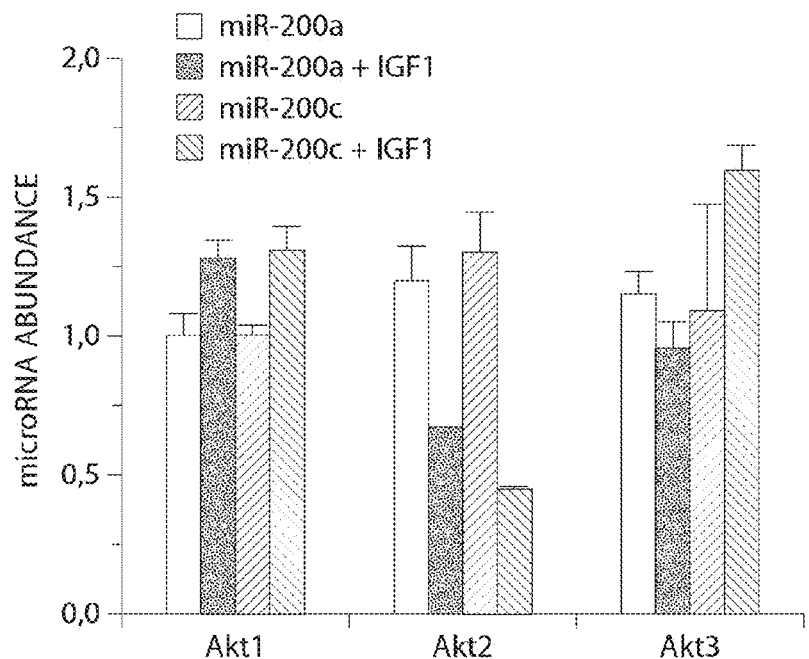
FIG. 6 is a set of bar graphs showing abundance of miR-200a and miR-200c in spontaneously immortalized lung fibroblasts from Akt1$^{fl/fl}$/Akt2$^{-/-}$/Akt3$^{-/-}$ mice transduced with MigR1-GFP constructs of Akt1, Akt2, or Akt3 and MigR1-RFP-Cre. The abundance of miR-200a and miR-200c was measured 16 hours following IGF1 treatment (50 ng/ml) by real time RT-PCR. MiR-200 family members were observed to be downregulated upon IGF1 treatment only in Akt2-expressing fibroblasts. The procedure was performed in triplicate and data are presented as mean±SD.
Figure 7:
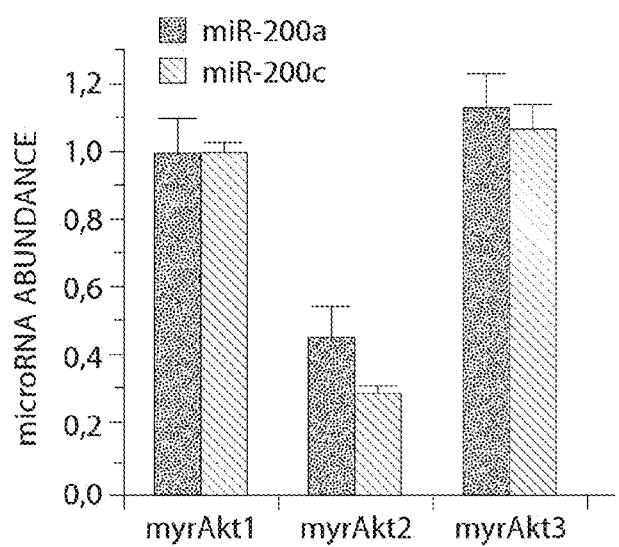
FIG. 7 is a set of bar graphs showing downregulation of miR-200 microRNA family members in myrAkt2-expressing cells. The abundance of miR-200a (left bars) and miR-200c (right bars) was measured by real time RT-PCR in serum-starved cells transduced with pBabe-puro-based constructs of myrAkt1, myrAkt2 or myrAkt3. Data are presented as mean±SD

The differential regulation of the miR-200 microRNA family by the three Akt isoforms was confirmed by real-time reverse transcription polymerase chain reaction (RT-PCR; FIG. 3D and FIG. 5). The Akt2-specific decrease in miR-200 microRNA family abundance was also apparent in IGF1-treated primary mouse embryonic fibroblasts (FIG. 3E) and in IGF1-treated immortalized lung fibroblasts transduced with MigR1-GFP (green fluorescent protein) constructs of Akt1, Akt2, or Akt3 (FIG. 6). A decrease in the abundance of miR-200c and miR-200a was observed also in cells transduced with constitutively active MyrAkt1, MyrAkt2, or MyrAkt3 retroviral constructs, in which the effects of Akt2 did not require IGF1 (FIG. 7).

Figure 8:
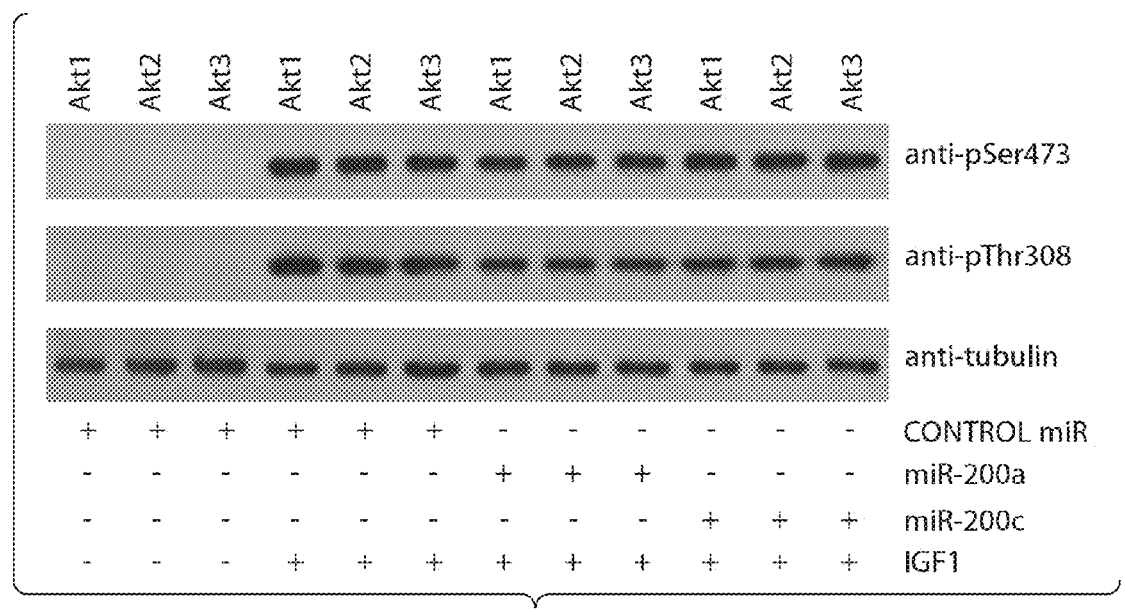
FIG. 8 is a set of photographs of immunoblots showing that Akt1, Akt2 and Akt3 phosphorylation by IGF1 was not affected by overexpression of miR-200a, miR-200c, or miR-200a plus miR-200c. Akt1, Akt2 and Akt3 expressing fibroblasts were transfected with control miR, miR-200a or miR-200e. After overnight serum-starvation, transfected cells were stimulated with IGF1 (50 ng/ml) for 10 min. Western blots of cell lysates were probed with the indicated phospho-specific antibodies. Tubulin was used as loading control.

To determine whether the miR-200 microRNA family also affects Akt activity, lung fibroblasts containing Akt1, Akt2, or Akt3 were transfected with miR-200a, miR-200c, or a control microRNA and measured the phosphorylation of Akt isoforms before and 10 min after IGF1 stimulation. Akt phosphorylation was found to be unaffected by these microRNAs (FIG. 8).

Example 12

Akt1 Knockdown, and not Akt2 Knockdown or of Akt1 and Akt2 Knockdown, Promotes EMT by Decreasing the Abundance of the miR-200 microRNA Family MicroRNAs of the miR-200 family target the 3' untranslated region of the mRNAs encoding the helix-loop-helix transcription factors Zeb1 and Zeb2 and thereby inhibit these factors postranscriptionally. Zeb1 and Zeb2 function as transcriptional repressors of E-cadherin (Gregory et al., 2008 Nat. Cell Biol. 10: 593-601; Park et al., 2008 Genes Dev. 22: 894-907).

Figure 9A:
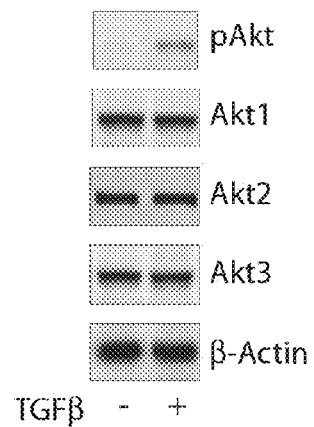
FIGS. 9A and 9B are a set of photographs of immunoblots showing that TGFβ treatment (20 ng/ml) induced Akt phosphorylation (at Ser$^{473}$).
Figure 9B:
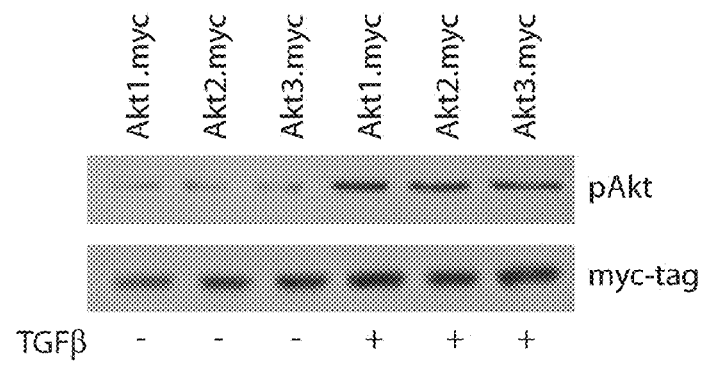

Knockdown of Akt1, leaving Akt2 and Akt3 intact, may induce EMT in epithelial cells by decreasing the abundance of the miR-200 microRNA family. Therefore, the effects of Akt1 knockdown on the abundance of the mRNAs encoding Zeb1, Zeb2, and E-cadherin was examined herein in the mammary epithelial cell line MCF10A. This cell line undergoes EMT after exposure to transforming growth factor $\beta$ (TGF$\beta$; Seton-Rogers et al., 2004 Proc. Natl. Acad. Sci. U.S.A. 101: 1257-1262), which activates Akt in both MCF10A cells and murine lung fibroblasts (FIG. 9).

Figure 10:
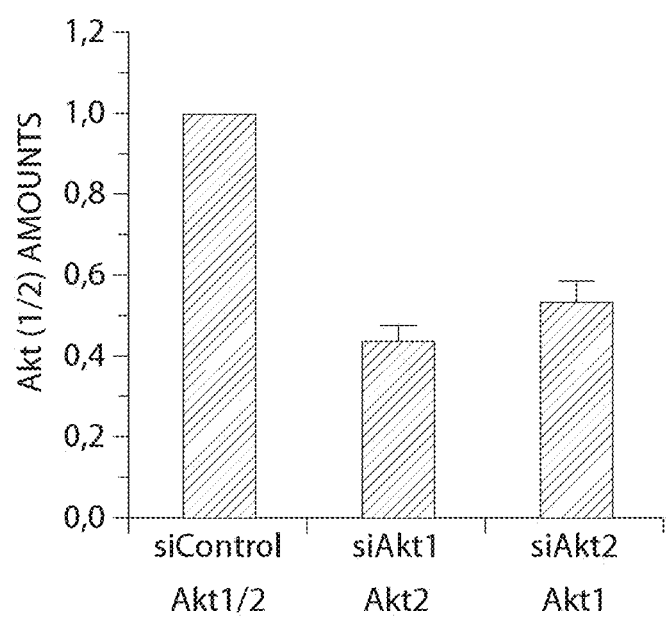
FIG. 10 is a set of bar graphs showing that MCF10A cells have similar amounts of Akt1 and Akt2. Cells were transfected with control siRNA or siRNAs for Akt1 and Akt2 (50 nM) and were analyzed by real time RT-PCR for the expression of Akt1 and Akt2 using primers that detect both Akt1 and Akt2 and not Akt3. The Akt detected in cells transfected with siControl represents the total amount of Akt1 plus Akt2. This was set to a value of 1. The Akt detected in siAkt1 and siAkt2-transfected cells represents the total Akt2 or Akt1 respectively. Their values added together equal approximately 1. Data are presented as mean±SD.
Figure 12A:
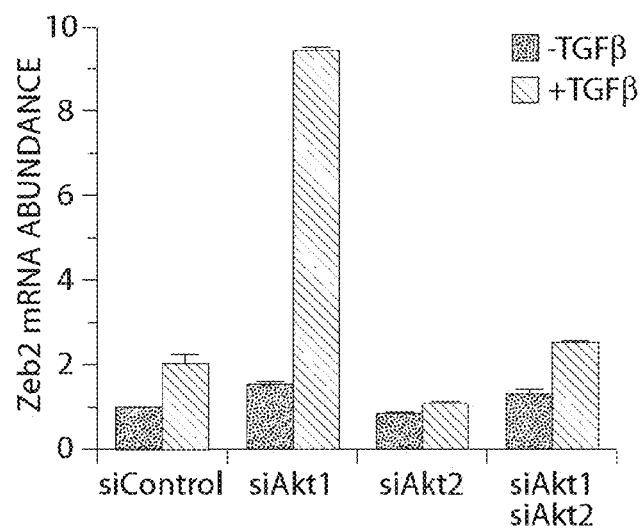
FIGS. 12A and 12B are a set of bar graphs showing that Akt1 and Akt2 have opposing effects on the induction of EMT.
Figure 12B:
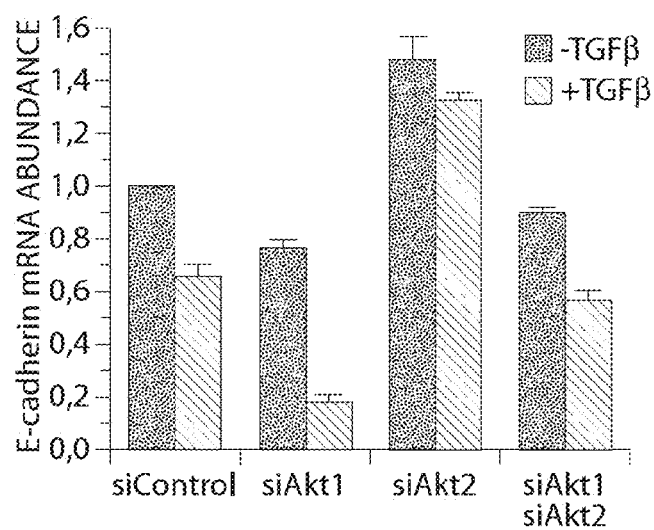
Figure 13A:
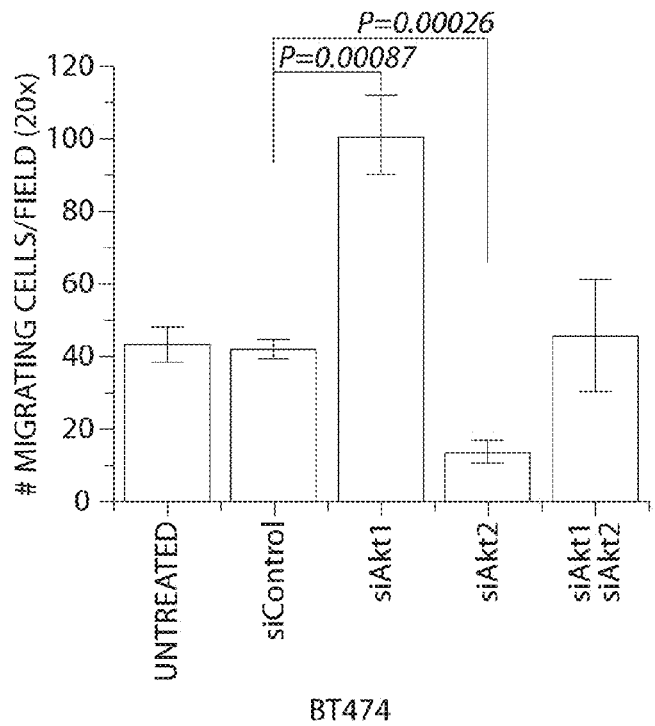
FIGS. 13A and 13B are a set of bar graphs showing that the knockdown of Akt1 enhanced cell motility, and the knockdown of Akt2 did not. Furthermore, the knockdown of Akt2 abolished the effects of Akt1 knockdown on cell motility.
Figure 13B:
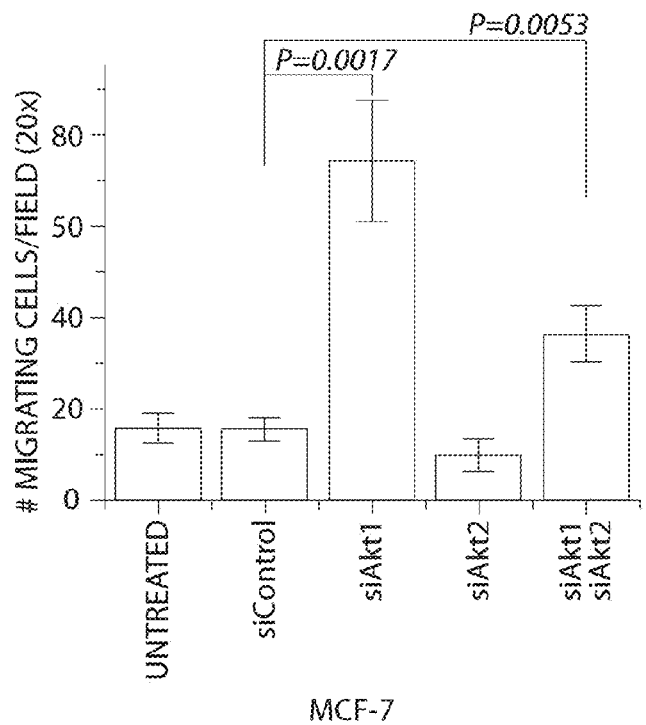

The mRNAs encoding Akt1 and Akt2, which are present in similar abundance in untransfected MCF10A cells (FIG. 10), were respectively knocked down by transfection with small interfering RNA (siRNA) directed against Akt1 or Akt2. However, transfection of these siRNAs alone or in combination had no effect on the abundance of the mRNA encoding Akt3 (FIG. 11A). After transfection with these siRNAs, the cells were analyzed for the abundance of Zeb1, Zeb2, and E-cadherin before and 24 hours after treatment with TGF$\beta$. The knockdown of Akt1, and not the knockdown of Akt2, synergized with TGF$\beta$ to increase the abundance of the mRNAs encoding Zeb1 and Zeb2 and decrease the abundance of E-cadherin at both the mRNA and the protein levels. Moreover, knocking down Akt2 together with Akt1 attenuated the effects of Akt1 knockdown on the abundance of Zeb1, Zeb2, and E-cadherin (FIGS. 11B and 11C, and FIG. 12). EMT also promotes cell migration. Parallel cultures of similarly treated cells were therefore used to measured cell migration by means of a Transwell cell migration assay. Examples herein show that TGF$\beta$ enhanced the migration of untransfected and Akt1 siRNA-transfected MCF10A cells by 7.7 and 22 times, respectively ($P=0.00015$ compared to the control siRNA-transfected cells treated with TGF$\beta$), and the migration of cells transfected with both Akt1 and Akt2 siRNAs by three times ($P=0.05$ compared to the control siRNA-transfected cells treated with TGF$\beta$; FIG. 11C, lower panel). Cell migration therefore exhibited an inverse correlation with the abundance of E-cadherin in MCF10A cells, as expected. The knockdown of Akt1, and not the knockdown of Akt2 or of Akt1 and Akt2, also enhanced migration in the absence of TGFβ in MCF10A cells (P=0.00046; FIG. 11C, lower panel) and in the breast cancer cell lines MCF-7 and BT474 (FIG. 13).

Figure 14:
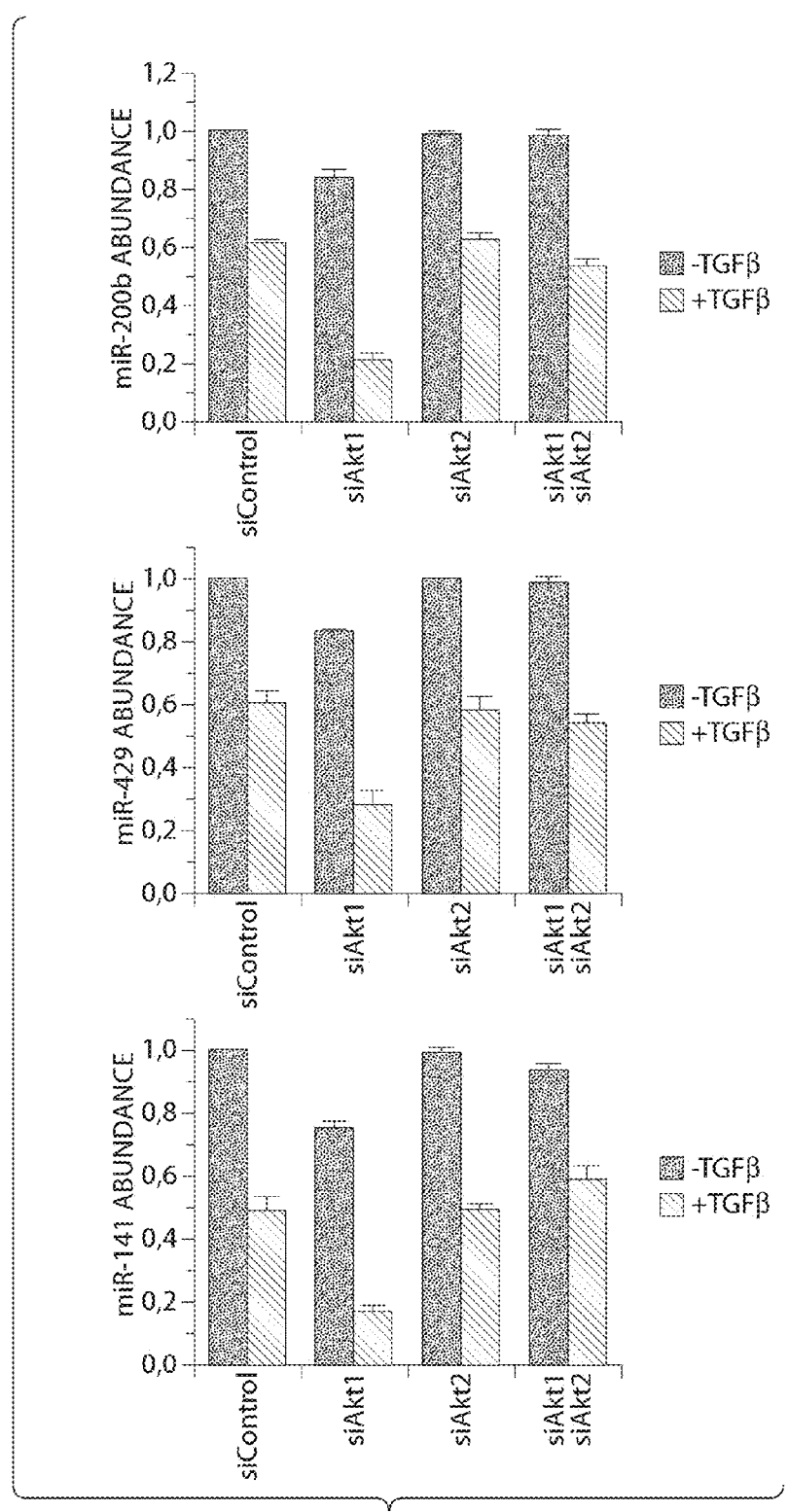
FIG. 14 is a set of graph bars showing that the knockdown of Akt1 decreases the abundance of the members of the miR-200 microRNA family. Real time RT-PCR shows that the knockdown of Akt1 promotes the decrease of the members of the miR-200 microRNA family in MCF10A cells treated with TGFβ (20 ng/ml for 24 hours; right bars). Knockdown of Akt2 does not downregulate the miR-200 microRNAs and abolishes the effects of Akt1 knockdown. The assays were performed in triplicate and data are presented as mean±SD.

The increase in the abundance of Zeb1 and Zeb2 in MCF10A cells in which Akt1 was knocked down may be due to a decrease in the abundance of the miR-200 microRNA family (FIG. 11D, upper panel; Gregory et al., 2008 Nat. Cell Biol. 10: 593-601; Park et al., 2008. Genes Dev. 22: 894-907). Knockdown of both Akt1 and the TGFβ treatment was shown herein to decrease the abundance of this microRNA family and that, when combined, the knockdown of Akt1 and TGFβ acted synergistically to decrease the abundance of these microRNAs (FIG. 11D, lower panel, and FIG. 14).

Figure 11E:
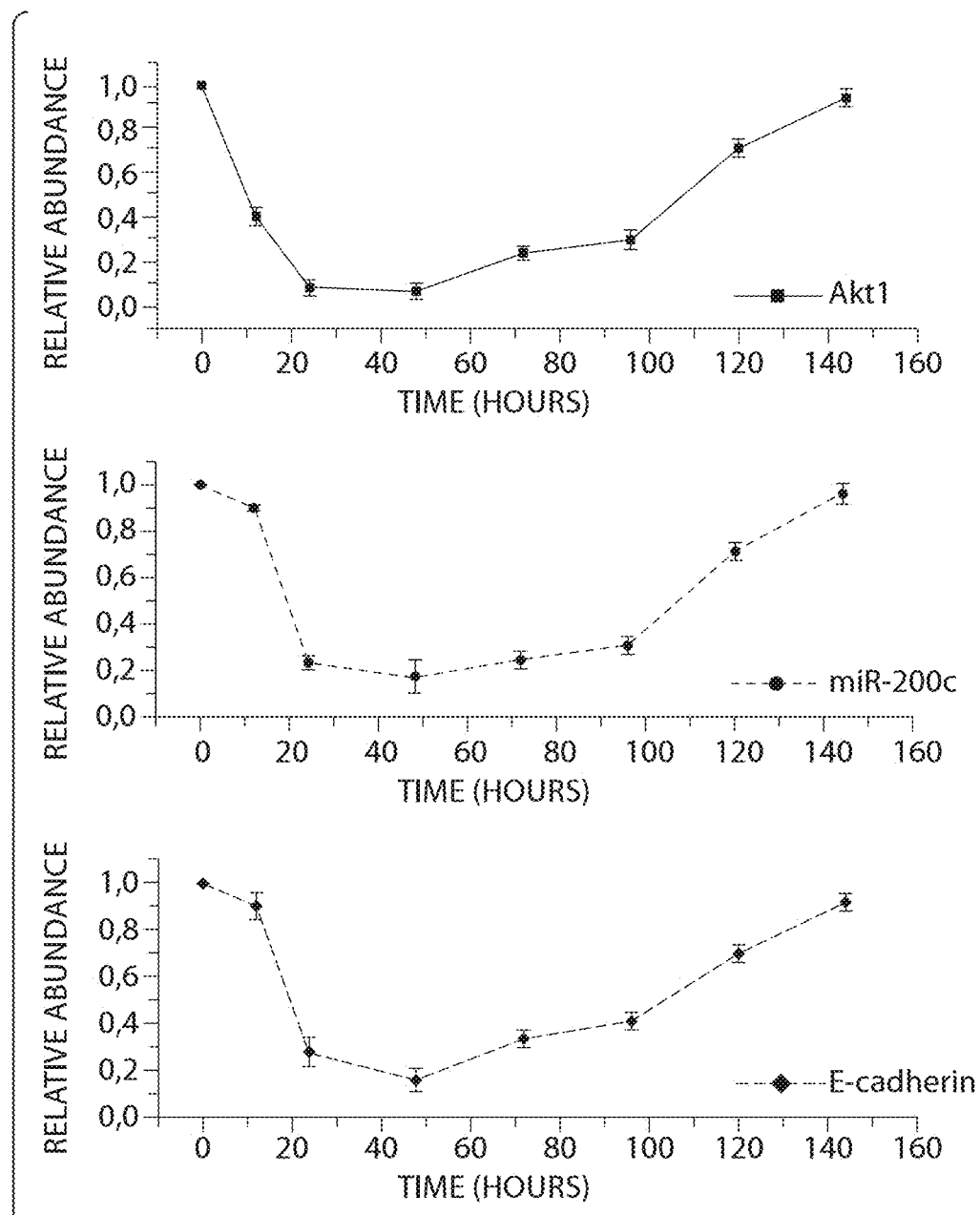
Figure 15:
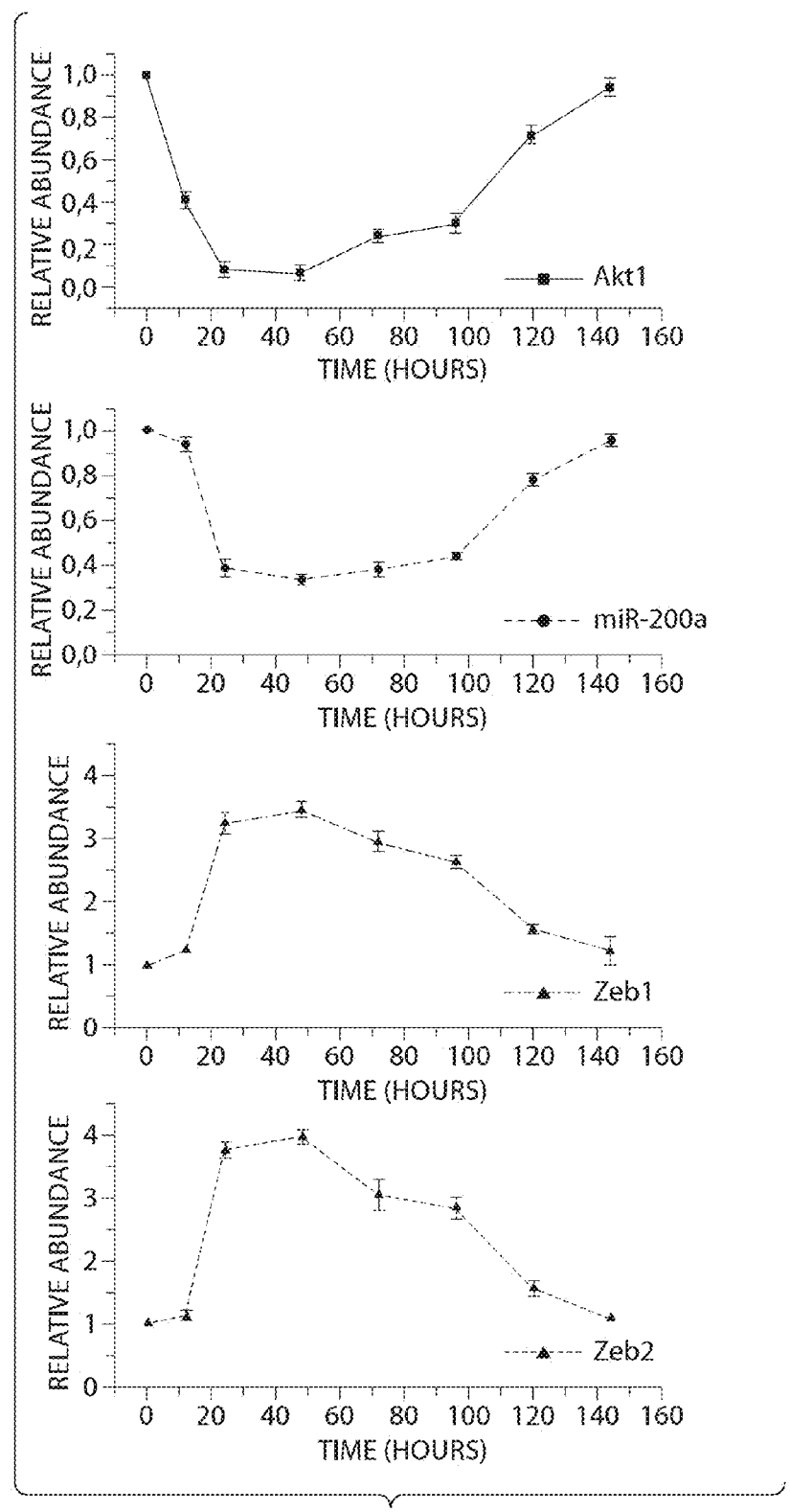
FIG. 15 is a set of line graphs showing that the abundance of miR-200a, and the mRNAs encoding Zeb1, and Zeb2 in MCF10A cells transfected with Akt1 siRNA, returned to the pretransfection values as the effects of the Akt1 siRNA on Akt1 abundance waned. Time course analysis was determined by real-time RT-PCR of the levels of miR-200a, Zeb1 and Zeb2 in MCF10A cells transfected with Akt1 siRNA and treated with TGFβ.

To determine the specificity of the effects of Akt1 knockdown, MCF10A cells transfected with Akt1 siRNA were treated with TGFβ and monitored for 6 days after transfection. As the effects of the Akt1 siRNA waned and Akt1 mRNA returned to its pretransfection value, miR-200a, mill-200c, and the mRNAs encoding Zeb1, Zeb2, and E-cadherin also returned to their pretransfection values (FIG. 11E and FIG. 15).

Examples herein show that changes in the relative abundance of Akt1 and Akt2 that favor Akt2 promote downregulation of the miR-200 microRNA family in both fibroblasts and epithelial cells.

Example 13

Overexpression of miR-200a and miR-200c Inhibits the Effects of TGFβ and Akt1 Knockdown on Zeb1, Zeb2, and E-Cadherin Abundance and on Cell Migration To determine whether the decrease in the abundance of miR-200 microRNAs produced by TGFβ and by the knockdown of Akt1 could mediate the observed changes in the abundance of Zeb1, Zeb2, and E-cadherin, MCF10A cells were transfected with miR-200a, miR-200c, or both miR-200a and miR-200c and examined the abundance of Zeb1 and Zeb2 mRNA 24 hours later.

Figure 16A:
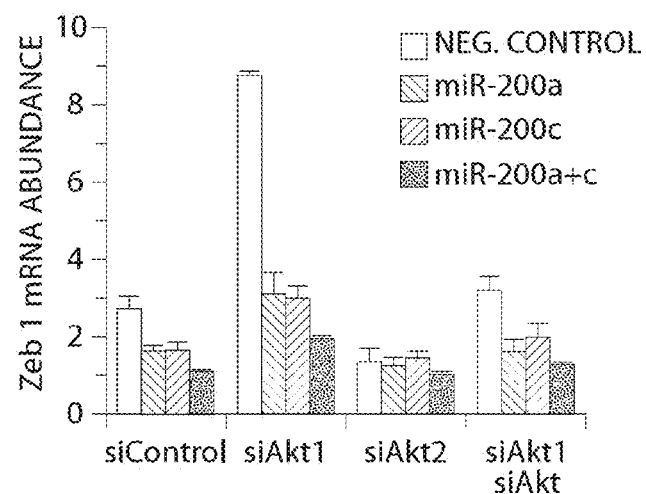
FIGS. 16A-16D are a set of bar graphs showing that overexpression of miR-200a, miR-200c, and both miR-200a and miR200c blocked upregulation of Zeb1 in MCF10A cells transfected with Akt1 siRNA and treated with TGFβ. In assays herein, MCF10A cells were transfected with siRNAs abolishing expression of Akt1 and Akt2, and an siRNA used as a negative control.
Figure 16B:
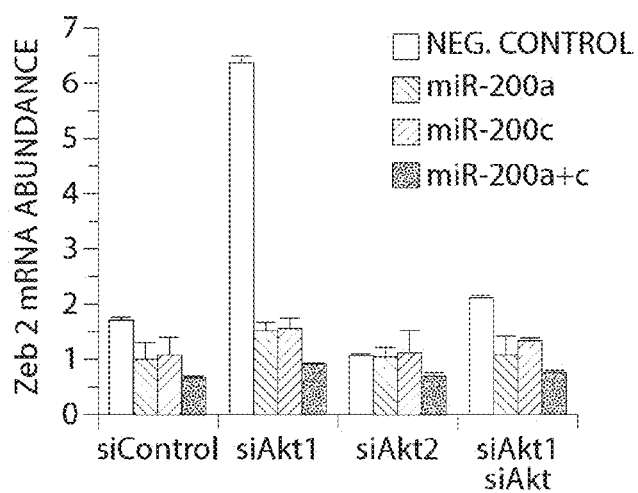
Figure 16C:
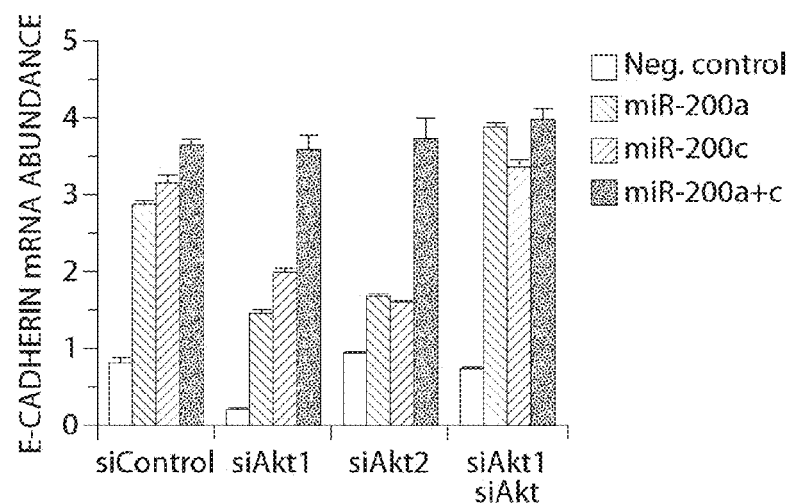
Figure 16D:
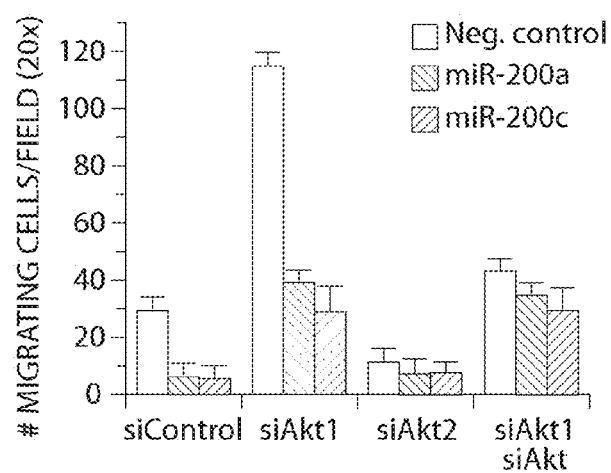

Both microRNAs, alone or combined, were found herein to decrease the abundance of the mRNAs encoding Zeb1 and Zeb2 in cells treated with either TGFβ alone or with TGFβ in combination with Akt1 siRNA (FIGS. 16A and 16B). MCF10A cells transfected with the combination of miR-200a and miR-200c failed to show a decrease in E-cadherin after treatment with TGFβ and Akt1 siRNA (FIG. 16C). Furthermore, transfection with miR-200a or miR-200c blocked the increase in migration produced by treatment with TGFβ and Akt1 siRNA (FIG. 16D).

Examples herein show that Akt1 knockdown increased the abundance of Zeb1 and Zeb2 and promotes EMT by decreasing the abundance of the miR-200 microRNA family.

Example 14

TGFβ- and Akt1 siRNA-Treated Cells Undergoing EMT through a Decrease in the Abundance of miR-200 and Show a Cancer Stem Cell-Like Phenotype Metastases arise when invasive cancer cells that migrate to new sites act as tumor-initiating cells or cancer stem cells (Chiang et al., 2008 N. Engl. J. Med. 359: 2814-2823).

Figure 17A:
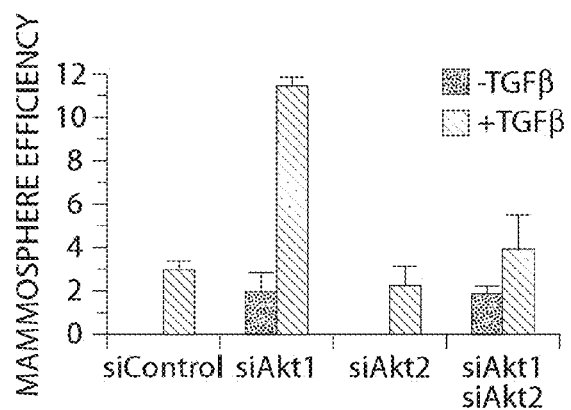
FIGS. 17A-17D are a set of bar graphs and phase-contrast images showing cells undergoing EMT through miR-200 downregulation in response to TGFβ treatment and Akt1 knockdown exhibit stem cell properties.
Figure 17B:
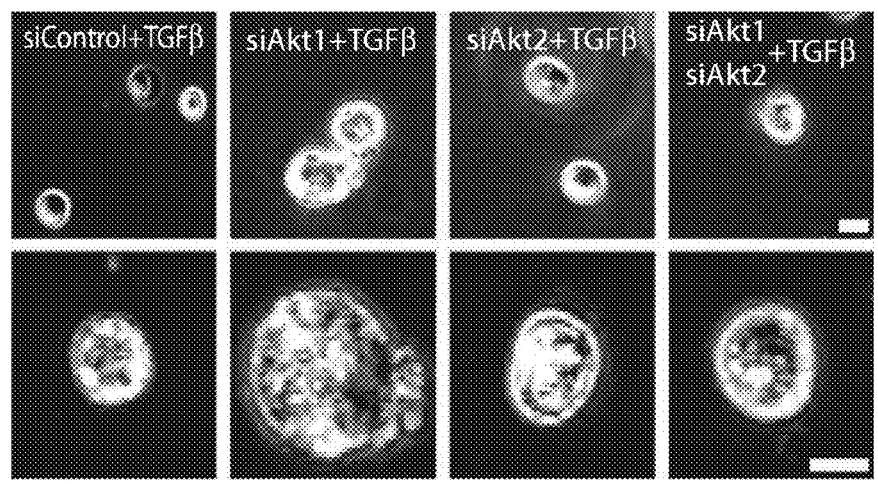
Figure 17C:
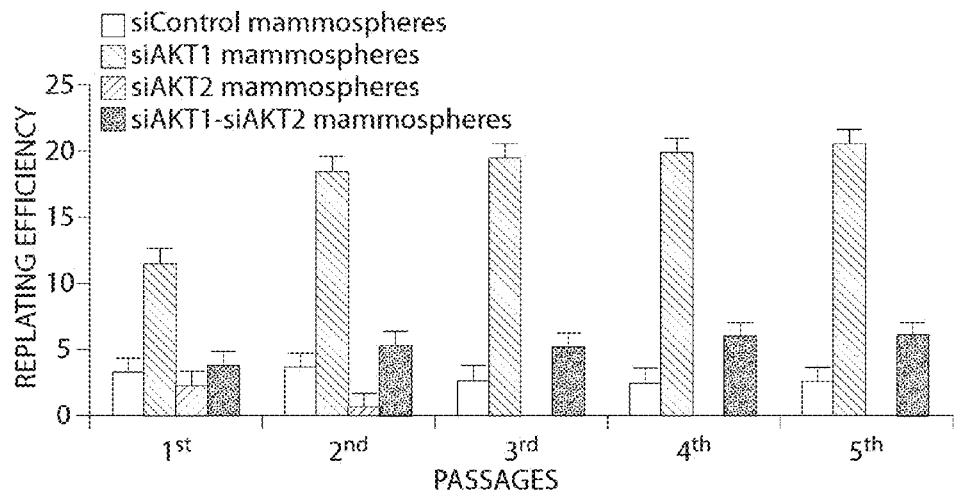
Figure 17D:
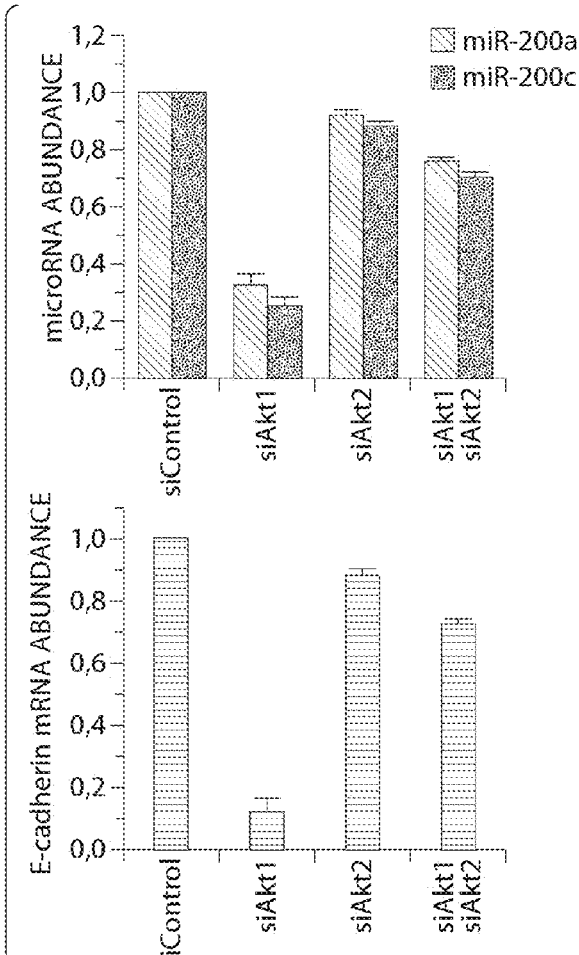
Figure 18:
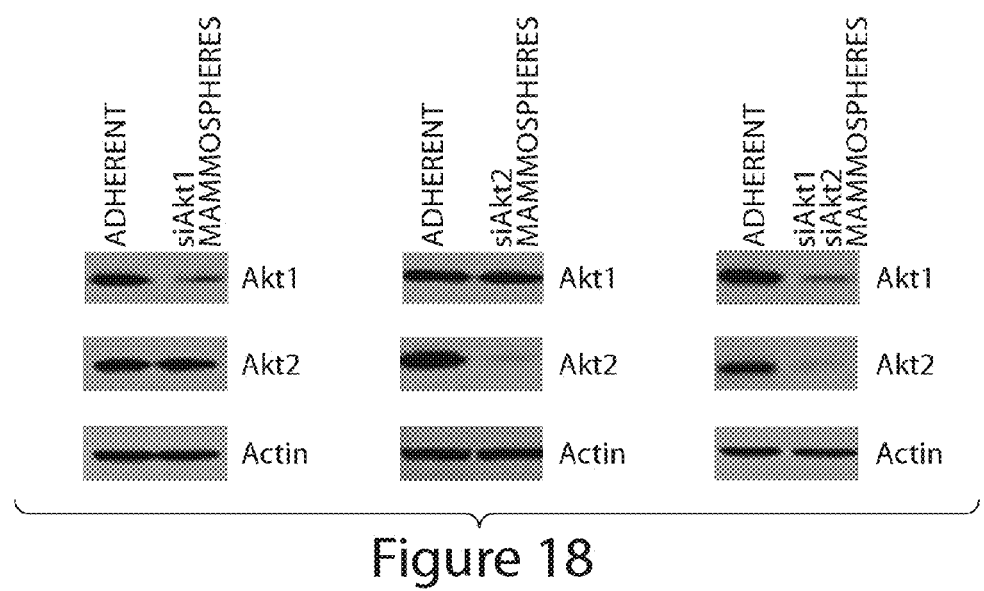
FIG. 18 is a set of photographs of immunoblots showing expression of Akt1 and Akt2 in adherent and non-adherent MCF10A cells treated with siRNAs for Akt1 and/or Akt2 (harvested on the 6th day of culture at passage 5). Mammosphere cells continued to show low amounts of Akt1 and/or Akt2, six days after transfection of the corresponding siRNAs. Beta actin levels were used as the loading control.
Figure 19A:
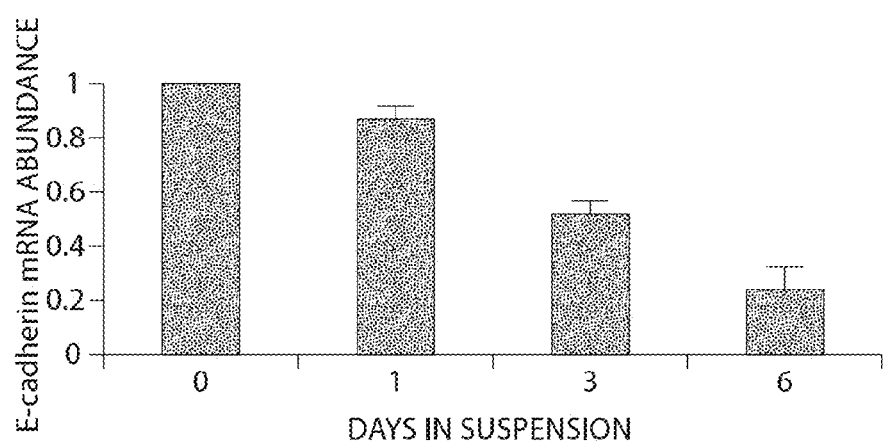
FIGS. 19A and 19B are a set of bar graphs showing E-cadherin (FIG. 19A) and Vimentin (FIG. 19B) mRNA abundance in MCF10A cells, harvested at consecutive days of culture in suspension. Cells were transfected with Akt1 siRNA and were cultured in media containing TGFβ (20 ng/ml). Cells at day 0 are adherent cells.
Figure 19B:
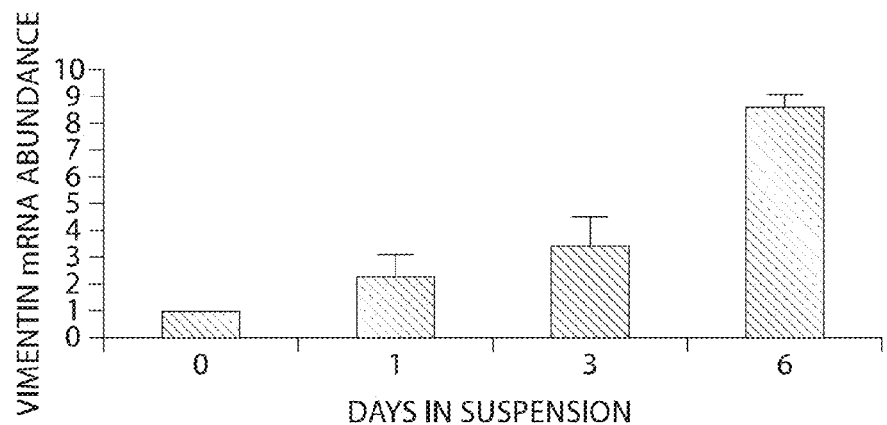

Knockdown of Akt1 and not Akt2 knockdown was found herein to promote formation of mammospheres which are three-dimensional structures formed by breast cancer stem cells grown in suspension (Dontu et al., 2003 Genes Dev. 17: 1253-1270) and by MCF10A cells (FIG. 17B). Furthermore, Akt1 knockdown synergized with TGFβ in promoting mammosphere formation (FIGS. 17A and 17B). Akt1 and Akt2 knockdown in MCF10A cells did not affect the abundance of the mRNAs encoding the nontargeted isoforms and persisted for more than 6 days after siRNA transfection (FIG. 18). Mammospheres in the Akt1 siRNA-treated cultures were larger than those in cultures treated with control siRNA; in addition, they showed higher re-plating potential and decreased abundance of miR-200a, miR-200c, and the mRNA encoding E-cadherin (FIGS. 17B to 17D). In the same mammospheres, the abundance of E-cadherin mRNA progressively decreased and the abundance of vimentin mRNA progressively increased over a 6-day period (FIG. 19).

Thus, Akt1 knockdown elicits a cancer stem cell-like phenotype, an observation consistent with the hypothesis that cells undergoing EMT acquire cancer stem cell properties (Mani et al., 2008 Cell 133: 704-715). Examples herein show that a decrease in miR-200 abundance after a shift in the balance between Akt1 and Akt2 promotes a cancer stem cell-like phenotype.

Example 15

Mammary Adenocarcinomas in MMTV-ErbB2/Akt1$^{-/-}$ Mice Have Low Abundance of microRNAs of the miR-200 Family, High Abundance of Zeb1, and Low Abundance of E-Cadherin Expression of either ErbB2 or PyMT in the mammary gland of transgenic mice from mouse mammary tumor virus long terminal repeat (MMTV LTR)-driven transgenes causes mammary adenocarcinomas. Mammary adenocarcinomas that develop in MMTV-cErbB2/Akt1$^{-/-}$ mice were more invasive than those arising in MMTV-cErbB2/Akt1$^{+/-}$ mice, as determined by histological examination of the tumors; moreover, MMTVcErbB2/Akt1$^{-/-}$ tumors may have a greater potential for metastasis (Maroulakou et al., 2007 Cancer Res. 67: 167-177).

Figure 20A:
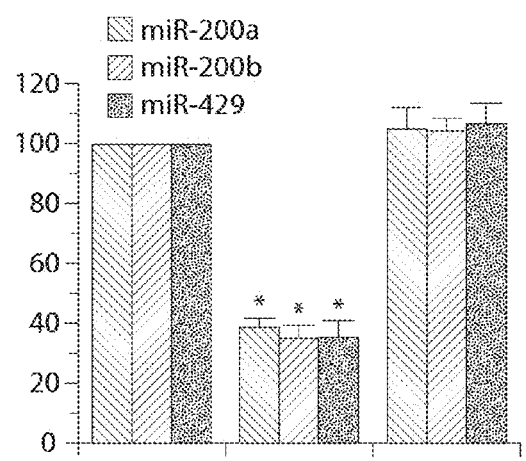
FIGS. 20A-20D are a table, a set of photographs of immunoblots, a set of bar graphs and photographs showing that mammary adenocarcinomas developing in MMTV-cErbB2/Akt1$^{-/-}$ mice have low amounts of microRNAs of the miR-200 family, high amounts of Zeb1, and low amounts of E-cadherin.
Figure 20B:
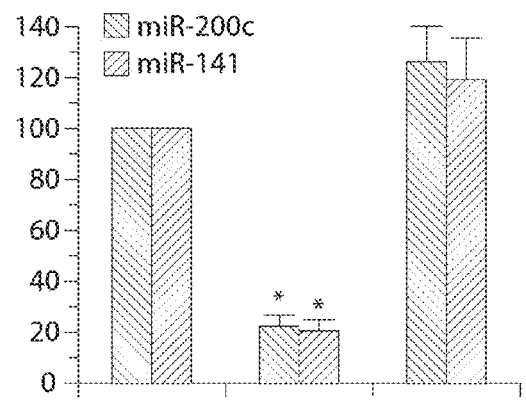
Figure 20C:
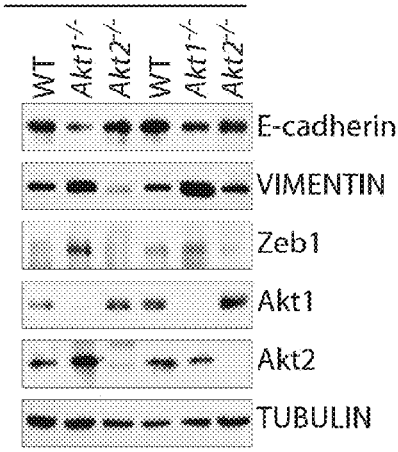
Figure 20D:
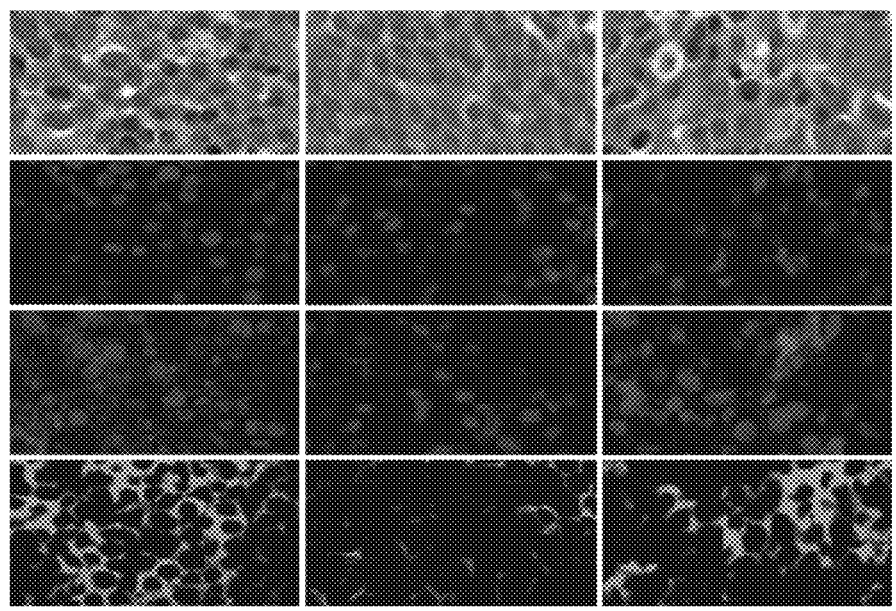
Figure 21A:
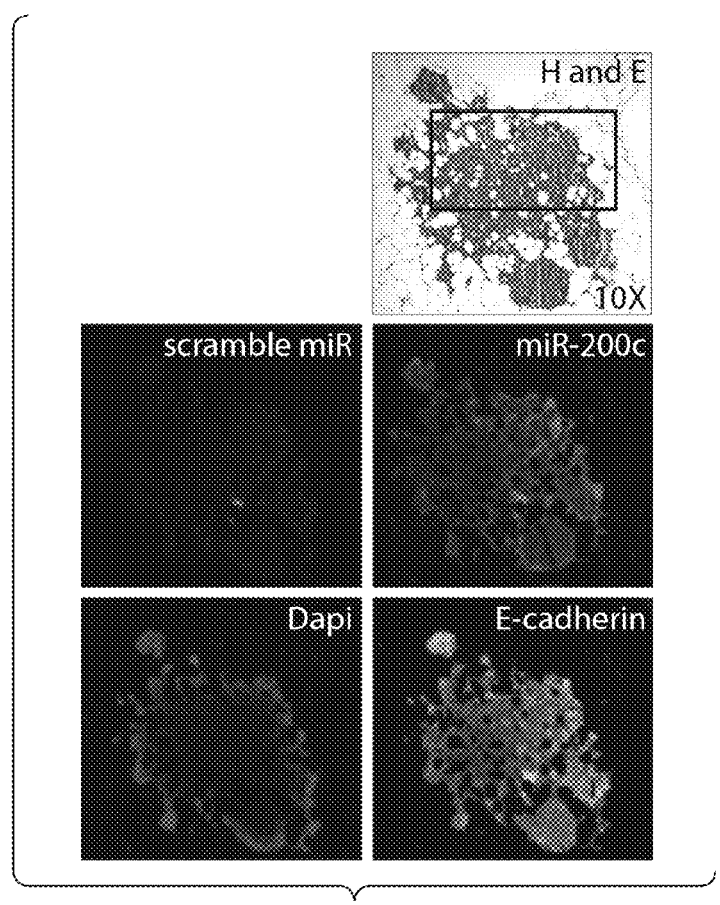
FIGS. 21A-21C are a set of microphotographs showing that MMTV-cErbB2-induced mammary adenocarcinomas expressed miR200c and E-cadherin.
Figure 21B:
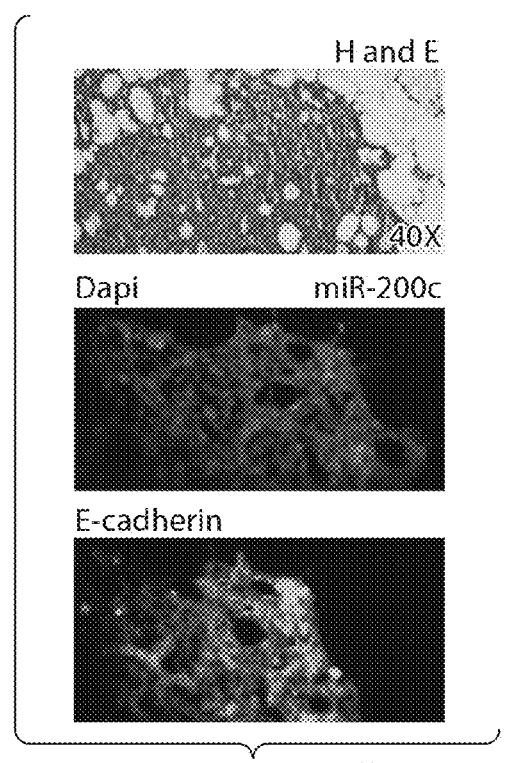
Figure 21C:
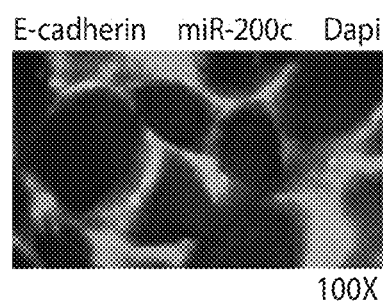
Figure 22:
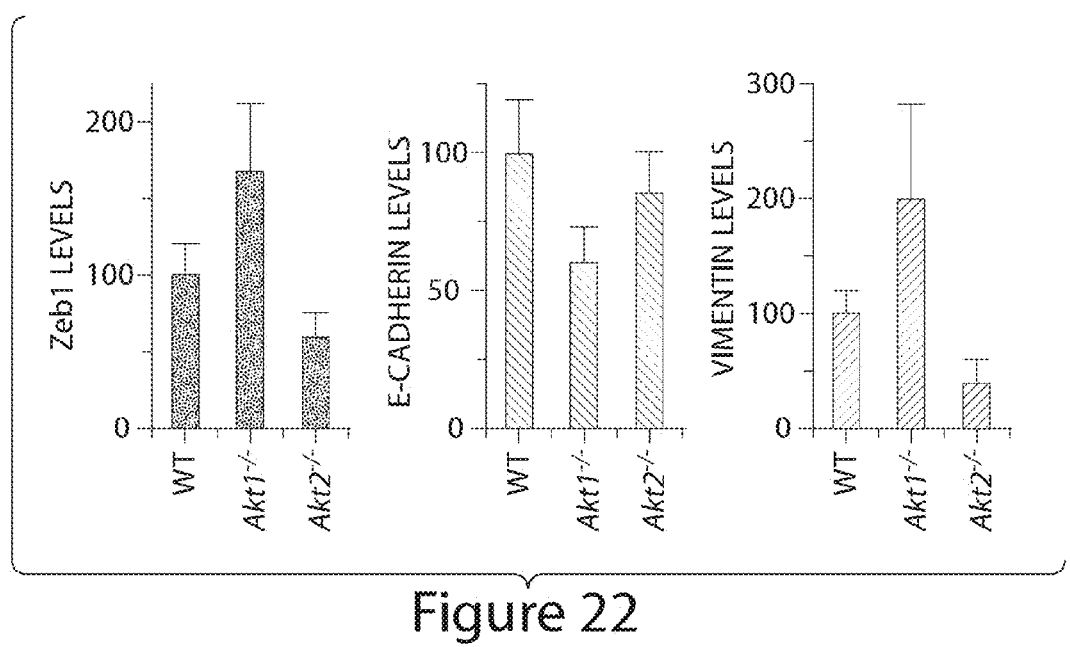
FIG. 22 is a set of bar graphs showing that MMTV-cErbB2/Akt1$^{-/-}$ mammary adenocarcinomas contained more Zeb1 and Vimentin and less E-cadherin than mammary adenocarcinomas developing in MMTV-cErbB2/Akt$^{-/-}$ and MMTV-cErbB2/Akt2$^{-/-}$ mice. Western blots of primary tumor cell lysates were probed with the indicated antibodies and protein abundance was quantified using the Scion Image analysis software. The quantity of each protein is expressed as the ratio of the protein to tubulin. In tumors arising in wild type mice, the ratio was arbitrarily set to 1 (n=3 mice per group).

Increased invasiveness of MMTV-cErbB2/Akt1$^{-/-}$ tumors was found herein compared to MMTV-cErbB2/Akt1$^{+/+}$ tumors (FIGS. 20A). Ablation of Akt1 was found to correlate with decreased abundance of the miR-200 microRNAs, as determined by real-time RT-PCR and in situ hybridization (FIGS. 20B and 20D, and FIG. 21). Loss of Akt1 in these tumors was also associated with an increase in the abundance of Zeb1 and vimentin and a decrease in that of E-cadherin, as determined by Western analysis (FIG. 20C and FIG. 22) and immunofluorescence (FIG. 20 panel D).

Example 16

The Akt-miR-200-E-Cadherin Axis Contributes to the Metastatic Phenotype of Human Mammary Adenocarcinomas Real-time (RT)-PCR was used to evaluate the abundance of miR-200a, miR200c, and the mRNAs encoding Akt1, Akt2, and E-cadherin in primary and metastatic tumor tissue from eight patients with breast cancer.

Figure 23A:
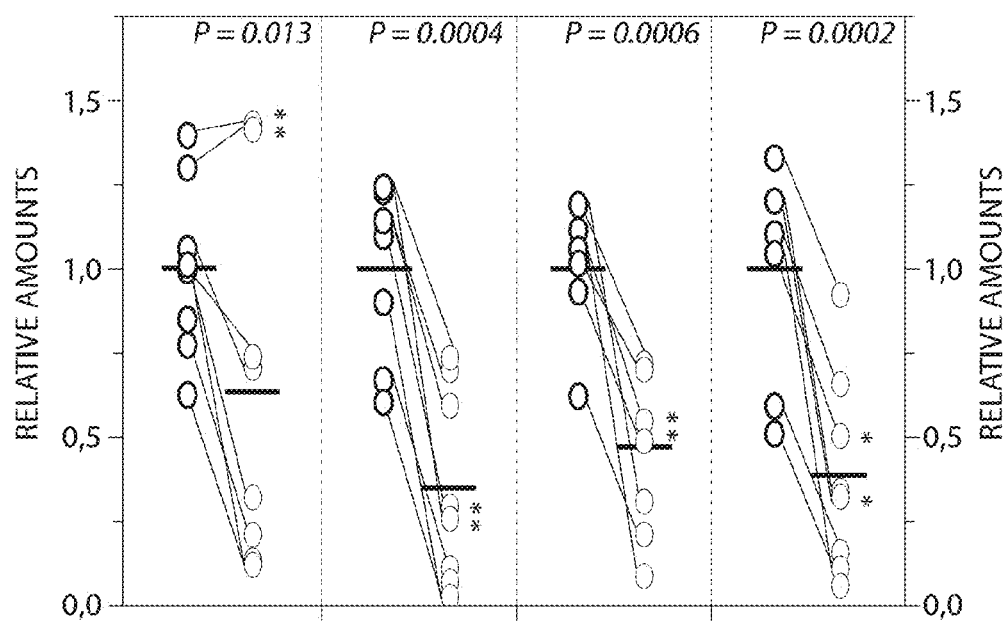
FIGS. 23A and 23B are a set of line graphs and bar graphs showing the Akt-miR-200-E-cadherin axis contributes to the metastatic phenotype in most human mammary adenocarcinomas.
Figure 23B:
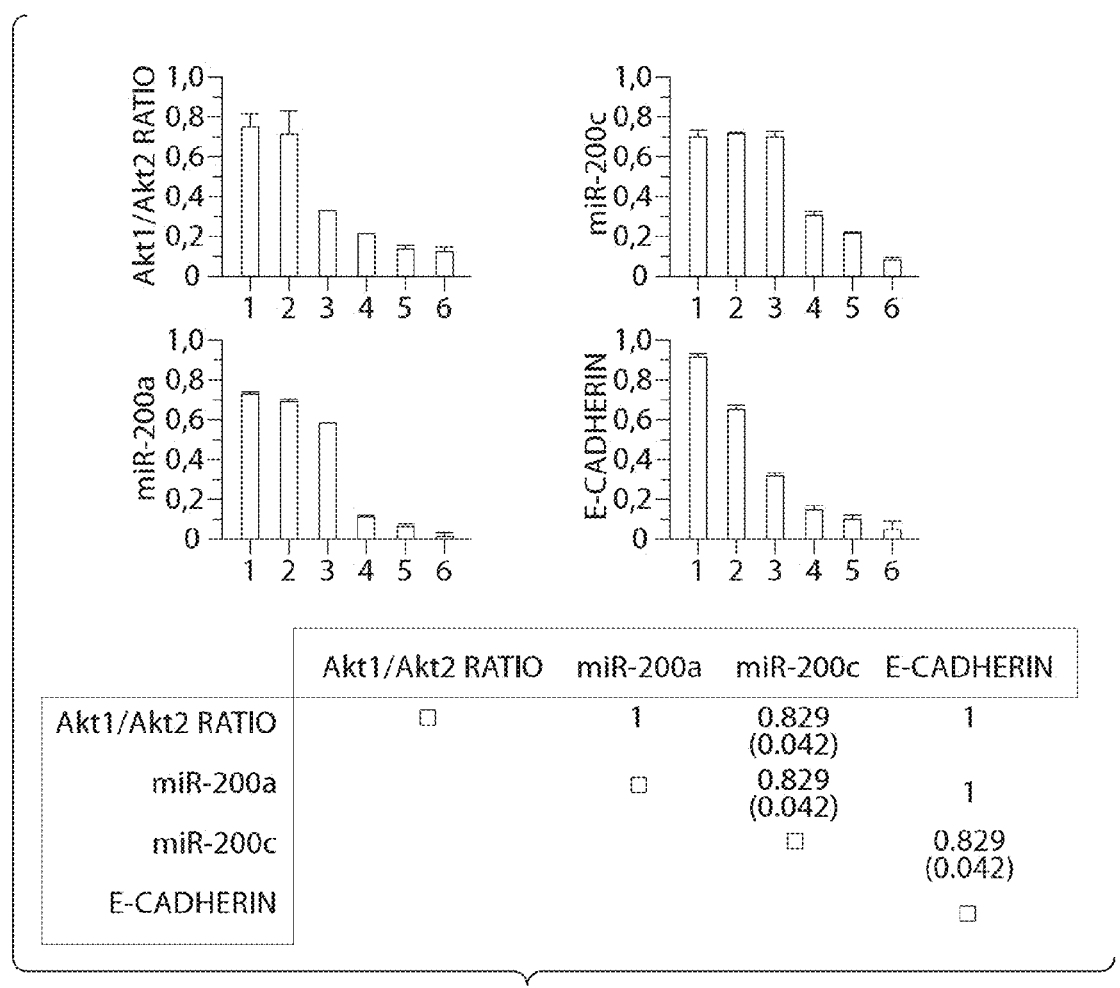

The ratio of Akt1 to Akt2 was found in many cases to be lower in metastatic than in primary tumor tissue. In two cases the ratio of Akt1 to Akt2 was high in both the primary and the metastatic tissue. The abundance of miR-200a, miR-200c, and the mRNA encoding E-cadherin was significantly lower in the metastatic tumors (FIG. 23A). Examples herein show that decreased abundance of the miR-200 microRNA family and of E-cadherin are common features of metastatic human breast cancer and that this decrease is associated with a decrease in the ratio of Akt1 to Akt2. The values of Akt1/Akt2, miR-200a, miR-200c, and E-cadherin were plotted for six metastatic tumors in which the Akt1/Akt2 ratio was low and found an excellent correlation between these values, which was confirmed herein by the Spearman rank correlation statistical test (FIG. 23B).

Examples herein show that breast cancer metastasis frequently depends on signaling through the Akt-miR-200-E-cadherin axis. As the ratio of Akt1 to Akt2 was low in some primary tumors, it is important to determine whether a low Akt1-to-Akt2 ratio has prognostic value for predicting metastasis.

Example 17

Targeting Akt Isoforms as a Platform for Preclinical Testing of Specificity of Akt Inhibitors Examples herein show that after ablation of the floxed Akt1 allele, spontaneously immortalized Akt1$^{fl/fl}$/Akt2$^{-/-}$/Akt3$^{-/-}$ lung fibroblasts survived for about a week and failed to proliferate. Cells reconstituted with the three Akt isoforms survived and proliferated, showing that Akt1, Akt2, and Akt3 overlap functionally. Further, comparison of cells reconstituted with Akt1, Akt2, or Akt3 also showed functional differences. Examples herein show marked differences in microRNA signature between IGF1- or TGFβ-treated cells expressing different Akt isoforms. In addition, stimulation of cell migration was shown to be induced by the knockdown of Akt1 and not Akt2 in cultured cells and the invasive phenotype was shown to be induced by the ablation of Akt1 and not Akt2 in primary tumors due to the differential effects of Akt1 and Akt2 on the abundance of the miR-200 microRNA family.

Examples herein show the invasiveness and metastatic potential of human carcinomas depends on the balance between Akt1 and Akt2 and not on the expression and activity of Akt. A shift in the relative abundance or activity of Akt1 and Akt2 alters the abundance of members of the miR-200 microRNA family and, consequently, the invasiveness and oncogenic potential of human tumors. Such a shift occurs naturally (Padmanabhan et al., 2009 Cell 136: 939-951), or it is elicited by Akt inhibitors that preferentially target Akt1 rather than Akt2. Examples herein show ways to harness the beneficial effects of Akt1 inhibition, while preventing Akt1 unwanted effects on tumor cell invasiveness and metastasis, by combining Akt1 inhibition with delivery of microRNAs of the miR-200 microRNA family.

Figure 24:
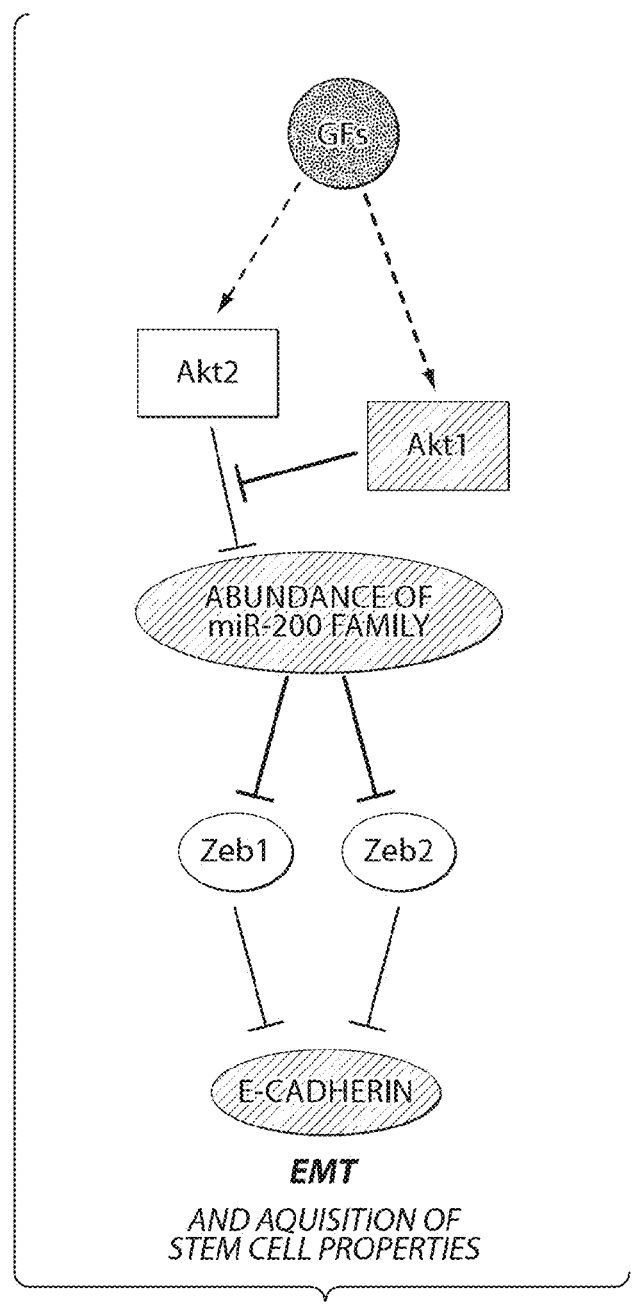
FIG. 24 is a schematic diagram of a model showing the imbalance between Akt1 and Akt2 dysregulates microRNAs that control EMT and stein cell renewal programs. Dark gray color indicates a positive and light gray indicates a negative role in the development of EMT and acquisition of stem cell properties. GFs, growth factors.

The regulation of the miR-200 microRNA family, through the concerted action of Akt1 and Akt2, depends on the crosstalk between the two Akt isoforms (see model in FIG. 24). This model was based on the finding herein that Akt2, in the absence of Akt1, decreased the abundance of the miR-200 microRNA family and that Akt1 attenuated the Akt2-mediated decrease in the abundance of these microRNAs; however, Akt1 had no Akt2-independent effects on miR-200 family abundance. Based on these observations, Akt1 was shown herein to regulate Akt2 or interfere with the Akt2-mediated decrease in miR-200 microRNA abundance downstream of Akt2. In either case, the role of Akt1 in miR-200 regulation is Akt2 dependent.

The data in Examples herein show that the balance between Akt1 and Akt2 is critical to the regulation of microRNA gene expression and that the opposing roles of Akt1 and Akt2 on the induction of EMT are due to the differential effects of the two Akt isoforms on the expression of the miR-200 microRNA family.

Example 18

Determining the Biological Properties of Akt-Null Cells and Cells Expressing Different Akt Isoforms Examples herein show that the three Akt isoforms differ in their ability to regulate cell proliferation and cell survival under normal growth conditions and in response to stress. The nature of these differences is investigated herein.

Examples herein show the role of Akt1 and Akt2 in the regulation of microRNAs that control EMT. Further, the data obtained from lung fibroblast system are directly applicable to human mammary epithelial cells in which Akt1 and/or Akt2 were knocked down. Examples described herein are carried out in both the lung fibroblast system and in human mammary epithelial (MCF10A) cells. To knockdown Akt1 Akt2 and/or Akt3 in MCF10A cells, the cells are infected with inducible Akt1, Akt2 and/or Akt3-specific shRNA constructs in the lentiviral vector pSLIK (Shin et al., 2006 Proc. Natl. Acad. Sci. U.S.A. 103: 13759-13764). Cells infected with different shRNA constructs are used in subsequent Examples after confirmation of the efficient and specific knockdown of Akt1, Akt2 or Akt3 by doxycycline. The two systems make use of different cell types (fibroblasts compared to epithelial cells). In addition, these systems differ in that individual Akt isoforms are knocked out chronically in one system (lung fibroblasts) or acutely in the other (MCF10A cells). The data obtained from two systems are therefore complementary to each other.

Example 19

Figure 25A:
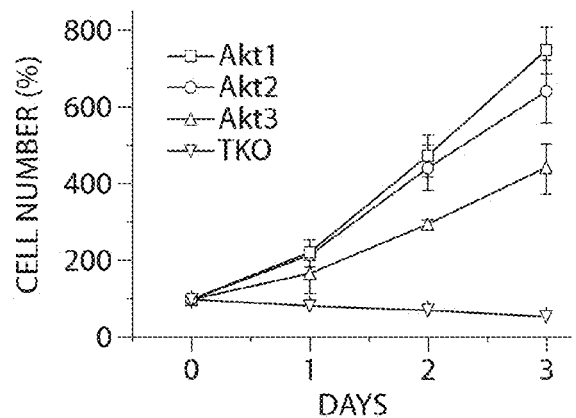
FIGS. 25A-25C are a set of line graphs, photographs of immunoblots and a bar graph showing that Akt3 expressing cells grow slowly relative to Akt1-expressing cells, and Akt2-expressing cells exhibit an intermediate growth phenotype. The growth of Akt1, Akt2 and Akt3-expressing cells exhibits a negative correlation with the expression of p53 and its target miR-34 (a, b and c).

Proliferation and Survival of Cells Growing under Normal Tissue Culture Conditions Growth curves of cells expressing no Akt, or Akt1, Akt2 or Akt3 showed that Akt3 expressing cells grow slowly relative to Akt1-expressing cells, while Akt2-expressing cells exhibit an intermediate growth phenotype. Akt null cells do not proliferate. Instead, their numbers decrease slowly because of decreasing survival over time. The number of Akt3-expressing cells is lower from day one. However, while the numbers of Akt1 and Akt2-expressing cells are similar during the logarithmic phase of growth (day 1 and day 2), they begin to diverge once the cultures become confluent (day 3; FIG. 25A). These data have been reproduced multiple times with similar results each time. In other examples Akt3-expressing cells passaged in culture were shown to express progressively lower levels of Akt3, showing that cells expressing high levels of Akt3 are counter-selected in culture. Similar results were also observed in Akt2-expressing cells.

Figure 25B:
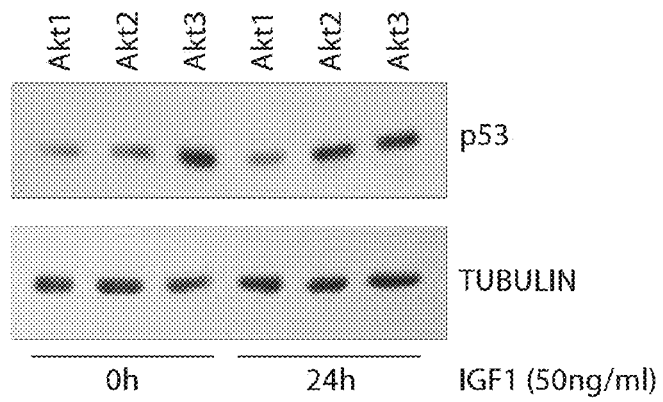

Other studies (Wright et al., 2008 FASEB J. 22: 3264-3275) showed that Akt (primarily Akt3, and to a lesser degree Akt2), promote the upregulation of reactive oxygen species (ROS). Since high levels of ROS up-regulate p53 by inducing DNA damage (Xie et al., 2001 J. Biol. Chem. 276: 36194-36199), the expression of p53 before and after stimulation with IGF1 was examined herein. The results in FIG. 25B show that Akt3-expressing cells express high levels of p53 and that 24 hours after IGF stimulation, the Akt2 expressing cells also express high levels of p53. Since p53 is a positive regulator of the growth inhibitory microRNA family miR-34

Figure 25C:
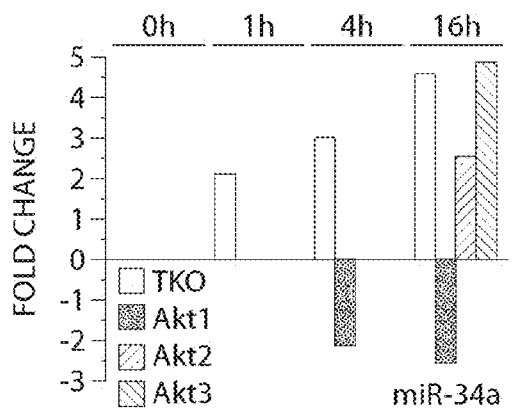

(miR-34a, miR-34b and miR-34c) (He et al., 2007 Nature 447:1130-1134), the expression of the members of this family is examined by real time RT-PCR. FIG. 25C shows that miR-34a is up-regulated by IGF in Akt3-, and to a lesser degree in Akt2-expressing cells and it is down-regulated in Akt1-expressing cells. Examples herein describing the expression of miR-34b and miR-34c confirmed the microRNA array data in FIGS. 2 and 3.

Examples herein show that Akt3 inhibits cell proliferation (or reduces efficiency relative to effects of Akt1 or Akt2 in promoting cell proliferation), primarily because of p53-dependent inhibition of proliferative signals during the logarithmic phase of growth, Akt2 is more efficient than Akt1 in the transduction or interpretation of antiproliferative signals induced by cell to cell contact in confluent cultures.

When plated, cells initially proliferate logarithmically. Once the culture become confluent, they stop to proliferate because of contact inhibition. A major inhibitory pathway that is known to be activated by cell to cell contact is the Hippo pathway (Zeng et al. 2008 Cancer Cell 13: 188-192). Examples herein shows that Akt1- and Akt2-expressing cells exhibit similar growth rates until they reach confluency (FIG. 25A), at which point the inhibition of the Akt2-expressing cells is more pronounced. Akt3-expressing cells exhibit a significant growth delay throughout. Examples herein shows cell growth extending the growth curves up to 5 days from the day of plating are performed to determine the time point at which the cultures of Akt1-, Akt2- and Akt3-expressing cells exhibit the most pronounced differences in cell number. This time point provides significant information regarding the mechanism responsible for the difference. Differences during the logarithmic phase of growth show that the cells exhibit differential responses to growth factor and other proliferative signals, and that at the time the cells approach confluency the cultures differ in ability to transduce or interpret inhibitory signals induced by cell to cell contact. In either case the cell number data are due to differences in the rates of proliferation and/or death.

Once the time point at which the most pronounced growth differential between the cells expressing different Akt isoforms is identified, the data on harvesting the cells at this time point is repeated, as well as at an earlier or later time point, at which the differences are less pronounced. The nuclei of the harvested cells are then stained with propidium iodide (PI) and the DNA content of the cells is examined by flow-cytometry. Cells harvested from parallel cultures are exposed to ethidium bromide (EtBr) and they are again analyzed by flow cytometry to determine the percentage of cells that take up EtBr (dead cells). Parallel cultures are exposed to Brdu prior to harvesting. Brdu incorporation into the DNA (a measure of DNA synthesis) is examined by antibody staining and flow cytometry. Akt null cells serve as controls in the preceding Examples.

The data show whether the differences in growth between cells expressing different Akt isoforms are due to differences in cell proliferation, to differences in cell survival, or to both. In addition, they show whether the differences are due to the transduction or interpretation of proliferative signals during the logarithmic phase of growth, or to differences in the response to inhibitory signals induced by cell to cell contact in confluent cultures.

To further explore the mechanism responsible for differences in cell proliferation, cells are synchronized at the time point the differences in cell proliferation are most pronounced, as well as at an earlier or later time point at which the differences are less pronounced. The DNA content of the nuclei of cells harvested at sequential time points following the release of the cells from the synchronization block is examined again by PI staining and flow cytometry. The cells are synchronized by serum starvation, which arrests the cells in G1, by double thymidine block which arrest cells in S, and by nocodazole block which arrest cells in G2/M (Davis et al., 2001 Biotechniques 30: 13322-13326). To determine the mechanisms of potential differences in cell survival, TUNEL assays are carried out, which measure the rate of apoptosis (Heatwole, 1999 Methods in Mol. Biol. 115: 1064-3745). To determine whether cells expressing different Akt isoforms exhibit differences in autophagy, western blots of cell lysates harvested at the same time points as above are probed with a monoclonal antibody specific for the autophagosome protein LC3. Alternatively, the cells with a GFP fusion of LC3 are transduced, and subcellular localization of the GFP fusion is monitored by confocal microscopy. Autophagy is characterized by the incorporation of LC3 into the autophagosomes and by the subsequent cleavage of the 17 KD LC3-I isoform to the 15 KD LC3-II isoform (Mizushima, 2007 Autophagy: Process and function Genes and Development 21: 2861-2873). Both the redistribution and the cleavage of LC3 are monitored to provide a quantitative comparison between cells expressing different Ala isoforms.

Signaling and gene expression differences explain the biological differences between cells expressing different Akt isoforms. To this end, cultures parallel to the ones described in the preceding Examples herein are harvested at the same time points and cell lysates are probed with phosphospecific and total antibodies against TSC2, mTOR, p70S6K, 4EBP, GSK3, IRS1, ERK, PTEN, Rb, p53, FOXO3A and FOXO1 (Manning et al., 2007 Cell 129: 1261-1274).

Example 20

Figure 26A:
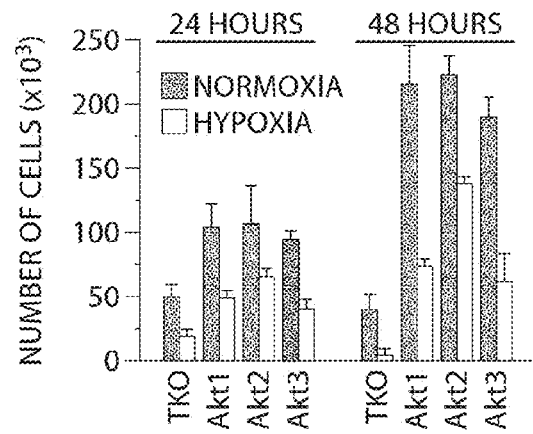
FIGS. 26A-26E are a set of bar graphs and histograms showing that Akt2-expressing cells are more resistant to hypoxia, than Akt1 or Akt3 expressing cells
Figure 26B:
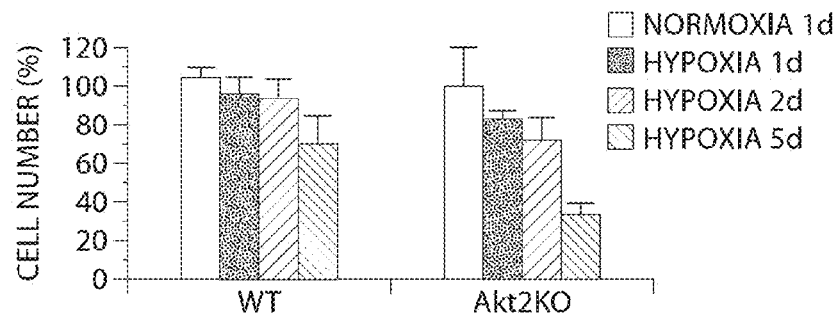
Figure 26C:
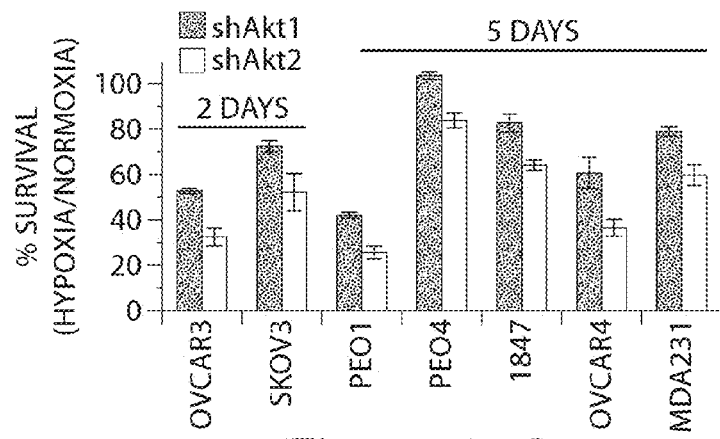
Figure 26D:
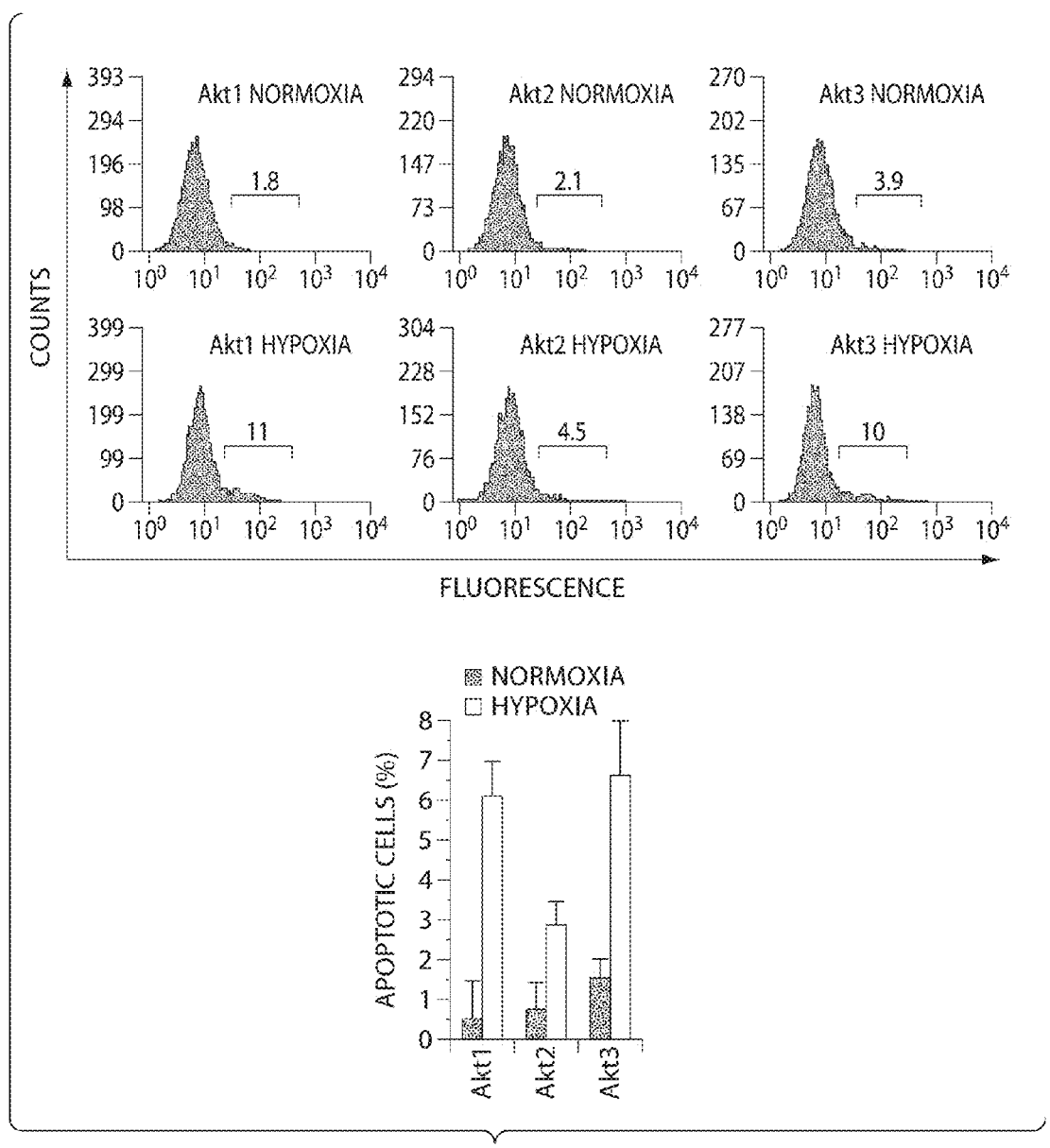
Figure 26E:
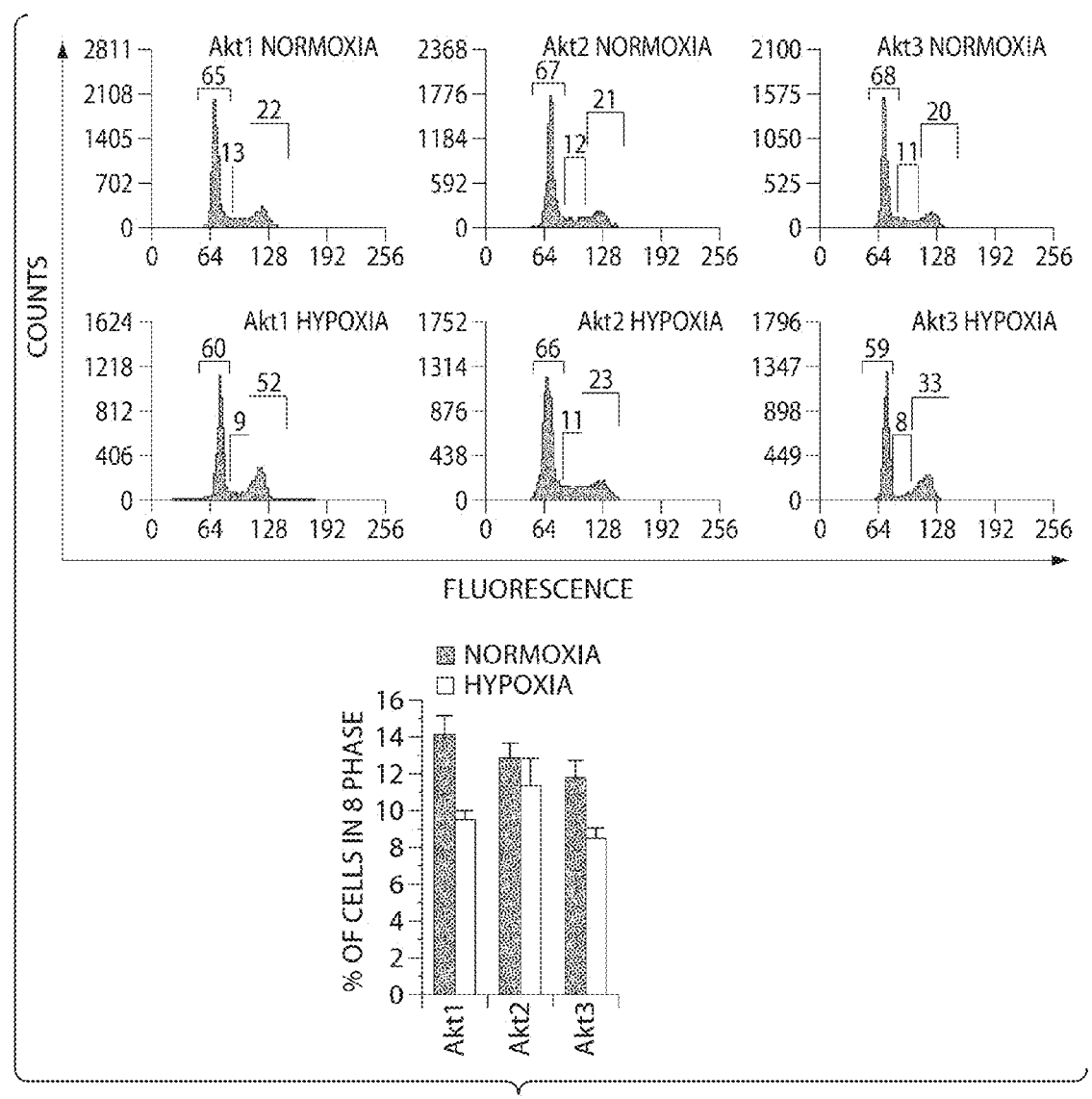

Akt2-Expressing Cells are more Resistant to Hypoxia, than Akt1 or Akt3 Expressing Cells Immortalized triple Akt knockout lung fibroblasts, generated as described in the Examples herein, and their derivatives expressing only Akt1, Akt2, or Akt3, were exposed to hypoxia (0.1/oxygen) for 24 or 48 hours. Comparison of the relative numbers of cells surviving under hypoxia in these cultures showed that Akt2-expressing cells survive significantly better, compared to the triple Akt knockouts, and also to the Akt1 and the Akt3-expressing cells (FIG. 26A). The same procedure performed in primary MEFs showed that Akt2$^{-/-}$ MEFs exhibit significant sensitivity to hypoxia, relative to wild type MEFs (FIG. 26B).

To determine whether Akt2 protects tumor cells also from hypoxia, seven human ovarian or mammary carcinoma cell lines were transduced with Akt1 or Akt2 shRNA constructs and the resistance of the transduced cells to hypoxia was examined. To measure cellular resistance, the ratio of live cells in cultures exposed to hypoxia and cultures maintained in normoxia was calculated herein. The results showed that cells transduced with the Akt2 shRNA were reproducibly more sensitive to hypoxia than cells transduced with the Akt1 shRNA.

To determine the mechanism of the Akt2-mediated protection from hypoxia, first the TUNEL assay was used to measure the numbers of apoptotic cells before and after exposure of the lung fibroblast cultures to hypoxia. The results showed that Akt2 protects cells from hypoxia-induced apoptosis (FIG. 26B). In parallel, the role of Akt2 was examined in cell cycle progression in cultures of the same cells exposed to hypoxia. The results showed a significant drop in the percentage of S phase cells, without significant changes in the percentage of G1 and G2M phase cells in Akt1 and Akt3-expressing cultures, upon oxygen deprivation. In Akt2-expressing cultures on the other hand, the percentage of S phase cells remained essentially unchanged upon exposure to hypoxia, while the percentage of G2M phase cells was increased and the percentage of G1 phase cells was reciprocally decreased.

These data collectively showed that the Akt1 and Akt3-expressing cells exposed to hypoxia undergo apoptosis as they progress through S phase or they undergo apoptosis with a parallel G1/S phase block. Akt2-expressing cells on the other hand, experience a G2M phase block upon exposure to hypoxia, and the cells are protected from cell death.

Example 21

The Differential Sensitivity of Akt1, Akt2 and Akt3-Expressing Cells to Hypoxia is Due to the Differential Induction of miR-21

MicroRNAs are differentially regulated by Akt1, Akt2 and Akt3 in growth factor-treated cells. MicroRNAs may also be differentially regulated by the three Akt isoforms in cells exposed to hypoxia. A microRNA that plays an important role in a variety of human cancers, and which is upregulated by hypoxia is miR-21.

Using real time PCR to determine expression of miR-21 in immortalized triple Akt knockout lung fibroblasts and their derivatives expressing Akt1, Akt2, or Akt3, observed before and after exposure in hypoxia, it was observed that hypoxia induced miR-21 only in Akt2-expressing cells (FIG. 27A left). Comparison of miR-21 induction in wild type and Akt2$^{-/-}$ primary MEFs exposed to hypoxia showed that miR-21 is only induced in wild type cells, (FIG. 27A right) and confirmed that Akt2 is required for induction of miR-21 by hypoxia.

Figure 27C:
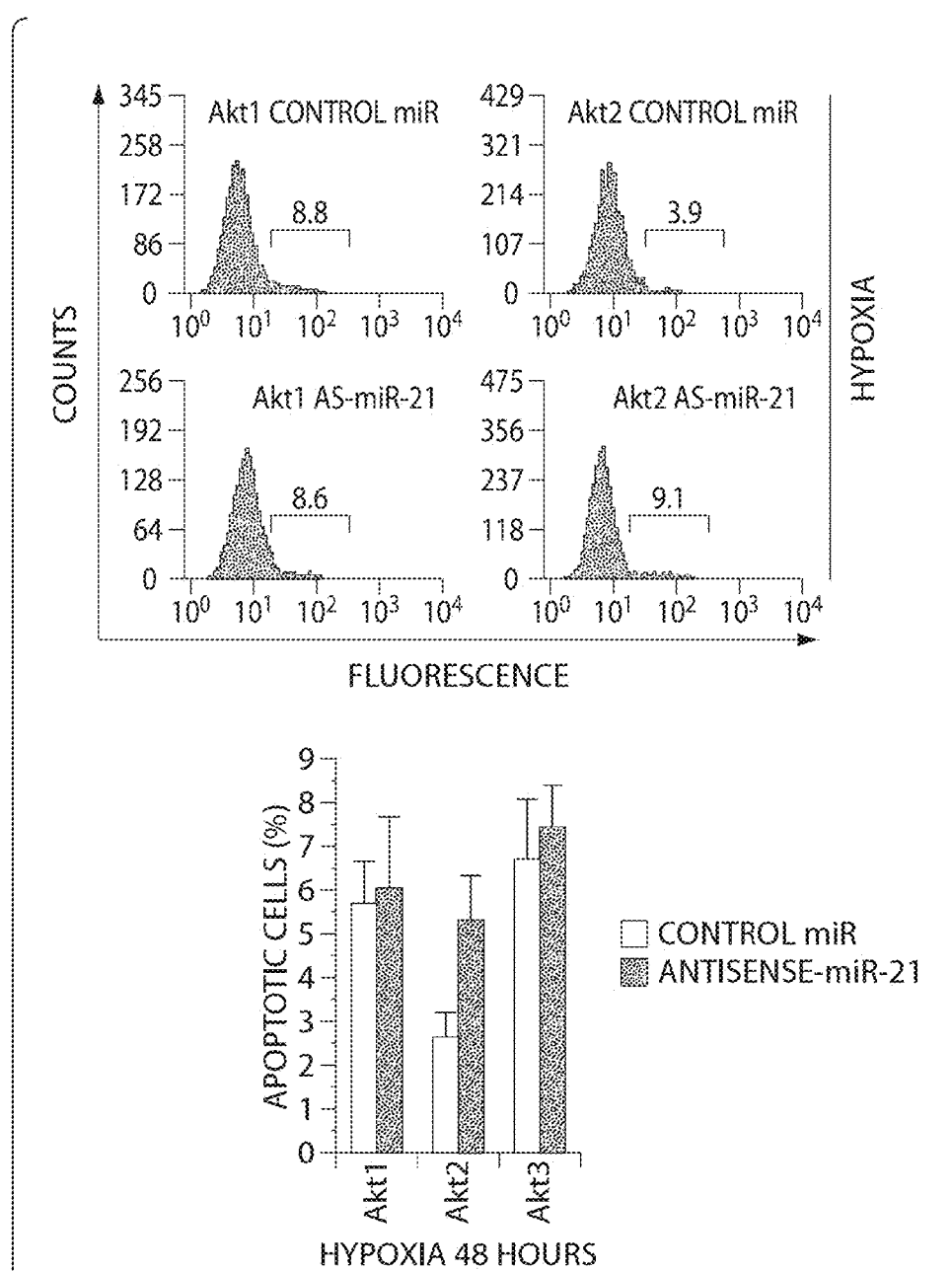

To determine whether miR-21 is necessary and sufficient for the growth advantage of oxygen-deprived Akt2-expressing cells, Akt1, Akt2 and Akt3-expressing lung fibroblasts were transfected with anti-miR21 or control miR, and cell numbers were examined before and 48 hours after exposure to hypoxia. The results showed that the control miR-transfected Akt2-expressing cells were protected from hypoxia, and the anti-miR-21-transfected Akt2-expressing cells were sensitive. Transfection of pre-miR-21 on the other hand, rendered the cells, including the Akt1 and Akt3-expressing cells, resistant to hypoxia (FIG. 27B). In parallel, primary wild type and Akt2$^{-/-}$ MEFs were transfected with anti-miR-21 or with pre-miR-21 and the survival of the transfected cells upon exposure to hypoxia was examined. The results confirmed that transfection of anti-miR-21 in wild type cells renders them as sensitive to hypoxia as the Akt2 expressing cells. Moreover, transfection of pre-miR-21 in Akt2$^{-/-}$ MEFs renders them as resistant to hypoxia as the wild type cells (FIG. 27C).

Figure 27D:
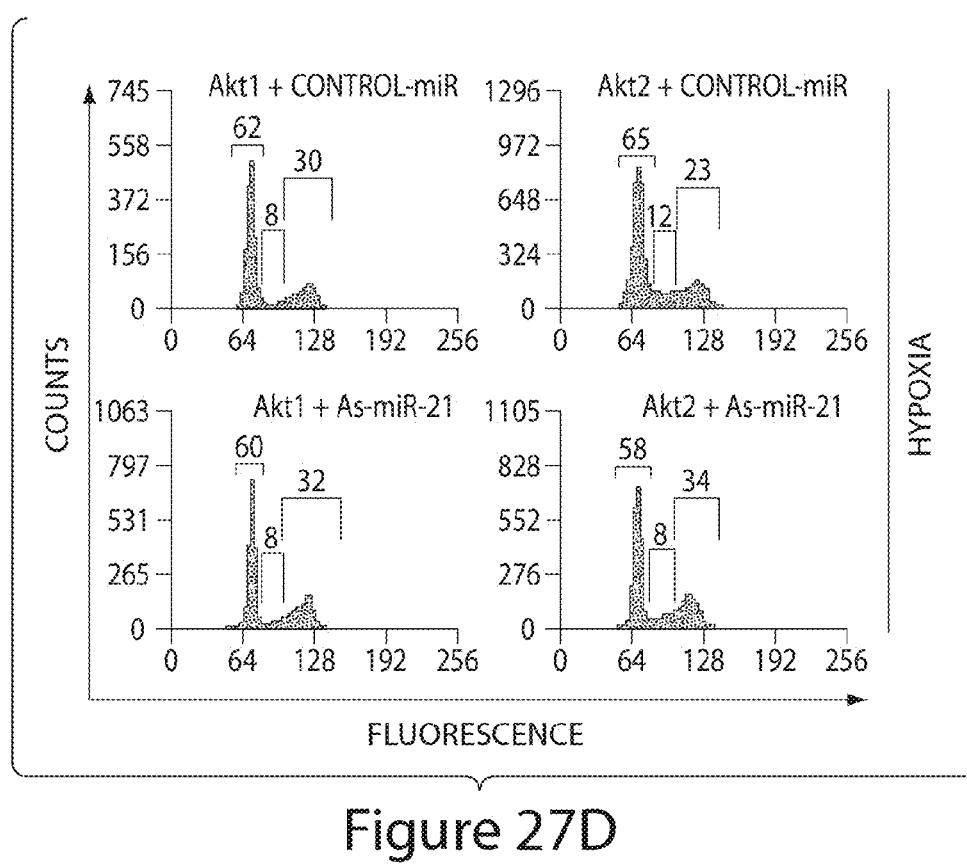

To analyze the mi-R21 mechanism of action, Akt1, Akt2 and Akt2-expressing lung fibroblasts were transfected with anti-miR-21 or pre-miR21, and the rate of apoptosis and the cell cycle distribution of the transfected cells was examined before and after exposure to hypoxia. The results (FIGS. 27C and 27D) showed that anti-miR21 interferes with the antiapoptotic phenotype and with the cell cycle phenotype of oxygen-deprived Akt2-expressing cells and that pre-miR-21 simulates the Akt2 phenotype in Akt1 and Akt3-expressing cells.

Example 22 miR-21 Regulates PTEN Expression and Akt Activation and Akt2 is a Global Regulator of Akt During Hypoxia by Regulating PTEN by miR-21 miR-21 is an oncogenic microRNA that is known to play an important role in the induction and progression of many human tumors. One of its targets is the D3 phospho-inositide phosphatase PTEN. Given the importance of PTEN in the activation of Akt and the importance of Akt in the regulation of apoptosis and cellular proliferation, the levels of PTEN and the activity of Akt in Akt1, Akt2 and Akt3-expressing cells were determined before and after exposure to hypoxia.

Figure 28A:
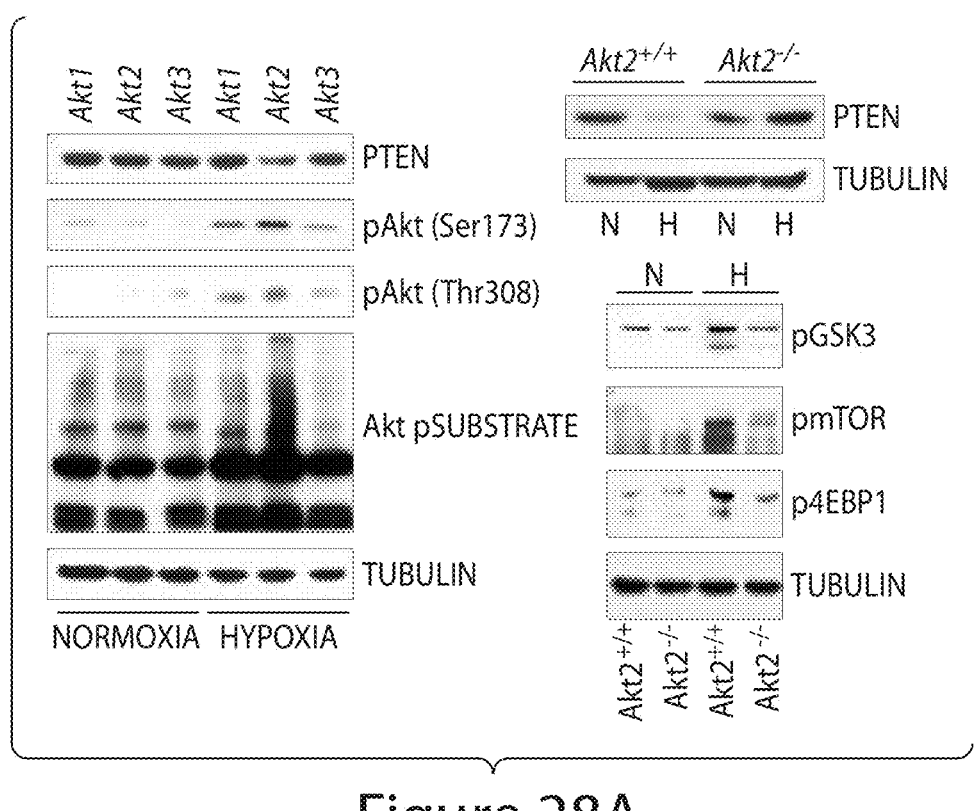
FIGS. 28A-28D are a set of photographs of immunoblots and bar graphs showing Akt2 through miR-21 regulates PTEN levels and Akt activity under hypoxia.
Figure 28B:
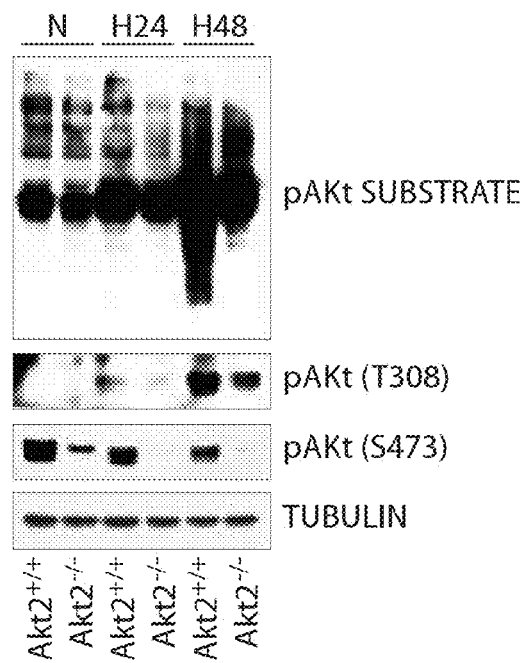
Figure 28C:
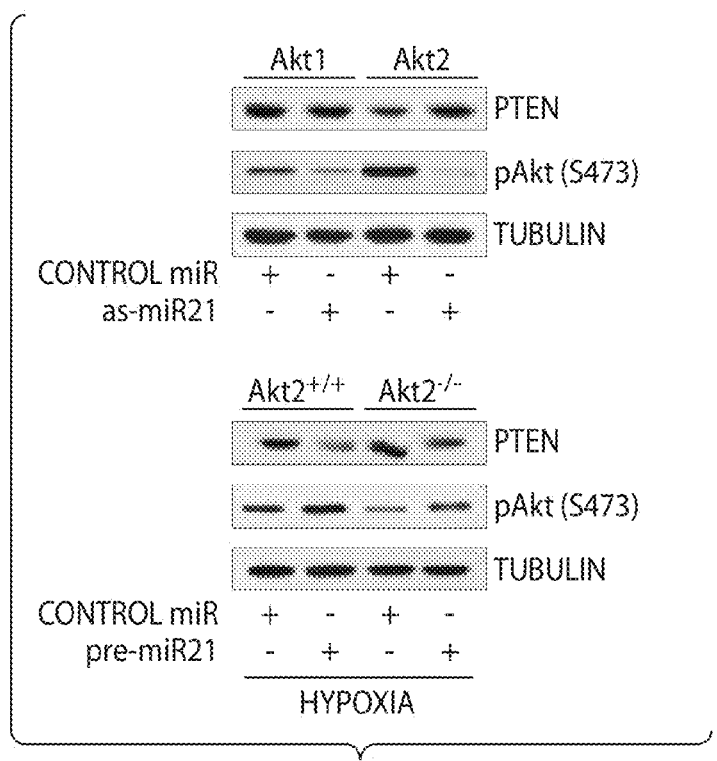
Figure 28D:
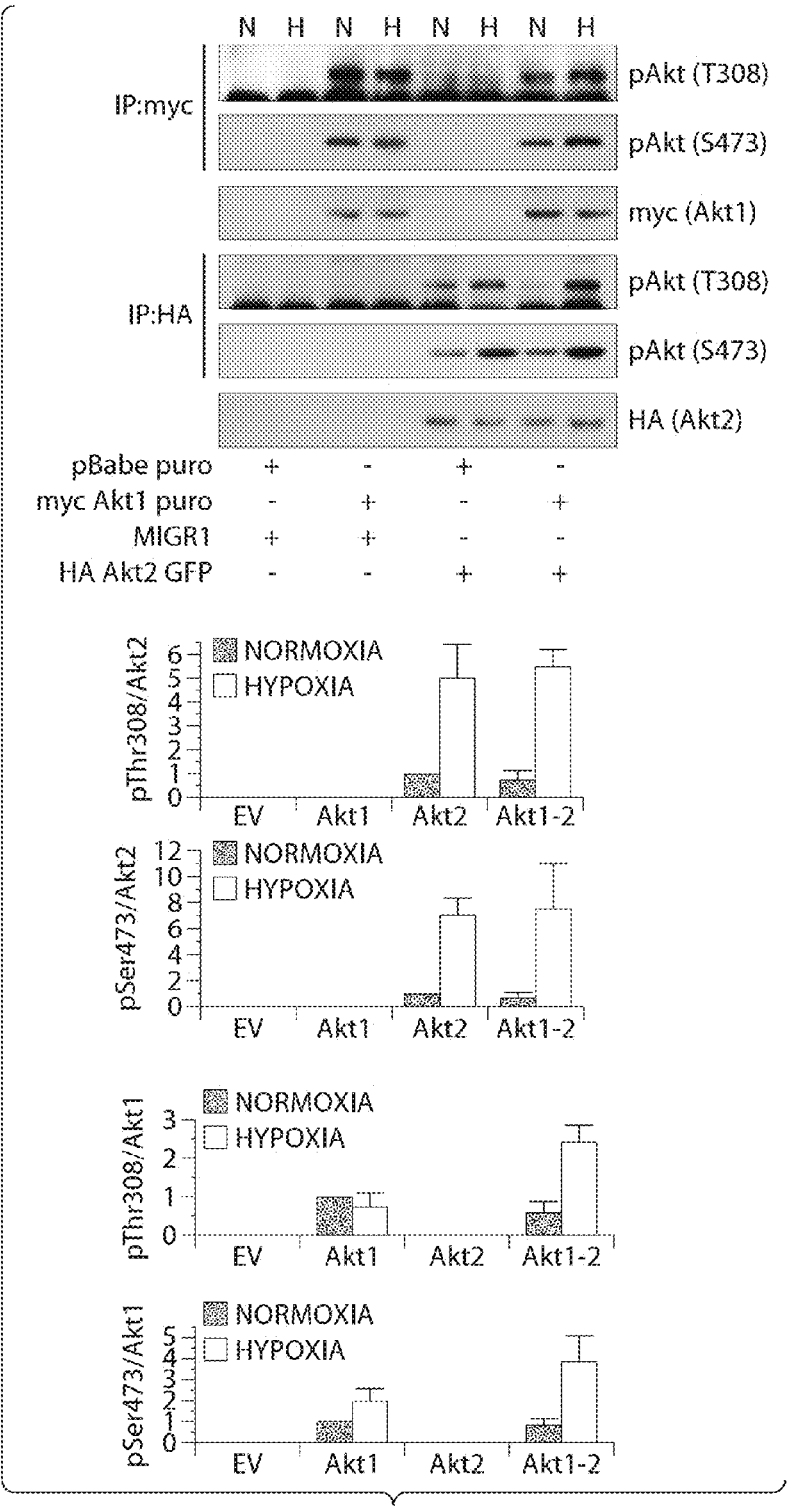

The results (FIG. 28A) showed that PTEN is selectively downregulated upon oxygen deprivation in Akt2-expressing cells and that the downregulation of PTEN correlates with the activation of Akt2, as expected. This method was performed also using Akt2$^{+/-}$ and Akt2$^{-/-}$ MEFs. The results showed that the activity of Akt as determined by probing western blots with phosphor-Akt and Akt phosphosubstrate antibodies, was significantly lower in the hypoxia-treated Akt2$^{-/-}$ MEFs (FIG. 28B left). This was confirmed by probing western blots of the same cell lysates with phosphor-antibodies specific for the Akt substrates Gsk3 and mTOR, as well as against the mTOR substrate 4EBP1 (FIG. 28B right). Transfection of Akt1 and Akt2-expressing cells with anti-miR-21, before exposure to hypoxia, confirmed that the effects of Akt2 on PTEN expression are mediated by miR-21 (FIG. 28C).

By removing the D3 phosphate from D3 phosphoregulated phosphoinositides, PTEN inhibits the activation of Akt2, Akt1 and Akt3. Whether Akt2 regulates the levels of PTEN, and therefore functions as a master regulator of Akt isoforms in oxygen-deprived cells was tested. This model was tested and confirmed by exposing to hypoxia immortalized triple Akt knockout fibroblasts, reconstituted with the combination of myc-Akt1 and HA-Akt2. This treatment led to the induction of miR-21, the downregulation of PTEN and the phosphorylation of both Akt1 and Akt2, and confirmed the model that Akt2 is indeed the master regulator of the Aid isoforms in cells exposed to hypoxia.

Example 23

Akt2 Selectively Inhibits Upon Exposure to Hypoxia Expression of PDCD4 and Sprouty and Activation of ERK Through miR-21

In addition to PTEN, miR-21 also targets the proapoptotic protein PDCD4 and the adaptor protein Sprouty (Spry1), which is known to negatively regulate activation of ERK.

Figure 29A:
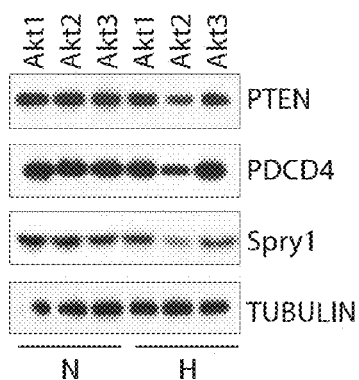
FIGS. 29A-29D are a set of photographs of immunoblots showing Akt2 by miR-21 regulates PDCD4 and Sprouty1 levels under hypoxia.
Figure 29B:
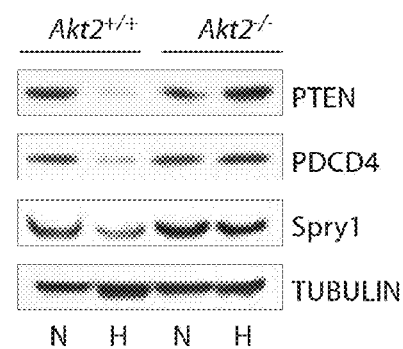
Figure 29C:
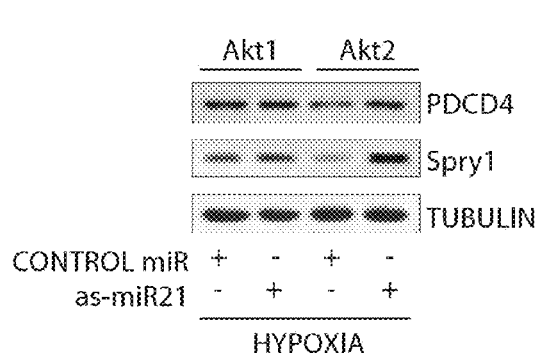
Figure 29D:
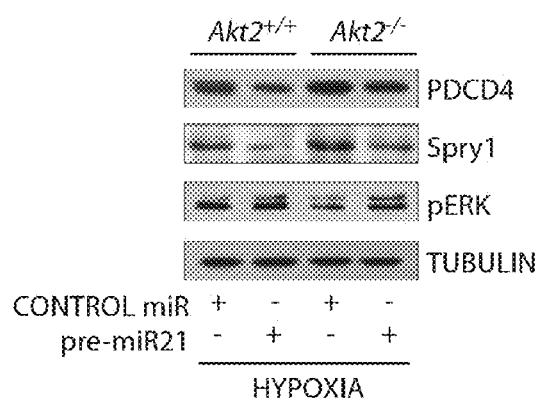

To determine whether Akt2 selectively inhibits the expression of these miR-21 targets upon exposure to hypoxia, we oxygen-deprived Akt1, Akt2 and Akt3-expressing lung fibroblasts and wild type and Akt2$^{-/-}$ primary MEFs. Probing western blots of cell lysates harvested before and after exposure to hypoxia with anti-PDCD4, anti-Spry1 and anti-PTEN (control) antibodies, showed that Akt2 selectively inhibits expression of PTEN, PDCD4 and Spry1, in oxygen-deprived cells (FIG. 29A). Transfection of Akt1 and Akt2 expressing cells with anti-miR21 and wild type and Akt2-1-cells, (FIG. 29B).

These data confirmed that the Akt2-mediated downregulation of PTEN, PDCD4 and Spry1 upon exposure to hypoxia is mediated by miR-21.

Example 24

Combined Downregulation of PTEN, PDCD4 and Sprouty in Oxygen-Deprived Akt2-Expressing Cells is Sufficient to Induce Resistance to Hypoxia The data in Examples herein raised the question whether the downregulation of PTEN, PDCD4 and Spry1 by miR-21 in Akt2-expressing cells exposed to hypoxia is sufficient to induce the resistance of these cells to hypoxia.

Figure 30A:
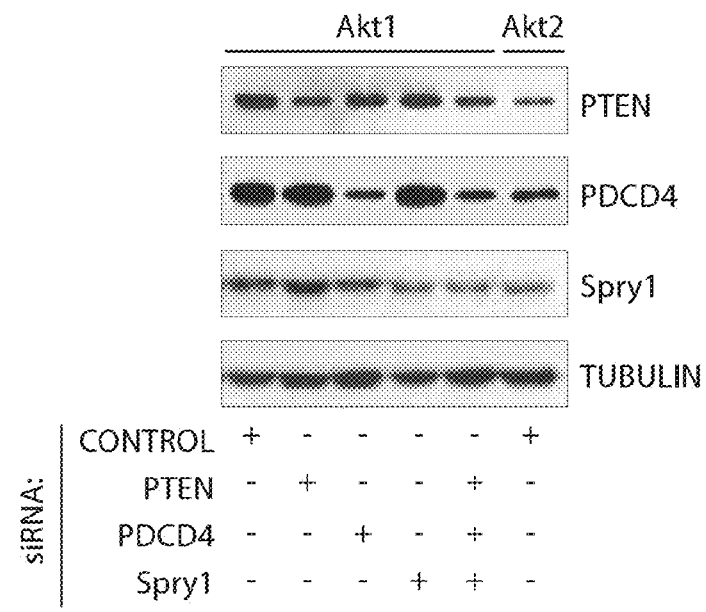
Figure 30B:
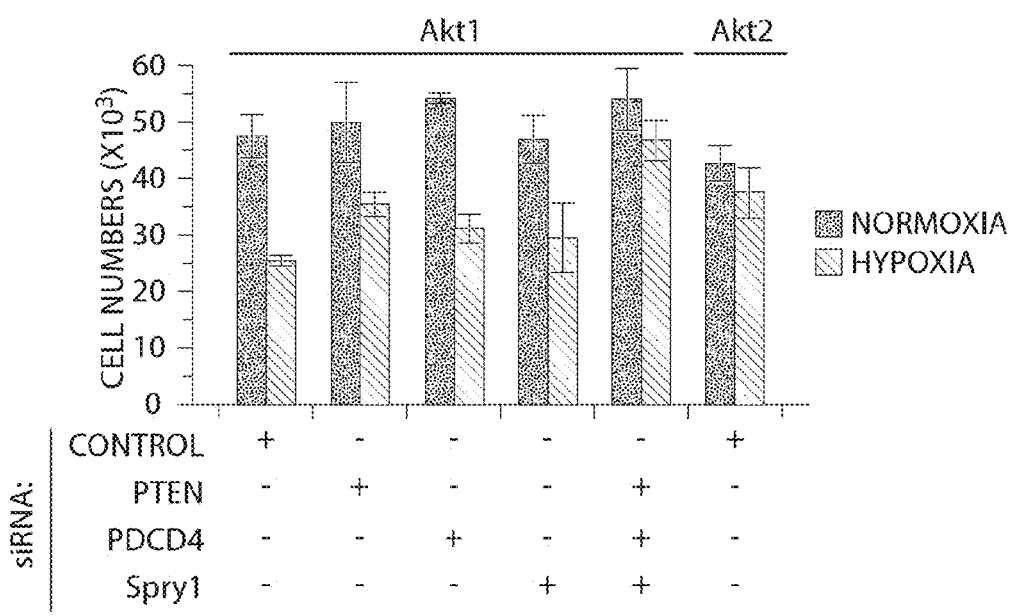
FIG. 30B is a bar graph showing numbers of Akt1- and Akt2-expressing cells surviving under hypoxia. Akt1-expressing cells transfected with Control, PTEN, PDCD4 and Spry1 siRNAs alone or in combination and Akt2-expressing cells transfected with Control siRNA were cultured under hypoxic conditions. Cell number was quantified after 48 hours of growth under normoxic and hypoxic conditions. Data are expressed as mean±SD.

This question was addressed by the method of transfecting Akt1-expressing cells with siRNAs for PTEN, PDCD4 and Spry1 singly or in combination and by comparing the resistance of the transfected cells with the resistance of control siRNA-transfected Akt2 expressing cells. Prior to performing this example, the ability of sets of PTEN, PDCD4 and Spry1 siRNAs was titrated to downregulate the expression of these proteins. The siRNAs selected for the method induced only partial downregulation of these proteins, similar to that observed upon exposure of Akt2-expressing cells to hypoxia (FIGS. 30A and 30B).

The results confirmed that the combined downregulation of the three proteins rendered Akt1-expressing cells similar to Akt2 expressing cells with respect to resistance to hypoxia.

These data show that resistance of Akt2-expressing cells to hypoxia is mediated by downregulation of PTEN, PDCD4 and Spry1 mediated by miR-21.

Example 25

Induction of miR-21 in Akt2-Expressing Cells Upon Exposure to Hypoxia is Due to Selective Activation and Binding of CREB/CBP and NF-κB to the miR-21 Enhancer and Selective Regional Histone H3 Acetylation at K9

Figures 31A, 31B:
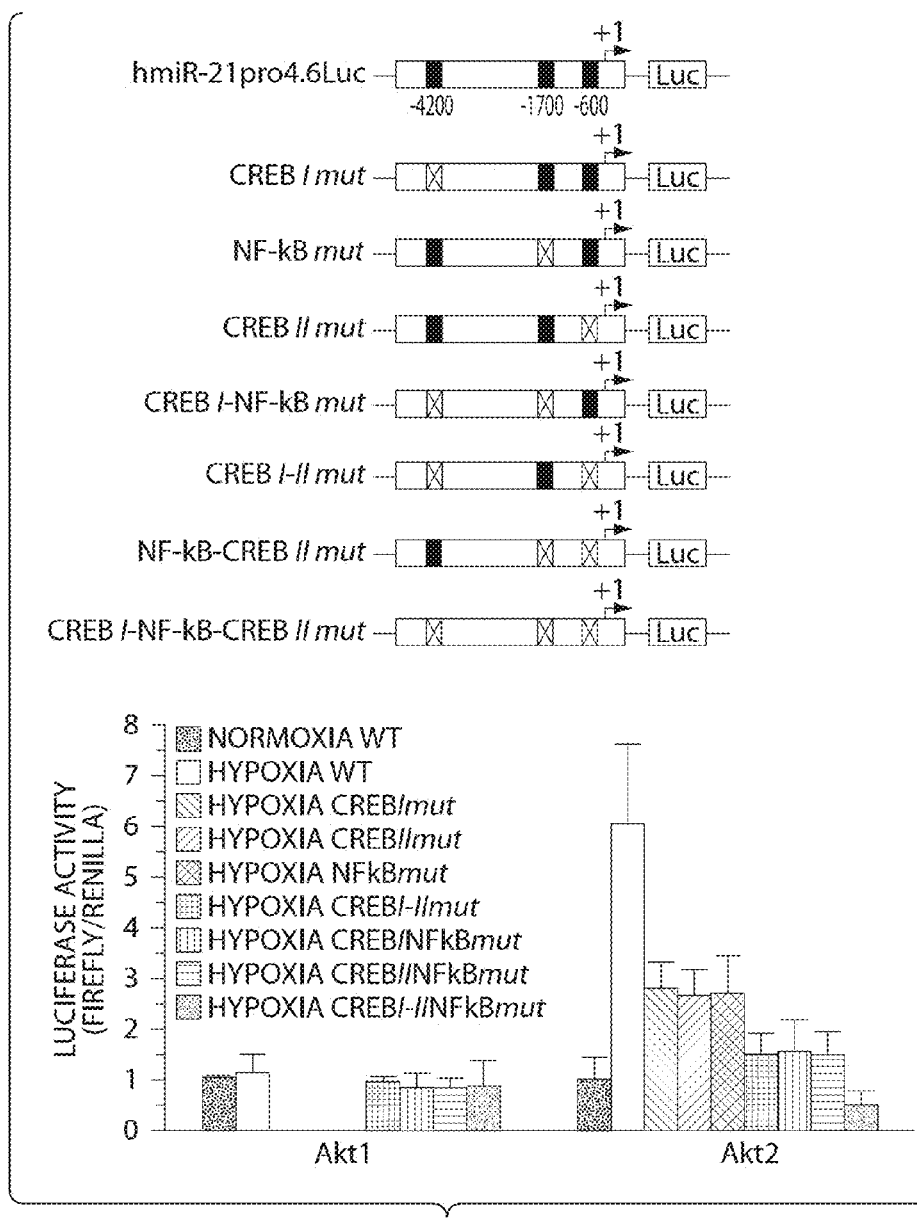
FIGS. 31A-31B are a set of schematic diagrams, bar graphs and a photograph of immunoblots showing that Akt2 induces the selective activation and binding of CREB/CBP and NF-κB to the miR-21 promoter and localized histone H3 acetylation at K9
Figure 31C:
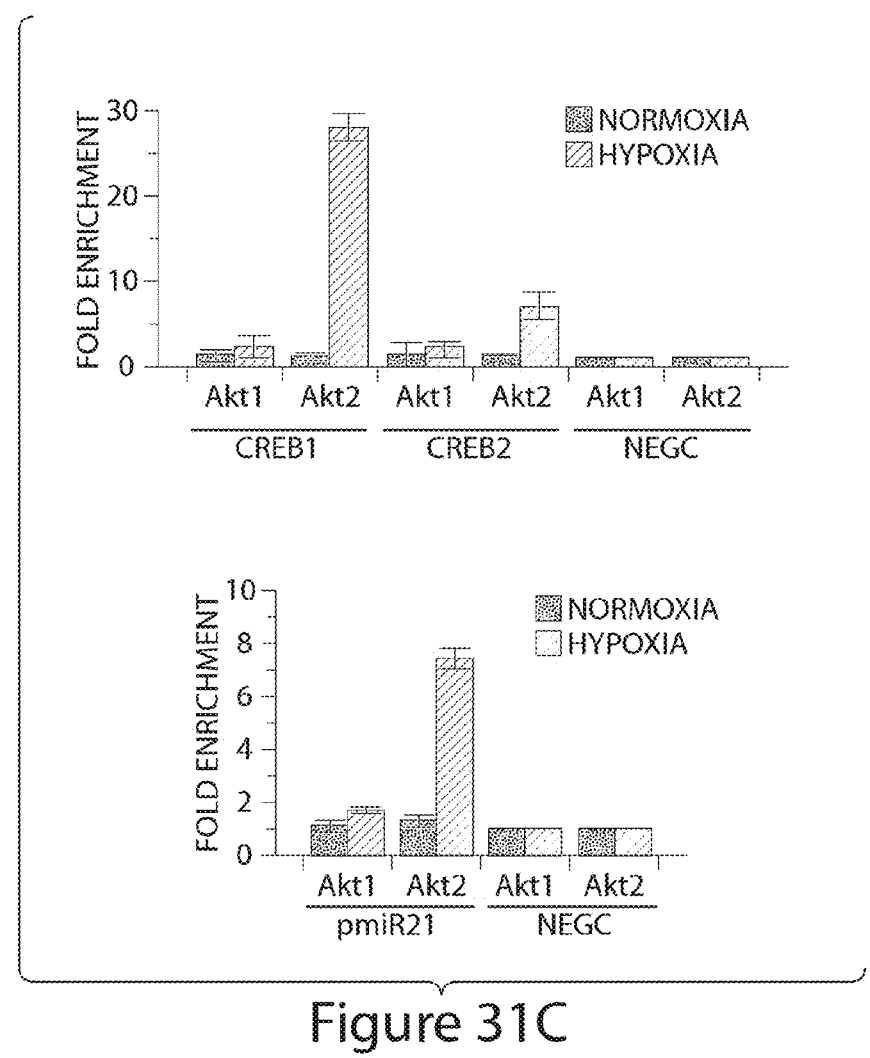
FIG. 31C is a set of bar graphs showing chromatin immunoprecipitation for CREB and NF-κB in Akt1-, and Akt2-expressing cells growing under normoxic or hypoxic conditions. Left panel shows binding of CREB and right panel shows binding of NF-κb to their respective binding sites, before and after exposure to hypoxia as studied by real time PCR. Data are expressed as mean±SD.
Figure 31D:
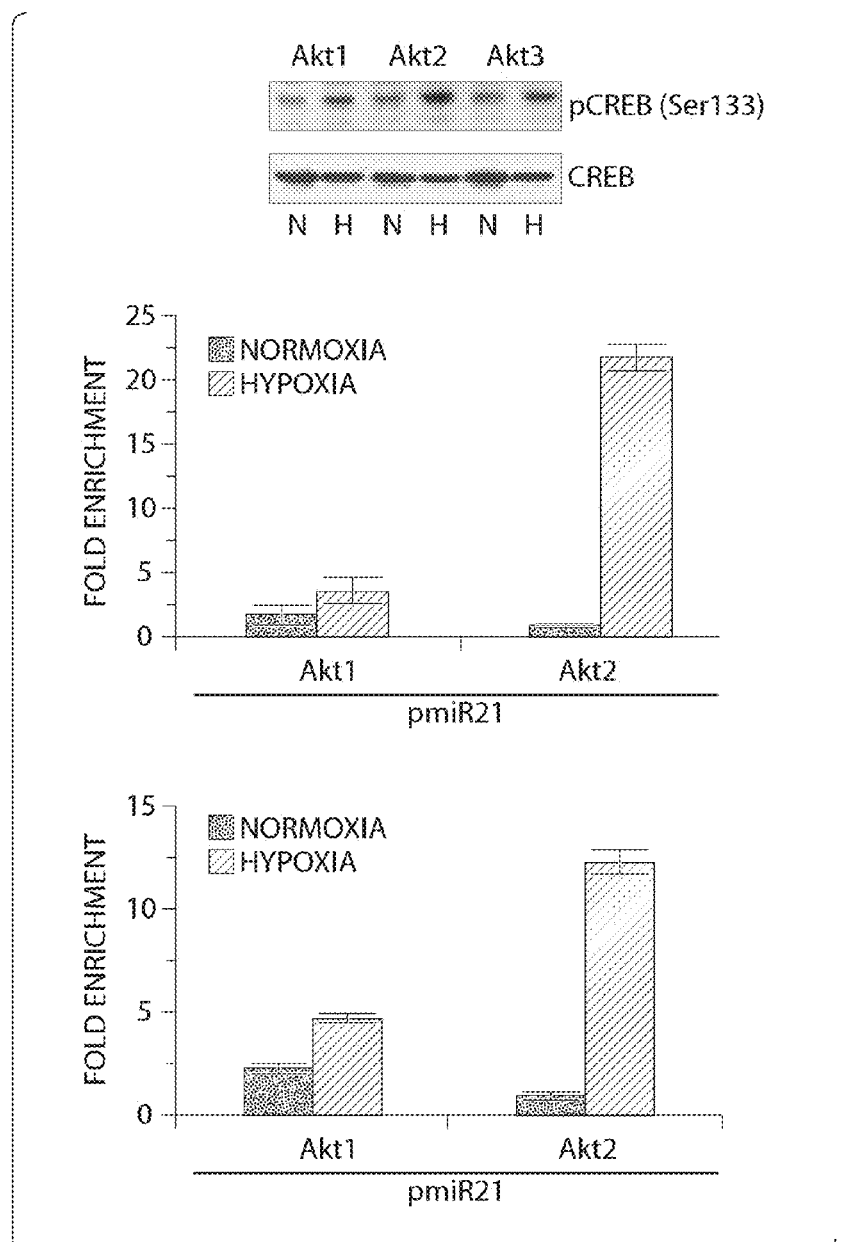
FIG. 31D is a photograph of immunoblots showing CREB phosphorylation in Akt1-, Akt2-, or Akt3-expressing cells upon oxygen deprivation. Cell lysates were blotted with antibody specific to phospho-CREB (Ser133), and antibody specific to CREB was used as a loading control.

Analysis of a 5 kb DNA sequence upstream of the miR-21 transcriptional start site identified two CREB binding sites and one NF-κB binding site (FIG. 31A). To determine the functional significance of these sites, a reporter construct was generated by placing the luciferase gene at the 3' end of this sequence, downstream of the miR-21 transcriptional start site. This construct was then used to generate mutant constructs in which the CREB binding sites and the NF-κB binding site were inactivated by point mutation singly and in combinations.

Transfection of these constructs in Akt1 and Akt2-expressing cells, followed by oxygen deprivation of the transfected cells showed that hypoxia induces expression of the luciferase gene only in Akt2-expressing cells transfected with the wild type construct. Mutant constructs were defective in induction of the luciferase gene indicating that both CREB and NF-κB binding are required for the full activation of the promoter by hypoxia. However data for mutations in both the CREB and NF-κB binding sites simultaneously showed a more robust inhibitory effect on promoter activation (FIG. 31A.)

The Examples herein showed that Akt1 and Akt2 regulate differentially the activation and DNA binding of CREB and NF-κB. Chromatin immunoprecipitation (IP) was employed herein to compare the binding of CREB and NF-κB to their respective binding sites in Akt1 and Akt2-expressing cells, before and after exposure to hypoxia. The results (FIG. 31B) showed that the binding of CREB to both CREB binding sites and the binding of NF-κB to the NF-κB binding site were Akt2-dependent.

CREB undergoes phosphorylation at Ser133 by PKA, PKC and perhaps Akt. Probing cell lysates of Akt1, Akt2 and Akt3-expressing cells, harvested before and after exposure to hypoxia, with a phosphor-CREB (Ser133) antibody, showed that hypoxia promotes phosphorylation of CREB at this site most efficiently in Akt2-expressing cells. The increased CREB binding to DNA in oxygen-deprived Akt2-expressing cells was considered as unlikely to be mediated by phosphorylation at Ser133, because phosphorylation at this site is known to only regulate CREB binding to CBP.

Chromatin IP, using a CBP-specific antibody, showed that hypoxia induces CBP association with the CREB binding site in an Akt2-dependent manner and was consistent with the finding that CREB phosphorylation at Ser133 was more pronounced in Akt2-expressing cells. Because CBP is a histone H3K9 acetyltransferase, the regional H3K9 acetylation was examined in the vicinity of the first CREB binding site, also by chromatin IP. The results showed the differential H3K9 acetylation in Akt2 expressing cells (FIG. 31E).

Example 26

HIF1a-Positive Mammary Adenocarcinomas Arising in MMTV-PyMT/Akt2$^{-/-}$ Mice Express Lower Levels of miR-21 and Higher Levels of the miR-21 Targets than in MMTV-PyMT/Akt Wild Type and MMTV-PyMT/Akt1$^{-/-}$ subjects To determine whether the Akt2-miR21 axis is operating during oncogenesis in hypoxic tumors, expression of miR-21 and its targets was examined in mammary adenocarcinomas in HIF1a-expressing MMTV-PyMT/Akt$^{+/+}$, MMTV-PyMT/Akt1$^{-/-}$ and MMTV-Pymt/Akt2$^{-/-}$ subjects. H1F1a expression was examined as a measure of hypoxia.

Figure 32A:
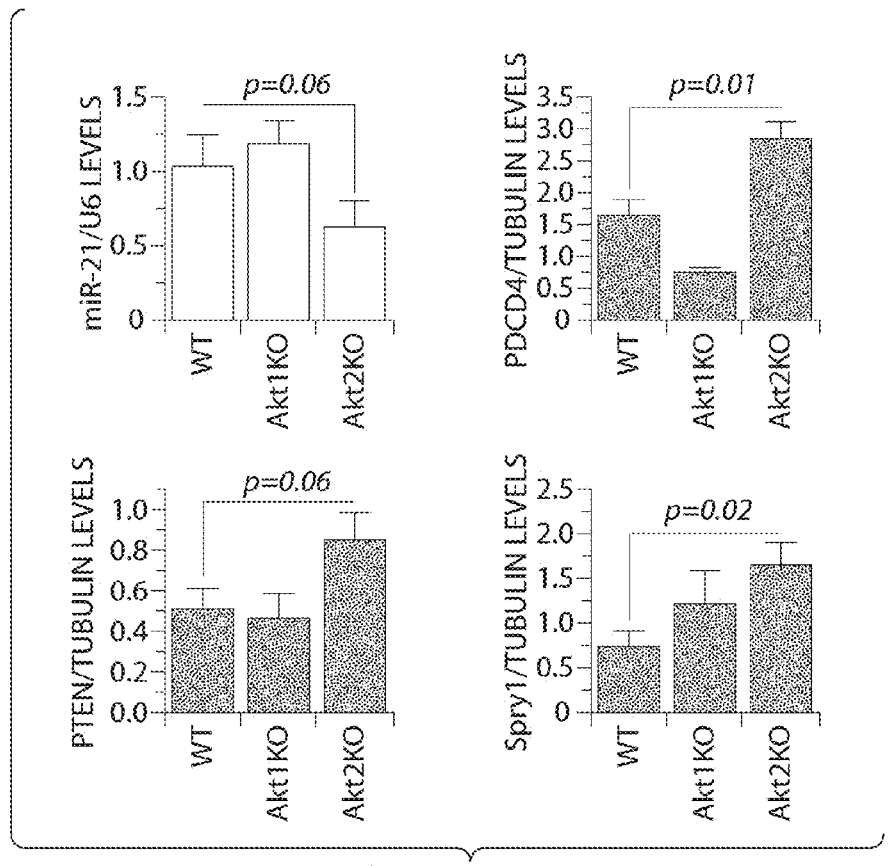
FIGS. 32A-32C are a set of bar graphs, photomicrographs and distribution plots showing that the Akt2-miR21 axis operates during oncogenesis in hypoxic tumors.

The results showed that the tumors expressed robust levels of H1F1a and that H1F1a-positive tumors arising in Akt2$^{-/-}$ mice express lower levels of miR-21 than tumors arising in wild type and Akt1$^{-/-}$ mice. Western blotting and immunohistochemistry data also showed that the expression of the miR-21 targets PTEN PDCD4 and Spry1 was higher in tumors arising in Akt2$^{-/-}$ than in tumors arising in wild type and Akt1$^{-/-}$ mice (FIG. 32A).

Example 27

Expression of miR-21 Exhibits a Positive Correlation and Expression of PTEN Exhibits a Negative Correlation with Expression of Akt2 in HIF1a-Positive Ovarian Carcinomas Thirty one human ovarian carcinomas were classified into groups expressing high or low H1F1a. Since H1F1a is induced in cells exposed to hypoxia, high H1F1a expression was proposed to be identifying hypoxic tumors. These tumors were subdivided into high Akt2 and low Akt2-expressing groups.

Figure 32B:
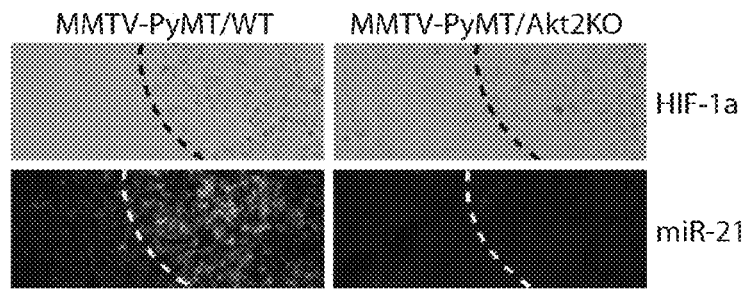
Figure 32C:
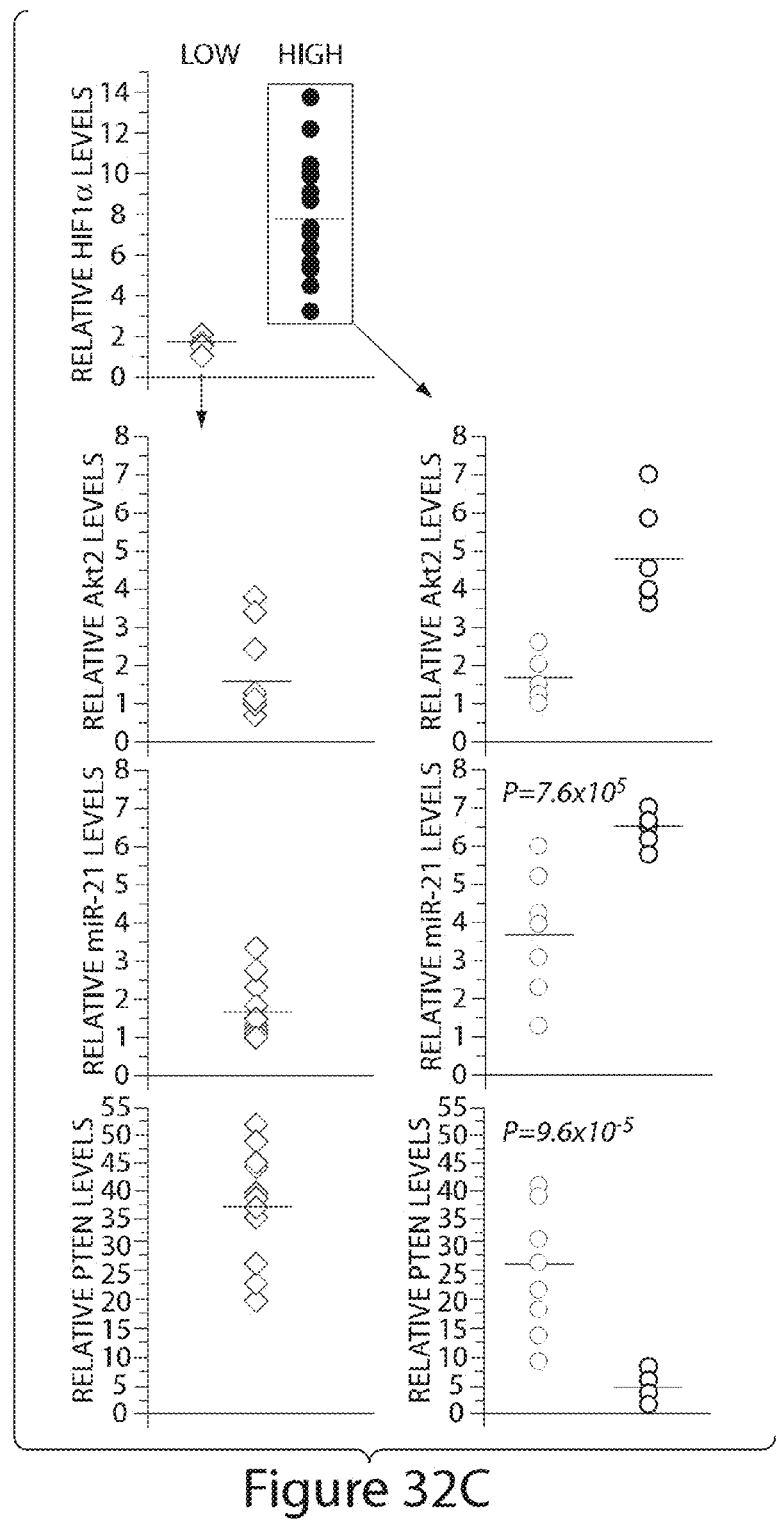

Analysis of expression of miR-21 and PTEN tumors in the two groups revealed a positive correlation between Akt2 and miR-21 expression and a negative correlation between Akt2 and PTEN expression (FIG. 32B). These data indicate that Akt2 functions as the critical regulator of the miR-21-mediated resistance of human ovarian carcinoma cells to hypoxia in vivo.

Figure 33:
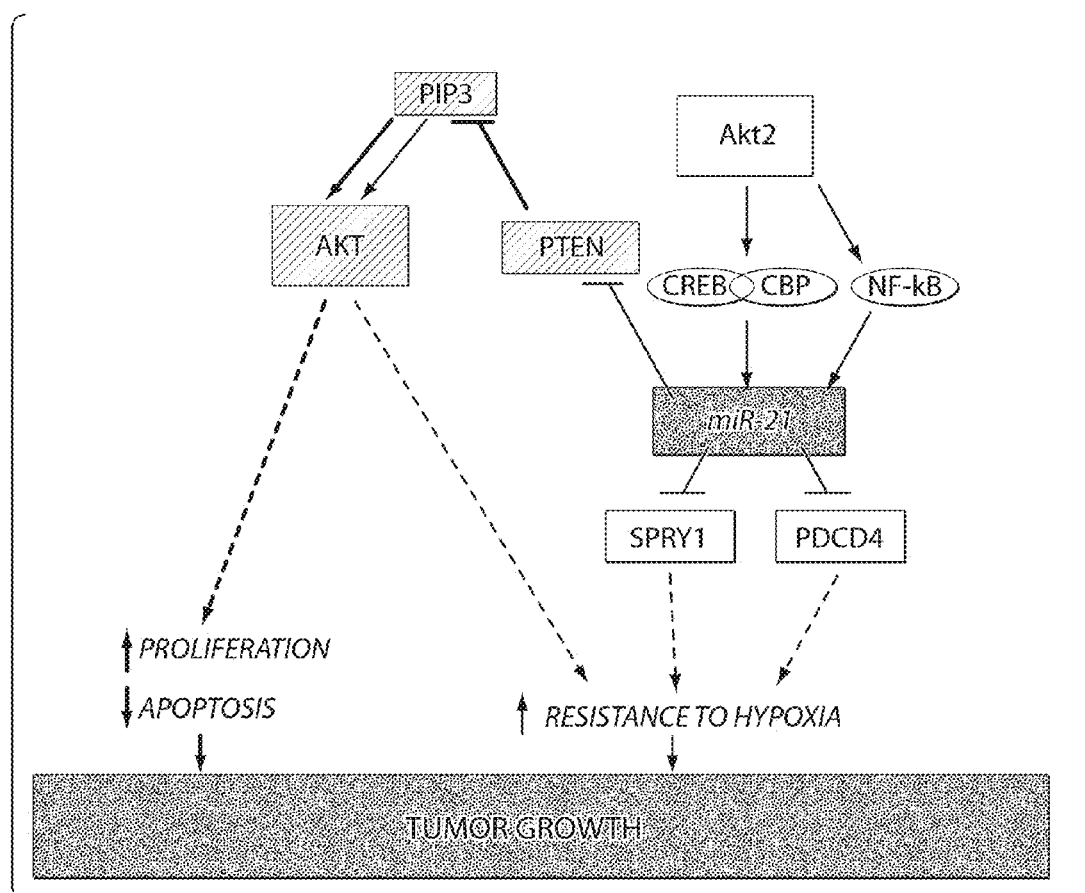
FIG. 33 is a schematic representation of the proposed model. In addition to the Akt signaling pathway (blue) that controls tumor growth under normoxic conditions, upon oxygen deprivation the activation of Akt2-miR21 axis (red) confers resistance to hypoxia.

Low expression of HIF1a in ovarian carcinomas was proposed to be a method of identifying normoxic tumors. Accordingly, analyzing levels of miR-21, PTEN and Akt2 expression in these tumors showed a universally low expression of Akt2, low expression of miR-21 and high expression of PTEN (FIG. 33). The correlation of low Akt2 expression with low HIF1a further shows that Akt2 regulates the expression of H1F1a. Alternatively, hypoxia promotes the selection of cells expressing high levels of Akt2 while normoxia does not. Because H1F1a does not appear to be differentially regulated by Akt1 and Akt2, the low Akt2 levels in tumors expressing low levels of H1F1a indicated that hypoxia promotes the selective survival of Akt2-expressing tumor cells.

Example 28

Figure 34:
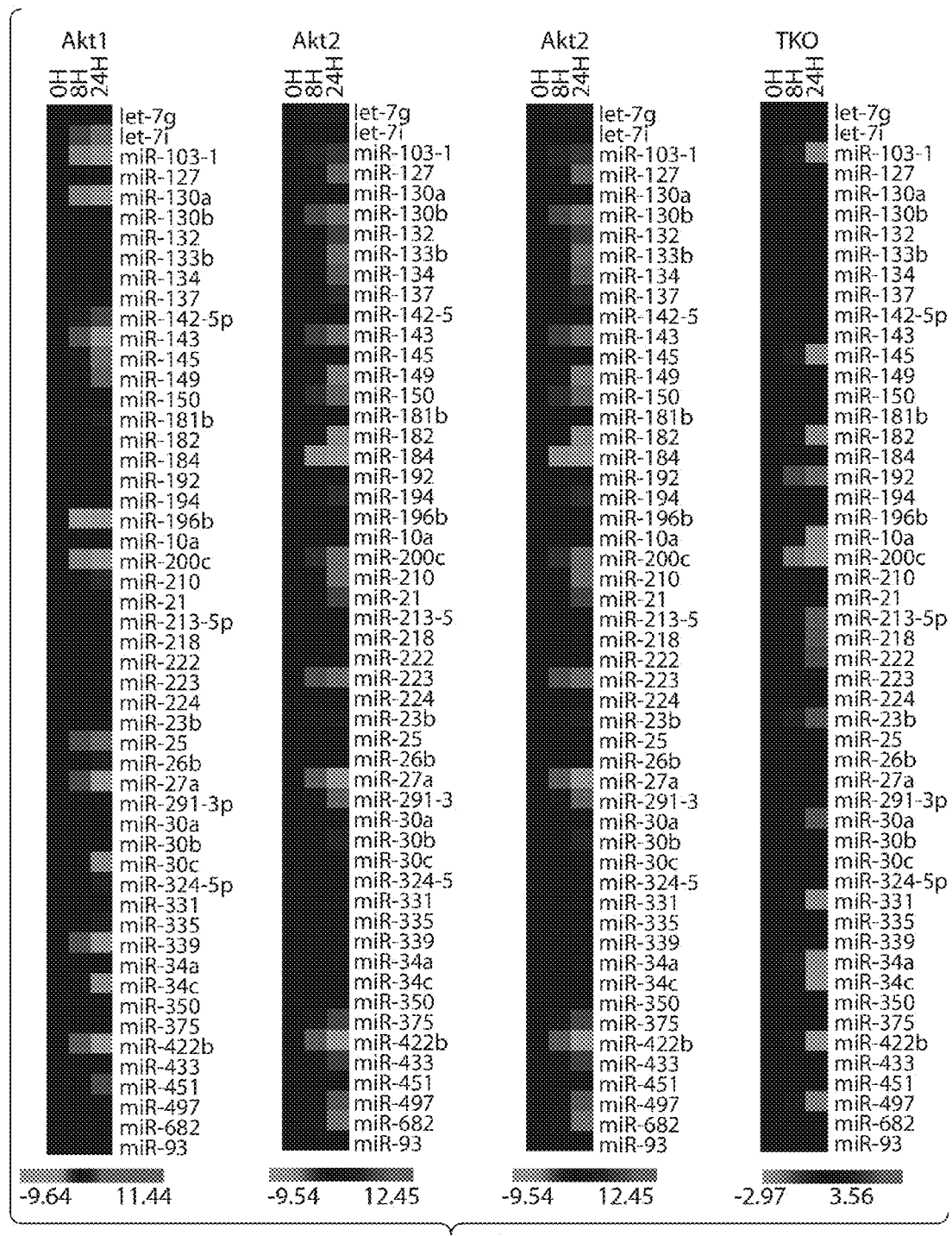
FIG. 34 is a heat map showing miRNA species produced under hypoxia conditions.

Identifying Conventional Genes and Noncoding RNAs that are Differentially Regulated by Akt Isoforms and Determining the Molecular Mechanisms Behind the Differential Regulation of these Genes Examples herein show that there are dramatic differences in microRNA gene expression in cells expressing different Akt isoforms. For instance, cells expressing different Akt isoforms have different microRNA gene signatures when exposed to hypoxia (FIG. 34) Based on these data, major informative differences in gene expression and in regulation of gene expression in response to signals transduced by the three Akts are described herein.

Global gene expression analyses with each of the lung fibroblast and the MCF10A cell systems are done using cDNA hybridization to high-density gene arrays (Lennon et al., 1991 Trends Genet. 7: 314-317). Since these arrays are limited to conventional genes, arrays of non-coding RNAs, including small RNAs, such as microRNAs, and long conserved RNAs are probed. The microRNA data complement and extend data in Examples herein. The microarrays are limited by the fact that they provide only a partial picture of the transcribed genome. This problem was partially solved with the introduction of deep sequencing, a method that provides a complete and unbiased view of the entire transcriptome. This method is also limited however, because of its low dynamic range. Exploratory deep sequencing examples, comparing the results with the results of the microarray examples described in Examples herein are performed. These examples, like the microarray examples, compare the transcriptome of Akt null cells and cells expessing Akts or individual Akt isoforms.

In these examples, poly(A) RNA is extracted from cells and used to generate double stranded cDNA using random hexamers as primers. The double stranded DNA is sheared by sonication. The sheared DNA is then used to prepare sequence libraries according to the Illumina protocol (http://www.illumina.com/downloads/SS_DNAsequencing.pdf). Illumina deep sequencing is used to generate 27-base pair reads from replicate samples for each cell line. The reads are mapped to the human genome (hg18), using Eland software (16). Digital expression levels are normalized by calculating the theoretical number of unique 27-mers. Identifying coding and non-coding sequences that are regulated by Akt and coding and non-coding sequences that are differentially regulated by Akt isoforms is performed. Examples herein show significant differences in microRNA regulation between Akt isoforms and confidently predict the differential regulation of additional genes. Differences in gene expression and differences in signaling between Akt isoforms are integrated at the level of gene expression.

A key goal of functional genomics is to identify transcriptional regulatory elements of physiological significance throughout the genome. To carry out an unbiased genome wide mapping of relevant transcription factor binding sites and histone modifications in cells (Akt-null cells and cells expressing three Akt isoforms or individual Akt isoforms), grown under different culture conditions, a combination of chromatin immunoprecipitation (ChIP) and DNA sequencing is used. This combination is a powerful tool that has often showed unexpected and crucial insights regarding the biology of transcriptional regulators (Euskirchen et al., 2007 Genome Res. 17: 898-909). Prior to using genome-wide approaches for mapping the binding of Akt-regulated transcription factors and Akt-regulated histone modifications, identifying transcription factors and chromatin modifications that are regulated similarly or differentially by the three Akt isoforms are to be carried out on a set of 100 genes that are regulated similarly or differentially by the three Akt isoforms.

The existing data of the NIH "Epigenome" Roadmap project are used to identify transcription factors and chromatin modifications that are characteristically associated with the domains of these genes. For a better prediction of relevant transcription factors and histone modifications, the "Epigenome" Roadmap data are correlated with the Akt status of the cell lines from which the data were derived.

Based on this information, targeted ChIP-ChIP examples are carried out probing tiling arrays of the selected genes. This example identifies the relevant transcription factors and histone modifications that are further targets in the genome-wide ChIP-sequencing examples. The binding of selected transcription factors and the mapping of selected histone modifications genome-wide are carried out using ChIP-sequencing, using the novel technology of Helicos single molecule Chip-sequencing, which is an amplification-free assay with millions of reads per sample. The advantage of this technology relative to other platforms is that it allows the analysis of ChIP-Seq material directly, without amplification. ChIP assays typically provide low nanogram quantities of DNA, which are too low for ligation- and solid-phase PCR-based methods. Using this protocol ChIP-seq examples may be performed even from ChIP samples derived from small populations of cells.

According to the Helicos protocol, immunoprecipitate genomic DNA from a ChIP procedure is obtained using specific antibodies for transcription factors or specific histone modifications. The DNA is modified with a poly-A tail and is loaded onto the instrument. No ligation or PCR amplification steps are required. The tailed fragments hybridize to complementary poly-T strands anchored to the flow cell surface. Inside the HeliScope Single Molecule Sequencer, a series of nucleotide addition and detection cycles determine the sequence of each fragment, each then stored as a "read. Open source data analysis software aligns the hundreds of millions of reads to a reference sequence.

DNA methylation is another process that plays a critical role in the epigenetic regulation of gene expression and is functionally linked to histone modifications. The role of Akt and its three isoforms in DNA methylation in cells grown under different culture conditions is investigated here in further examples. Genome wide analysis of DNA methylation is carried out using Agilent CpG island arrays (Kron et al., 2009 PLoS ONE 4:e4830). Validation of the array data is performed by MethyLight PCR analysis.

Gene expression is examined by analyzing the abundance of RNAs representing both protein-coding and non-coding genes. Non-coding RNAs, such as microRNAs, regulate gene expression primarily at the post-transcriptional level. Observing dramatic differences in microRNA gene expression between cells expressing different Akt isoforms shows significant changes from the transcriptomes to proteomes of these cells. The role of Akt isoforms in gene expression also addresses gene expression at the protein level with quantitative proteomics. Several methods of quantitative proteomics were developed over the last decade (Ong et al., 2005 Nat. Chem. Biol. 1: 252-262). These methods are based on the principle of labeling peptides of protease-digested cell lysates derived from two or more samples, with stable isotopes. These isotopes introduce predictable mass differences, which are detected by mass spectrometry, between peptides derived from different samples. Differences in the levels of differentially-labeled peptides provide an accurate measure of the relative levels of the peptides (and the proteins from which they were derived) among samples, and are determined, using iTRAQ (isobaric tag for relative and absolute quantitation), a method that allows the simultaneous comparison of multiple samples.

Example 29

Identifying Proteome Wide Posttranslational Modifications in Akt-Null Cells and Cell Expressing Different Akt Isoforms The level of expression of different proteins across the entire proteome and protein modifications is examined including phosphorylation, methylation, acetylation and ubiquitination.

Examples herein describe the phosphoproteome of Akt-null lung fibroblasts and lung fibroblasts expressing the set of Akt isoforms, or expressing one isoform at a time. The first round of examples, which has been completed, identified more than 300 proteins that are phosphorylated on Akt-targeted motifs in an Akt-specific manner. Only a fraction of these proteins are known Akt targets. The majority are novel. Although the phosphoproteomes of cells expressing different Akt isoforms overlap, they also exhibit significant differences.

Examples herein show methods carried out in both the lung fibroblast cell system, and in MCF10A cells in which individual Akt isoforms or combinations of isoforms are knocked down inducibly. Studies using these cells focus on the phosphoproteome of Akt-null cells and cells expressing three Akt isoforma, or one Akt isoform at a time, and growing under normal conditions or in hypoxia. Cells are plated in equal numbers in complete media and they are harvested for phosphoproteomic analysis during the logarithmic phase of growth (day 2) and after they reach confluency (day 4); the cells described above are placed in an atmosphere of 0.1% $O_2$ in a hypoxia incubator and they are harvested 8, 16, and 24 hours later. At least one additional time point is added depending on the results of the examples addressing the role of Akt isoforms in the growth and survival of cells cultured under hypoxia. Control cells are harvested prior to placing the cells in the hypoxia incubator (time 0). The cells are grown in complete, serum-containing media. Cell lysates are transferred to Cell Signaling Technologies for phosphoproteomic analysis. The approach used by the Proteomics facility of Cell Signaling Technologies (CST) to map the phosphoproteome involves preparation of cell lysates, digestion with proteases to generate peptides, immunoprecipitation with phospho-specific motif antibodies (examples herein utilizing two phospho Akt substrate antibodies recognizing the motif RXRXXpS/pT (CST catalog numbers #9614 and 23C8D2) and analysis by LC-MS/MS mass spectrometry. Two types of mass spectrometry instruments are used for this analysis, LTQ-ETD, which solves the neutral loss problem of basophilic peptides, and the accurate mass LTQ-OrbiTrap instrument, which is used for label-free-quantitation. With these types of mass spectrometers, the number of observed spectra assigned to a particular protein serves as a semiquantitative measure of phosphopeptide abundance. With the OrbiTrap analysis, more accurate label-free-quantitation is obtained using the MZmine program To gain deeper understanding of the role of Akt in the regulation of posttranslational modifications (PTMs), the same samples used in the phosphoproteome study are surveyed for other PTMs, by probing western blots of these lysates with antibodies directed to specific motifs. Such antibodies include acetyl-lysine, Ubiquitin brach, and Arginine and Lysine methylation antibodies. Once confirmed by western blotting that Akt isoforms regulate the global levels of protein acetylation, methylation or ubiquitination, LTQ-OrbiTrap mass spectrometry is carried out to map the sites of these modifications at the level of the entire proteome. Label-free-quantification of the data is obtained using the MZmine software.

Example 30

Integrating the Data on the Biology of Cells Expressing Different Akt Isoforms with Isoform-Specific Gene Expression and Protein Modification Data, Using Computational Techniques, and to Applying Them to Human Cancer Examples herein generate the following sets of data: post-translational modifications (phosphorylation, acetylation, methylation and ubiquitination) of proteins that are modified directly or indirectly by growth factor or hypoxia-transduced Akt signals. Among these Akt targets are transcription factors and enzymes that modify histones and DNA, and other types of proteins; sets of protein coding and non-coding genes (microRNAs or long conserved RNAs) that are regulated by Akt in response to growth factor and hypoxia signals; and proteins involved in transcription factor binding, histone modifications and DNA methylation of genes regulated by Akt in response to growth factor signals and hypoxia. These sets of data show the processes that are regulated similarly or differently by each of the Akt isoforms. These data are the most extensive biological datasets in Akt signaling, and yields insights into the complexities of signaling pathways. The results obtained from these sets of data are computationally integrated in order to define the targets of each Akt isoform, and gain a mechanistic understanding of their signaling networks, and how these relate to function.

To uncover these complex relationships, targets of Akt proteins that are known to induce gene expression changes are identified and characterized. A superset of proteins modified by three Akt isoforms, or individual isoforms, and use protein domains associated with DNA-binding activity to recognize transcription factors (TFs) are identified. TF lists and also TF domain lists constructed by TransFac, SwissProt, ENSEMBL, UCSC, and the larger general genomics data above are then assembled. Lists of chromatin modifying proteins from the literature, databases, and the epigenomics community are further assembled. These are target level-1 regulators, which include both transcription factors and epigenetic regulators. The set of direct targets of Akt is referred to as "T1", and the subset of these that is referred to as regulators as "R1".

R1 regulators are used to describe gene expression changes that are attributed to direct targets of these regulators, based on gene expression and epigenetic modification datasets.

Genome-wide ChIP-seq binding data for R1 transcription factors further define direct targets of R1, and evaluate how these are affected in expression change examples. If data is not available, known motifs of R1 transcription factors are used to define targets based on conserved occurrences of these regulatory motifs in promoter regions of R1 transcription factors. To capture direct targets of R1 if neither ChIP examples nor regulatory motifs are known, search for common regulatory motifs in the upstream regions of genes with altered expression patterns is performed, and additional targets are defined based on genes that contain a common motif, even if the corresponding regulator is not known. The set of direct targets of R1 regulators is referred to as "T2", and the subset amongst them that are regulators as "R2". Special attention is paid to microRNA genes that are direct targets of R1, and thus part of R2.

Effects of R2 microRNAs on protein expression patterns are investigated. Targets of R2 microRNAs are predicted based on previously published information, by using conserved instances of 7-mer motifs associated with seed regions of R2 microRNAs. Search for systematic differences between the mRNA expression levels and the protein expression levels of targets of R2 microRNAs is performed to study effect of these microRNA genes in post-transcriptional regulation at the global level. The list of proteins is intersected with the list of direct targets of Akt (T1), to search for potential feedback loops, in which indirectly induced microRNAs is repressing direct Akt targets. The list of R2 microRNA targets is further intersected with the list of direct targets of R1 regulators, to search for smaller feedback loops in which an induced microRNA is repressing its inducer.

The observed difference between the proteins that are direct targets of Akt proteins (contain an Akt phosphorylation recognition site) are examined as well as those that are affected indirectly (phosphorylated proteins that lack an Akt target site, or proteins that have undergone other modifications). To account for these differences, a search for the set of T2 targets for proteins that are themselves signal transducers which are newly activated by Akt targets is conducted as well as search for signal transducers in the set of R2 microRNA targets, for signal transducers whose translation levels is affected by Akt indirect targets.

The list of regulatory relationships is extensive, and each of the mechanisms may affect the expression, translation, or modification of additional regulators, and indirectly their targets. A model of the larger Akt signaling network is constructed, with nodes for each protein in the above lists (with mRNA expression levels, protein levels, and protein modification states), and similarly for every microRNA in these lists (with its expression level). The edges of these networks are defined based on microRNA and transcription factor target relationships as predicted by genome-wide ChIP-seq examples and conserved regulatory motif instances. The edges are either positive or negative, depending on the annotation of transcription factors as activators or repressors, and similarly for the protein modification enzymes, the edges are decorated with the type of modification they confer. The system of differential equations defined by this network is expressed in a simulation system, constrained by the observed levels measured, and solved for the values of edges for which steady-state levels of expression match those derived from earlier procedure. The free parameters in each case are type of inhibition or activation and each edge, or a zero if that edge is not contributing to the network.

The networks and parameters obtained for Akt1, Akt2, and Akt3, as well as for normal cells in each of these cases is further analyzed, and the parameters so obtained are used to infer differences in the direct and indirect targets of each isoform, and to make specific predictions for the regulators involved in each case. In addition to the parameter differences in the simulation results, differences in T1, R1, T2, and R2 among the three isoforms are investigated, and the set of differential direct and indirect targets so characterized. In each case, specific predictions are made of regulatory relationships that are validated.

Example 31

Translational Studies to Address the Effects of Imbalanced Expression of Akt Isoforms in Human Tumors and the Effects of Akt Inhibitors that Preferentially Target Different Akt Isoforms Individual Akt isoforms are selectively upregulated in human tumors. For example, 15% of ovarian cancers express high levels of Akt2 because of gene amplification (Cheng et al., 1992 Proc. Natl. Acad. Sci. U.S.A. 89: 9267-9271). Similarly, human melanomas are known to selectively express high levels of Akt3 (Stahl et al., 2004 Cancer Res. 64: 7002-7010). Since Akt isoforms are non-coordinately upregulated in human tumors, data herein regarding the unique functional properties of different isoforms contribute to understanding of the role of Akt in human cancer. To address the applicability of the data in Examples herein to human cancer, in situ hybridization to and antibody staining of a panel of 450 human ovarian tumors of different cell types are carried out. The tumors used for these examples are selected for expressing high levels of one of the three Akt isoforms. The RNAs and proteins targeted in these examples are selected based on the selective modulation of their expression and/or posttranslational modification by a given Akt isoform. Data from the Examples herein provide information that is critical for understanding of the Akt in human cancer and identify novel biomarkers specific for tumors with high Akt or Akt isoform-specific activities.

Additional embodiments and examples of the invention are found in the claims below, which are illustrative and are not to be construed as further limiting. The contents of all references cited herein and in the Appendices are hereby incorporated by reference herein.

What is claimed is:

1. A method for prognosing or diagnosing a potential cancer and progression of an existing cancer in a patient by analyzing Akt isoform imbalance, wherein the imbalance comprises a decreased ratio of Akt1 protein to Akt2 protein compared to that ratio in a normal subject, the method comprising:

measuring an expression profile of a plurality of microRNA (miRNA) species regulated by Akt isoform expression in a sample from the patient, by real-time PCR, or by using an array of miRNA nucleotide sequences of a plurality of miRNA species each sequence at a known location on a substrate; and comparing the profile from the patient with that of the normal subject not having the cancer and obtaining an miRNA tumor expression profile;

wherein the decreased ratio of the Akt isoform expression profile of the sample from the patient compared to the normal subject is a prognosis or diagnosis of the potential cancer or an indication of the progression of the existing cancer in the patient.

2. The method according to claim 1, wherein the miRNA is miR-200a.

3. The method according to claim 1, wherein the sample comprises a cell from a biopsy of the patient comprising at least one selected from the groupage of: blood, cerebrospinal fluid, mammary glands, prostate gland, lung, bladder, cervix, and colorectal, the method further comprising culturing cells ex vivo and screening compounds in a library contacted with aliquots of resulting cultured cells and control normal subject cells, to obtain a potential inhibitor that restores Akt expression balance to an amount observed for the normal subject and thereby inhibits the cancer.

4. The method according to claim 1, further comprising measuring decreased expression compared to the normal subject of at least one transcription factor miRNA, and prognosing the cancer or the cancer progression from the decreased transcription factor expression of the transcription factor.

5. The method according to claim 4, wherein the transcriptional factor is selected from at least one of: IGF1 and TGFβ.

6. The method according to claim 1, further comprising measuring Akt amounts and observing no difference between amounts in patient and in normal subject Akt amounts, and correlating with at least one selected from: the cancer, the progression of the cancer, metastasis, invasiveness, enlargement of tumor size, regression of tumor size, disappearance of tumor, no evidence of disease, and remission.

7. The method according to claim 1, further comprising determining cell motility of the sample, and prognosing increased motility with at least one of invasiveness and metastasis in the patient.

8. The method according to claim 1, further comprising measuring upregulation of expression of at least one miRNA in hypoxic cells or in a hypoxic tumor.

9. The method according to claim 1, further comprising measuring decreased expression of miR-200a and prognosing the cancer or the cancer progression in the patient.

10. The claim according to claim 9, further comprising measuring decreased expression of at least one miRNA regulated by the imbalance of Akt isoforms having the decreased ratio of the Akt1 protein to the Akt2 protein compared to the normal subject, and prognosing the cancer or the cancer progression in the patient.

11. The method according to claim 10, further comprising measuring the decreased expression of the miRNA species regulated by the imbalance of expression of at least one of the Akt1 protein and the Akt2 protein, and prognosing the cancer or the cancer progression in the patient.

12. The method according to claim 11, further comprising measuring the miRNA species regulated by the reduced expression of the Akt1 protein, and prognosing the cancer or the cancer progression in the patient.

13. The method according to claim 1, further comprising measuring increased expression of the miRNA species regulated by the imbalance of at least one of the Akt1 protein, the Akt2 protein and an Akt3 protein, and prognosing the cancer or the cancer progression in the patient.

* * * * *